(12) United States Patent
Gutierrez-Uribe et al.

(10) Patent No.: US 7,763,292 B2
(45) Date of Patent: Jul. 27, 2010

(54) **CANCER CELL GROWTH INHIBITION BY BLACK BEAN (*PHASEOLUS VULGARIS* L) EXTRACTS**

(75) Inventors: Janet A. Gutierrez-Uribe, Monterrey (MX); Sergio R. O. Serna-Saldivar, Monterrey (MX); Jorge E. Moreno-Cuevas, San Pedro Garza Garcia (MX); Carmen Hernandez-Brenes, San Pedro Garza Garcia (MX); Elsa M. Guajardo-Touche, San Pedro Garza Garcia (MX)

(73) Assignee: Instituto Technologico y de Estudios Superiores de Monterrey, Minterrey (MX)

( * ) Notice: Subject to any disclaimer, the term of this patent is extended or adjusted under 35 U.S.C. 154(b) by 415 days.

(21) Appl. No.: 11/125,782

(22) Filed: May 10, 2005

(65) Prior Publication Data

US 2006/0024394 A1 Feb. 2, 2006

Related U.S. Application Data

(60) Provisional application No. 60/570,029, filed on May 10, 2004.

(51) Int. Cl.
*A61K 36/48* (2006.01)
*A61K 9/12* (2006.01)
*A21D 2/02* (2006.01)

(52) U.S. Cl. .......................... 424/757; 426/331; 424/44
(58) Field of Classification Search ....................... None
See application file for complete search history.

(56) References Cited

U.S. PATENT DOCUMENTS

| | | | |
|---|---|---|---|
| 5,320,949 A | 6/1994 | Shen | |
| 5,336,685 A | 8/1994 | Prochaska et al. | |
| 5,352,384 A | 10/1994 | Shen | |
| 5,637,561 A | 6/1997 | Shen et al. | |
| 5,637,562 A | 6/1997 | Shen et al. | |
| 5,762,936 A | 6/1998 | Ronzio et al. | |
| 6,004,558 A | 12/1999 | Thurn et al. | |
| 6,146,668 A | 11/2000 | Kelly et al. | |
| 6,410,061 B1 | 6/2002 | Morre et al. | |
| 6,479,539 B1 | 11/2002 | Romanczyk et al. | |
| 6,482,448 B2 | 11/2002 | Tabor | |
| 6,497,906 B1 | 12/2002 | Kelly | |
| 6,500,965 B2 | 12/2002 | Paracchini et al. | |
| 6,514,527 B1 | 2/2003 | Buchholz et al. | |
| 6,541,613 B2 | 4/2003 | Hendler et al. | |
| 6,562,380 B1 | 5/2003 | Kelly | |
| 6,562,863 B2 | 5/2003 | Romanczyk et al. | |
| 6,579,561 B2 | 6/2003 | Bryan et al. | |
| 6,607,757 B2 | 8/2003 | Bombardelli et al. | |
| 2002/0178605 A1* | 12/2002 | Aoki | 34/92 |
| 2003/0068329 A1 | 4/2003 | Kosuna et al. | |
| 2003/0078214 A1 | 4/2003 | Kelly | |
| 2003/0104084 A1 | 6/2003 | Ramot et al. | |
| 2003/0108591 A1 | 6/2003 | Meijer et al. | |
| 2003/0113390 A1 | 6/2003 | Hoie | |
| 2003/0118675 A1 | 6/2003 | Waggle et al. | |
| 2003/0125229 A1 | 7/2003 | Rodriguez | |
| 2003/0125265 A1 | 7/2003 | Hung et al. | |
| 2003/0129217 A1 | 7/2003 | Festo | |
| 2003/0129258 A1 | 7/2003 | Pushpangadan et al. | |
| 2004/0131749 A1 | 7/2004 | Grabiel et al. | |

FOREIGN PATENT DOCUMENTS

| | | |
|---|---|---|
| CN | 1283449 A | 2/2001 |
| CN | 1329846 A | 1/2002 |
| KR | 2001084705 A | 9/2001 |
| KR | 2002071152 A | 9/2002 |
| WO | WO-82/00035 A | 1/1982 |

OTHER PUBLICATIONS http://www.oncologychannel.com/braincancer/treatment.shtml.*
BIC Mar. 2004, The XL VII Report of the Bean Improvement Cooperative, No. 47, p. 185-186.*
Tsuda et al., Antioxidative Pigments Isolated from the Seeds of *Phaseolus vulgaris* L., 1994, J. Agric. Food Chem, 42, 248-251.*
Fossen et al., Anthocyanins from Maize (Zea mays) and Reed Canarygrass (*Phalaris arundinacea*), 2001, J. Agric. Food Chem., 49, 2318-2321.*

(Continued)

*Primary Examiner*—Michael V. Meller
*Assistant Examiner*—Catheryne Chen
(74) *Attorney, Agent, or Firm*—Frommer Lawrence & Haug, LLP; A. Thomas S. Safford

(57) ABSTRACT

This invention relates to processes or methods for the production of compositions comprising extracts of black beans containing phenolics, such as polyphenols, flavonoids, and tannins, phytosterols, and triterpenoids such as saponins and other natural products with proven antioxidant capacity, colorant capacity, and uses thereof, e.g., as antioxidants, nutritional supplements, as food, cosmetic or pharmaceutical antioxidants or colorants, as antineoplastic or anti-cancer or antitumor preparations, e.g., to treat, prevent and/or inhibit cancers or cancer cell growth, such as hormone dependent or hormone independent tumors or cancers or cancer cells. such as mammalian mammary, prostate, colon, hepatic, leukemia cancer or cancer cell growth, as active ingredient(s) in compositions for lowering cholesterol or lowering oxidation of LDL or for inhibiting cholesterol synthesis (or the enzyme therefor), as an active ingredient(s) in compositions, e.g., nutritional supplements.

30 Claims, 30 Drawing Sheets

OTHER PUBLICATIONS

Beninger et al., Antioxidant Activity of Extracts, Condensed Tannin Fractions, and Pure Flavonoids from *Phaseolus vulgaris* L. Seed Coat Color Genotypes, 2003, J Agric Food Chem, 51: 7879-7883.*

Lee et al., Analysis of Sapnons from Black Bean by Electrospray Ionization and Fast Atom Bombardment Tandem Mass Spectrophotometry,1999, 34: 804-812.*

Phytopia prior art date 2001 http://www.phytopia.com/oldsite/phygloss.htm.*

Mayoclinicbreastcancer http://www.mayoclinic.com/health/breast-cancer/DS00328/DSECTION=risk%2Dfactors.*

ScienceDaily http://www.sciencedaily.com/releases/2009/05/090514221931.htm.*

Adebamowo, C., Dietary flavonols and flavonol-rich foods intake and the risk of breast cancer, Int. Journal of Cancer, 2005, 114, 628-633, Wiley-Liss, Inc.

Database W PI, Section Ch,W eek 200229;DerwentPublications Ltd.; Jan. 9, 2002 ;,AN 2002-227794XP002357369 & CN 1329846 A ;abstract London,GB.

Database W PI, Section Ch,W eek 200313;DerwentPublications Ltd.; Sep. 12, 2002 ;, AN 2003-137237,XP002357370 & KR 2002 071 152 A; abstract;London, G B.

Database W PI, Section Ch,W eek 200132;DerwentPublications Ltd.; Feb. 14, 2001;,AN 2001-300933,XP002357371 & CN 1283449 A ; abstract; London, G B.

Database WPI, Section Ch, Week 200219;Derwent Publications Ltd.; Sep. 6, 2001;, AN 2002-146092, XP002357372 & KR 2001 084 705 A; abstract; London, GB.

Wu, S.J., et al; "Evaluation of hepatoprotective activity of Legumes;" Phytomedicine; 2001, vol. 8, No. 3, pp. 213-219; Stuttgart, Germany.

Takeoka, G.R. et al; "Characterization of black bean (*Phaseolus vulgaris*, L.) anthocyanins;" Abstracts of Papers American Chemical Society; 1997; vol. 214, AGFD 75; Las Vegas.

Gomez-Brenes, et al; "Effect of various solvents on the extraction of protein fractions of beans (Phaseolus vulgaris);" Archivos Latinoamericanos De Nutricion; Sep. 1983.

Chao, et all; "The antioxidative capacity of black bean extract;" Atherosclerosis; Mar. 1998; vol. 136, pp. S61; Taipei, Taiwan.

Maeda Hiroshi, et al; "High correlation between lipid peroxide radical and tumor-promoter effect;" Japanese Journal of Cancer Research; 1992; vol. 83, NR. 9, pp. 923-928.

Hangen, Laura et al; "Consumption of *Phaseolus vulgaris* (Black beans or navey beans) reduces colon cancer in rats," FASEB Journal; Mar. 2001; vol. 15, NR. 4, p. A61.

Madhujith, T et al; "Antioxidant activity of common beans (*Phaseolus vulgaris* L.);" Journal of Food Lipids; 1997; 11 (3) 220-223 2004 correspondence (reprint); Canada.

Yang, C.M. et al; "Grey prediction comparison on the antioxidative capacity of commercial black bean and soybean;" Nutritional Sciences Journal; 1999; vol. 24, No. 2, 201-214.

Takanori, T. et al; "Antioxidant pigments isolated from the seeds of *phaseolus vulgaris* L;" Journal of Agricultural and Food Chemistry; Feb. 1994; p. 248-249.

Gupta, M.K.; "Processing to improve soybean oil quality;" Inoform, AOCS; Nov. 1993; vol. 4, No. 11, pp. 1267-1272; Chicago.

Milligan, D.; "Soybean high protein separation;" Oil Mill Gazetteer Eng. Management, Inc.; 1972; vol. 77, NR. 2, p. 50, Des Plaines, Il.

H.A. Bawadi et al ;"*Inhibition of Caco-2-colon, MCF-7 and Hs578T breast, and DU 145 prostatic cancer cell proliferation by water-soluble black bean condensed tannins*"; (2005), Cancer Letters, vol. 218, pp. 153-162.

Bergeron, C. et al., Comparison of the Chemical Composition of Extracts from Scutellaria lateriflora Using Excellerated Solvent . . . , J. of Agr. and Food Chem., 2005, 53.

Sagar, S. M., Should Patients Take or Avoid Antioxident Supplements during anticancer therapy? An evidence-based review, Current Oncology, vol. 12, No. 2.

Zhang, y., Human tumor cell growth inhibition by nontoxic anthocyanidins, the pigments in fruits and vegetables, Elsevier Life Sciences, 2005, 1467-1472.

Reynertson, K., Bioactive Depsides and Anthocyanins from Jaboticaba, J. Nat. Prod., 2006, 69, 1228-1230.

* cited by examiner

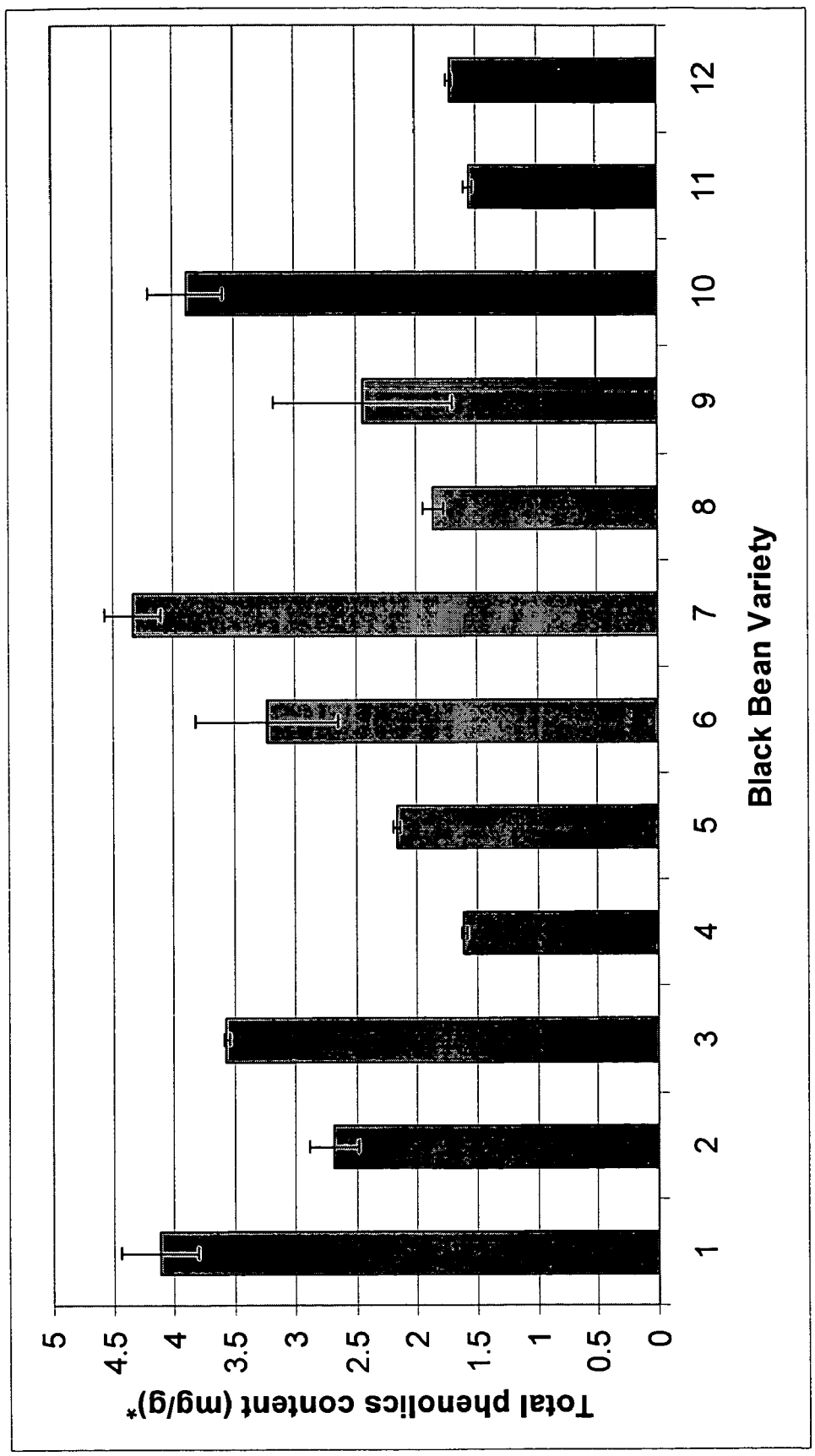
Figure 1. Total phenolic content expressed as catechin equivalents of 12 types of black beans.

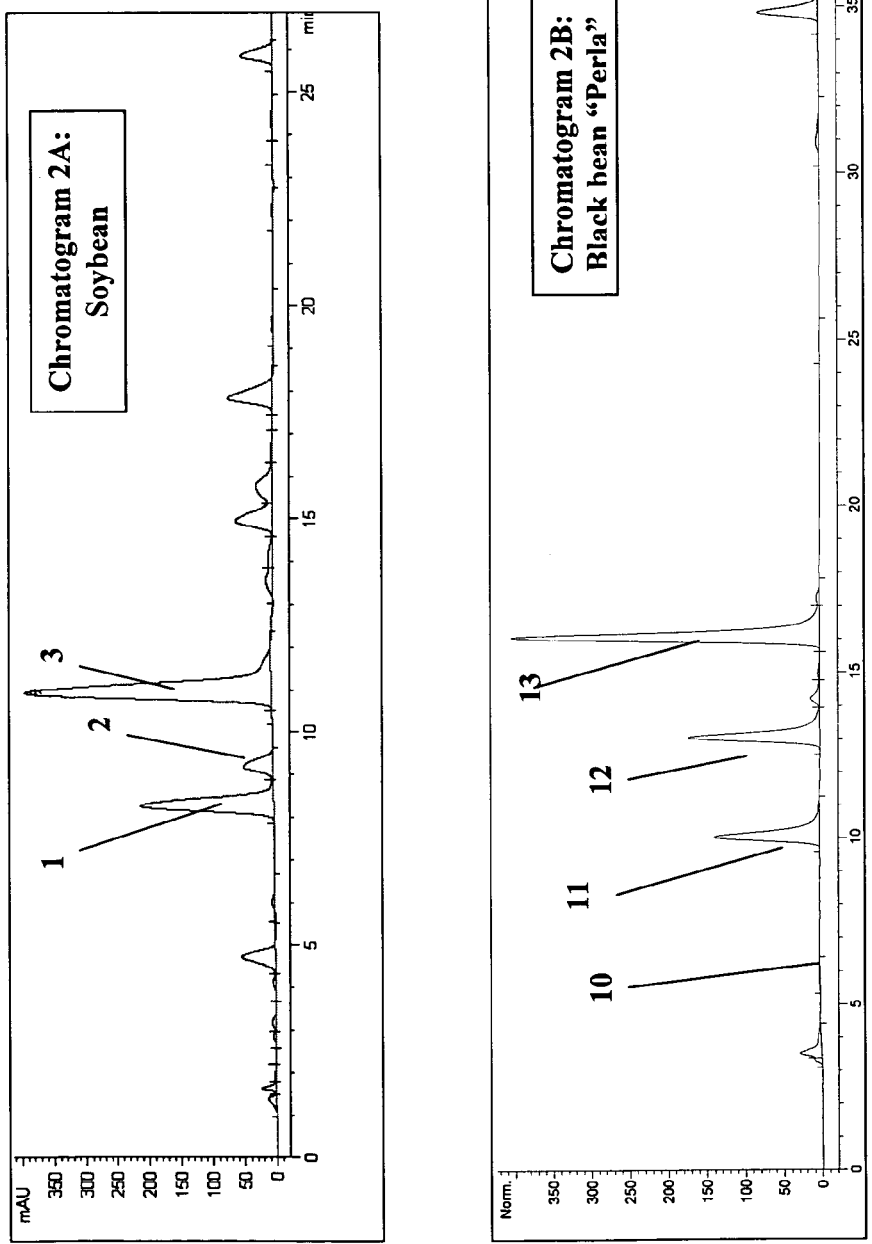
Figure 2. Comparison of flavonoids that absorbed at 262 nm from extracts of soybean (2A) and NG-Perla black bean variety (2B) determined via HPLC-UV.

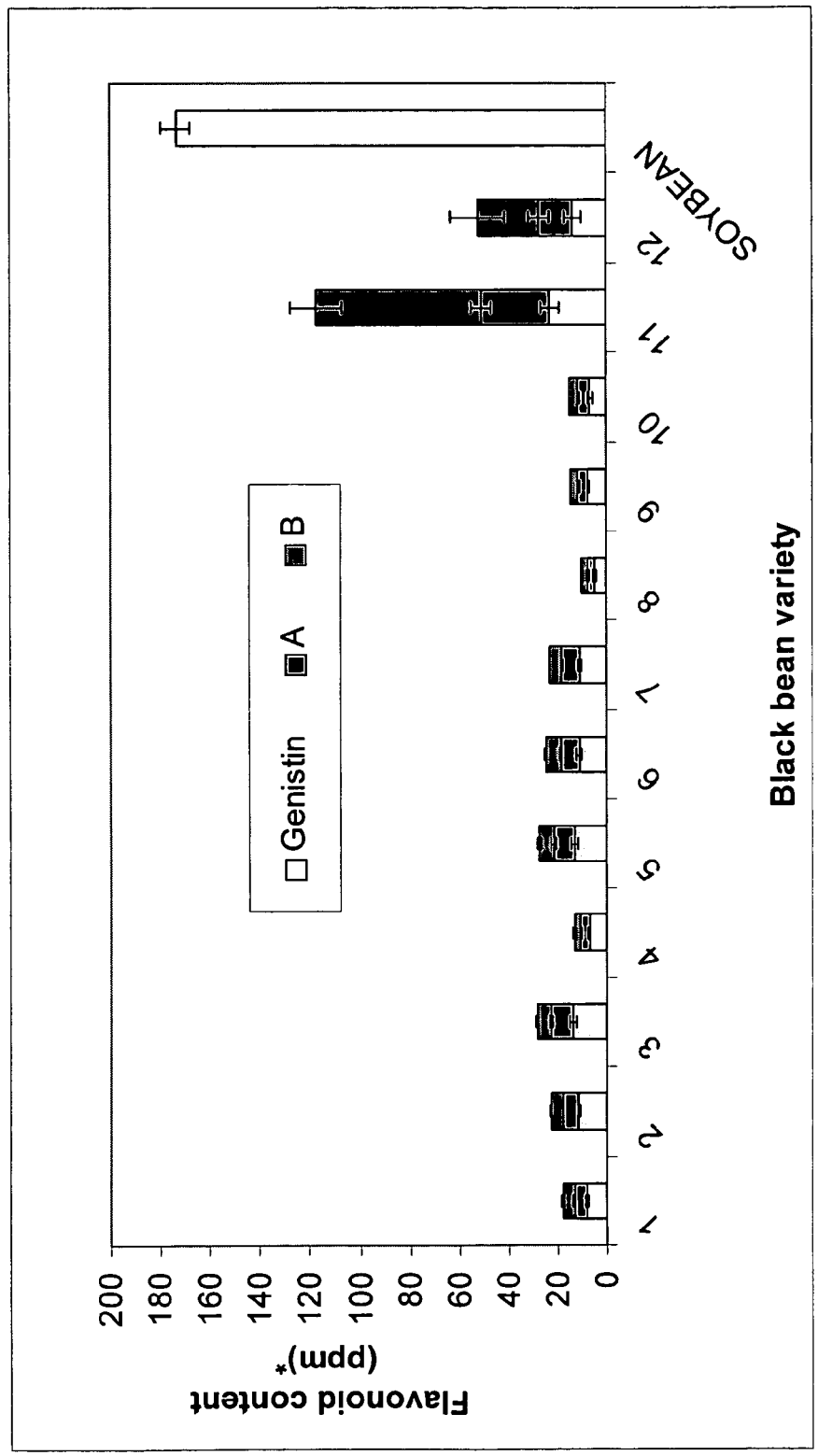
Figure 3. Flavonoids types and concentrations of different varieties of black beans and soybeans quantified by HPLC-UV at 262 nm.

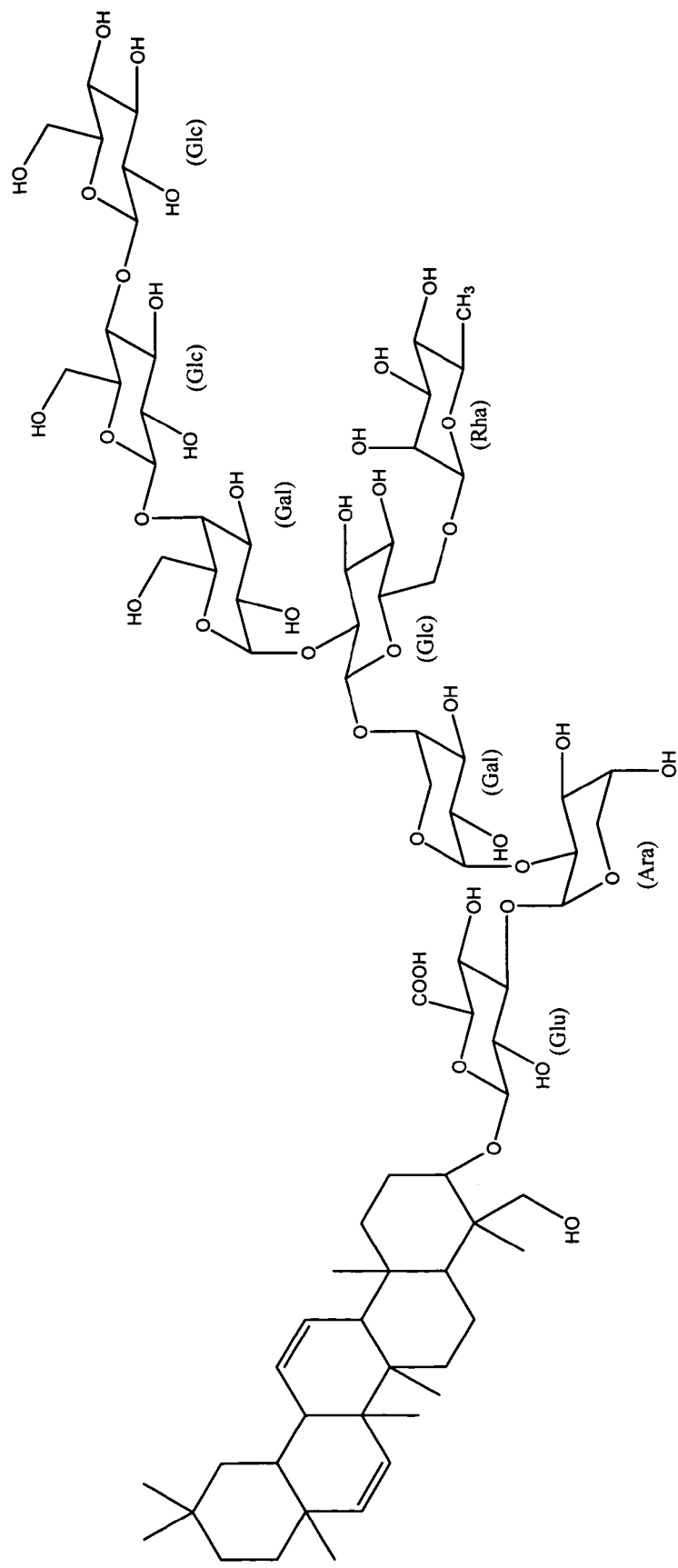
Figure 3a - Structure of Phaseoloside E

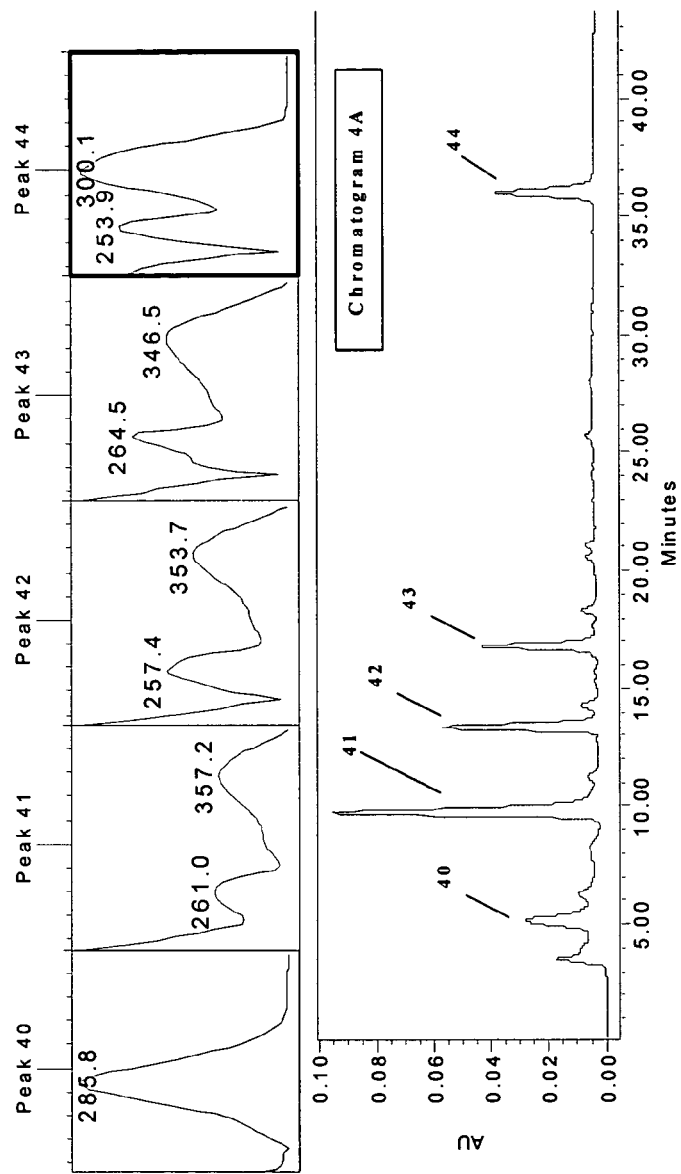
Figure 4a. HPLC-PDA chromatograms (262nm) and their corresponding Peak Spectra of NG-Perla black bean extracts "second fraction" treated without (4A) acid hydrolysis.

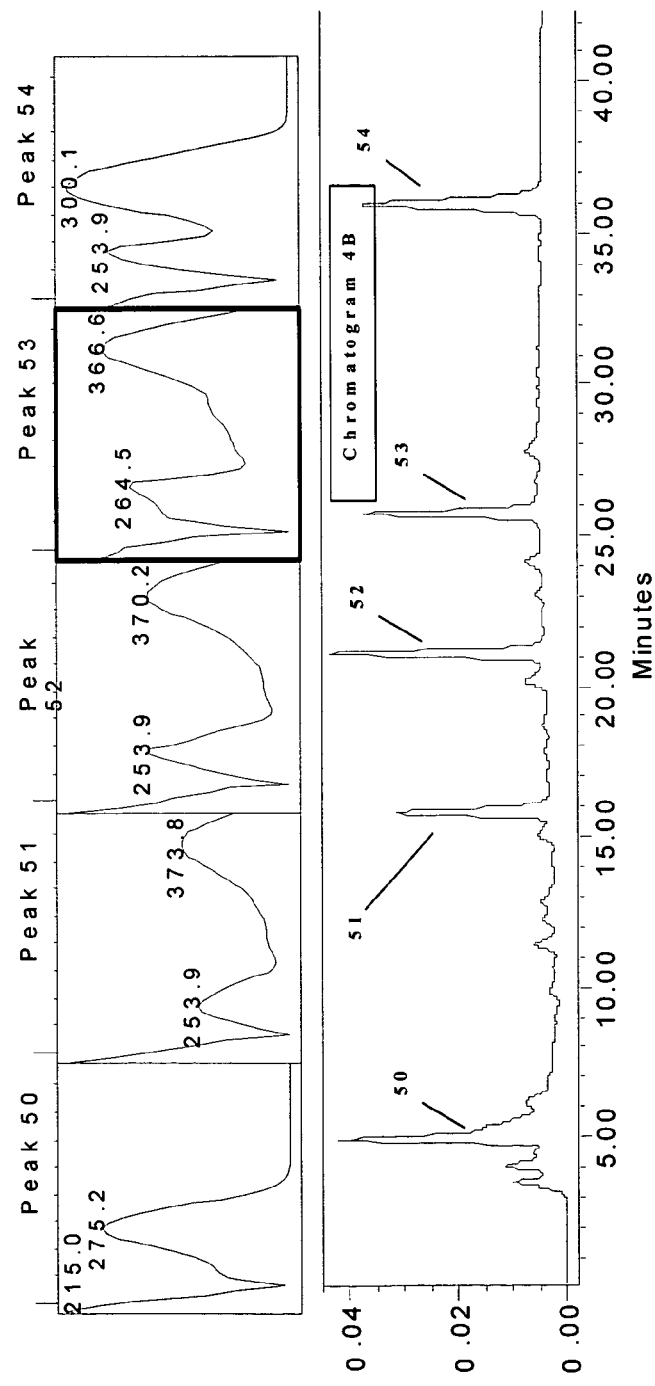
Figure 4b. HPLC-PDA chromatograms (262nm) and their corresponding Peak Spectra of NG-Perla black bean extracts "second fraction" treated with (4B) acid hydrolysis.

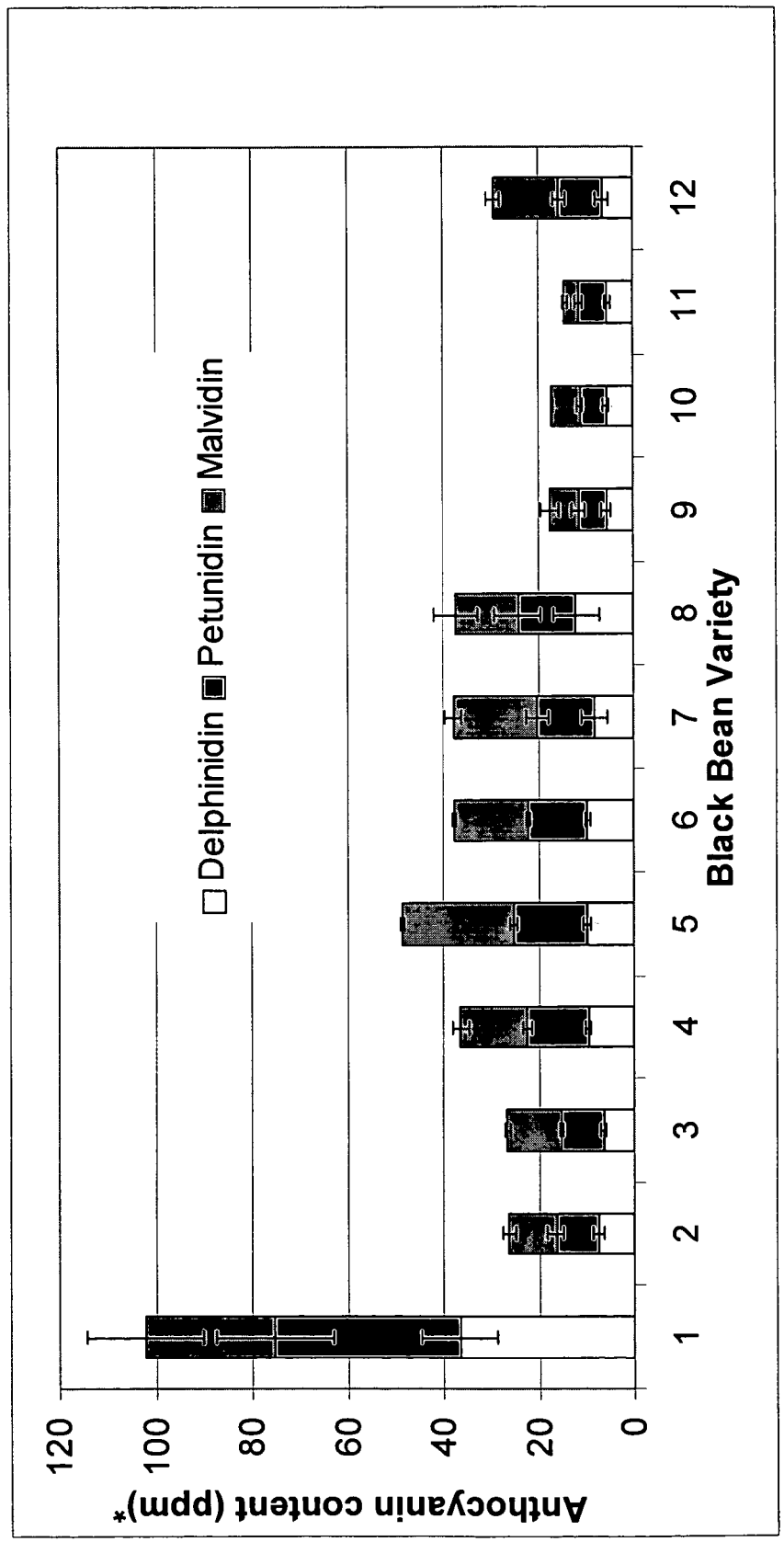
Figure 5 Concentration of anthocyanins delphinidin, petunidin and malvidin in the "second fraction" of 12 different black bean varieties.

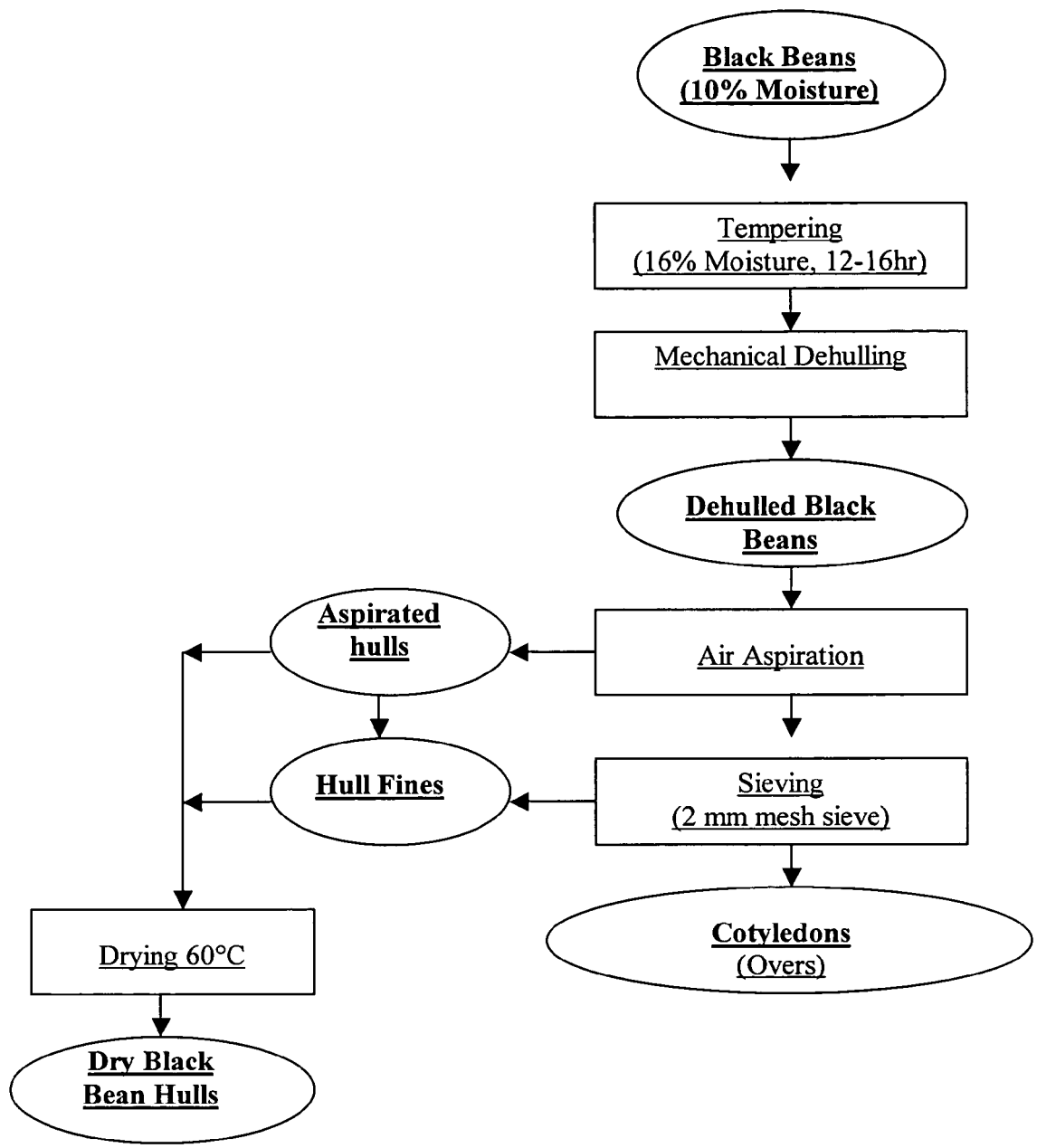
Figure 6a. Experimental milling procedure to obtain seed coats or hulls from black beans.

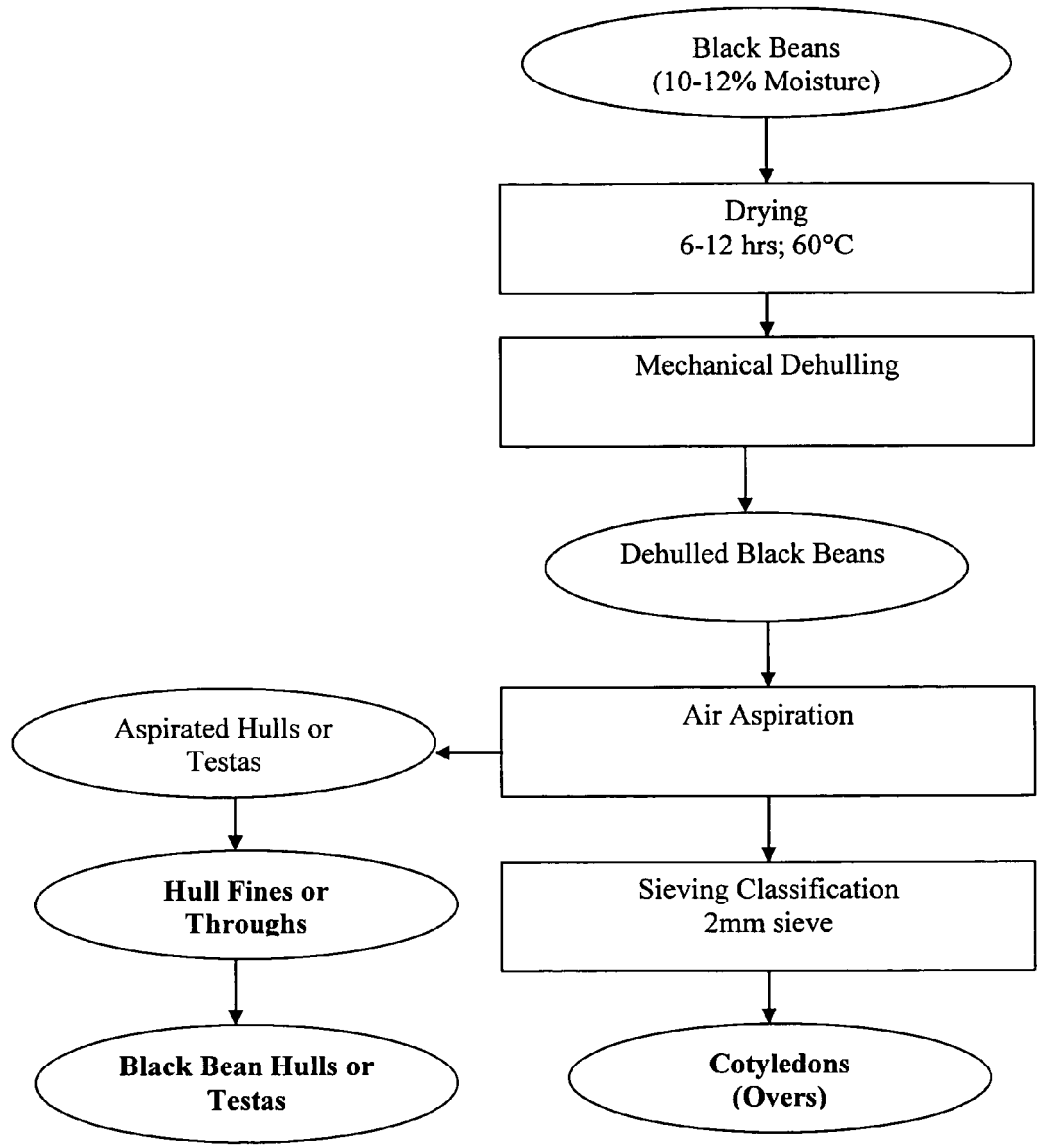
Figure 6b. Experimental milling procedure to obtain seed coats or hulls from black beans using the dehydration procedure.

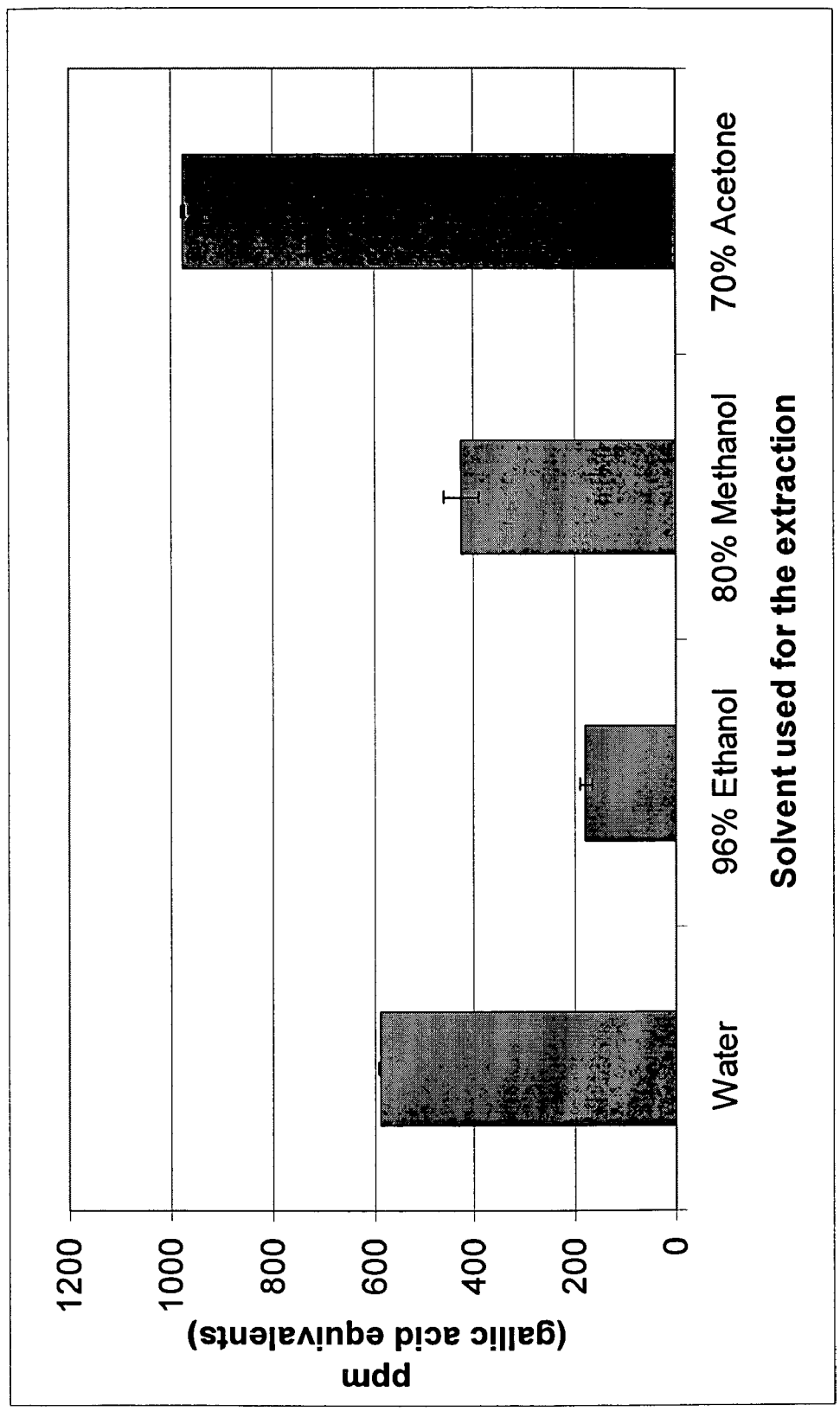
Figure 7. Comparison of total phenolics obtained from black bean hulls extracts.

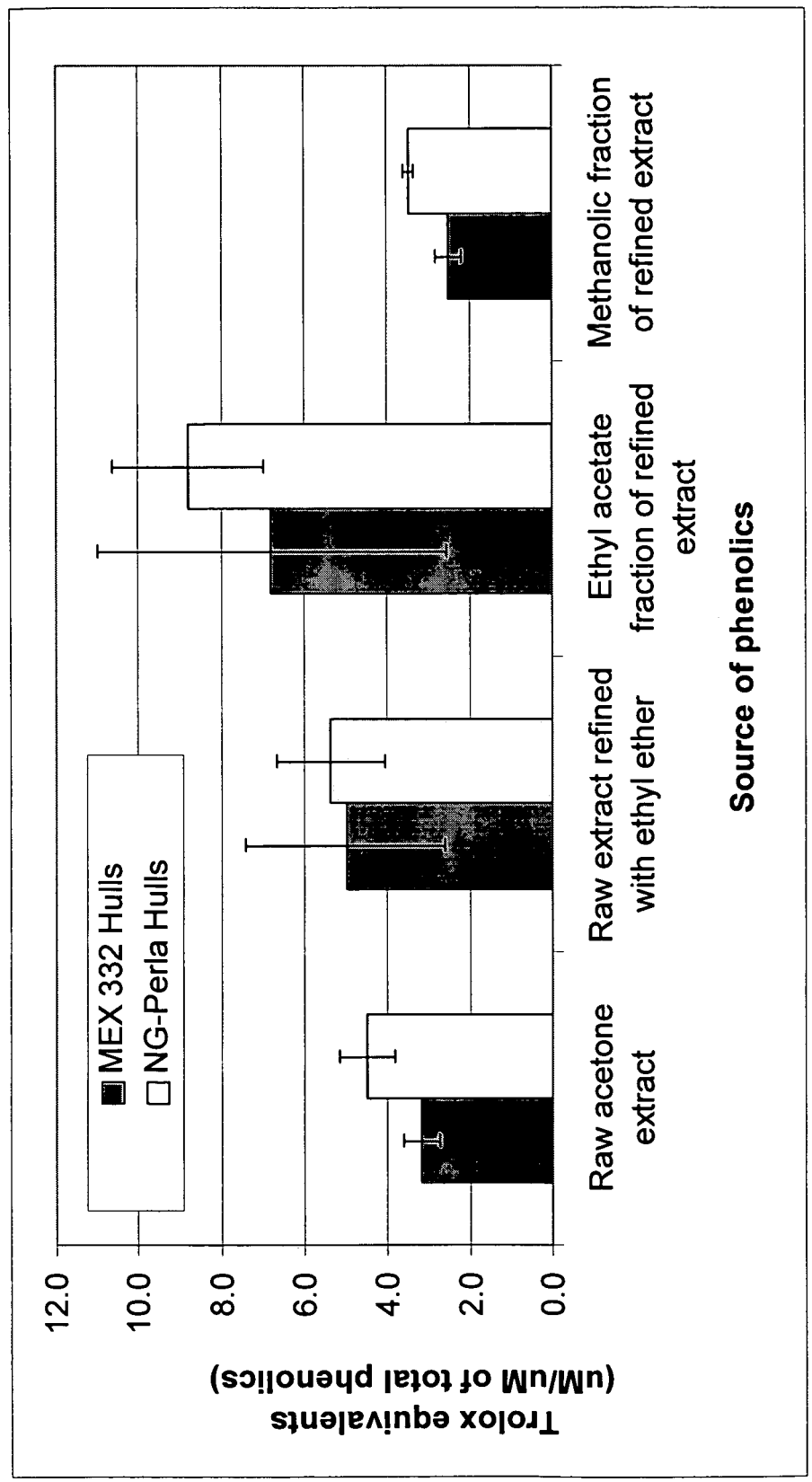
Figure 8. Trolox equivalents ($\mu M/\mu M$ of total phenolics) obtained by the ORAC.

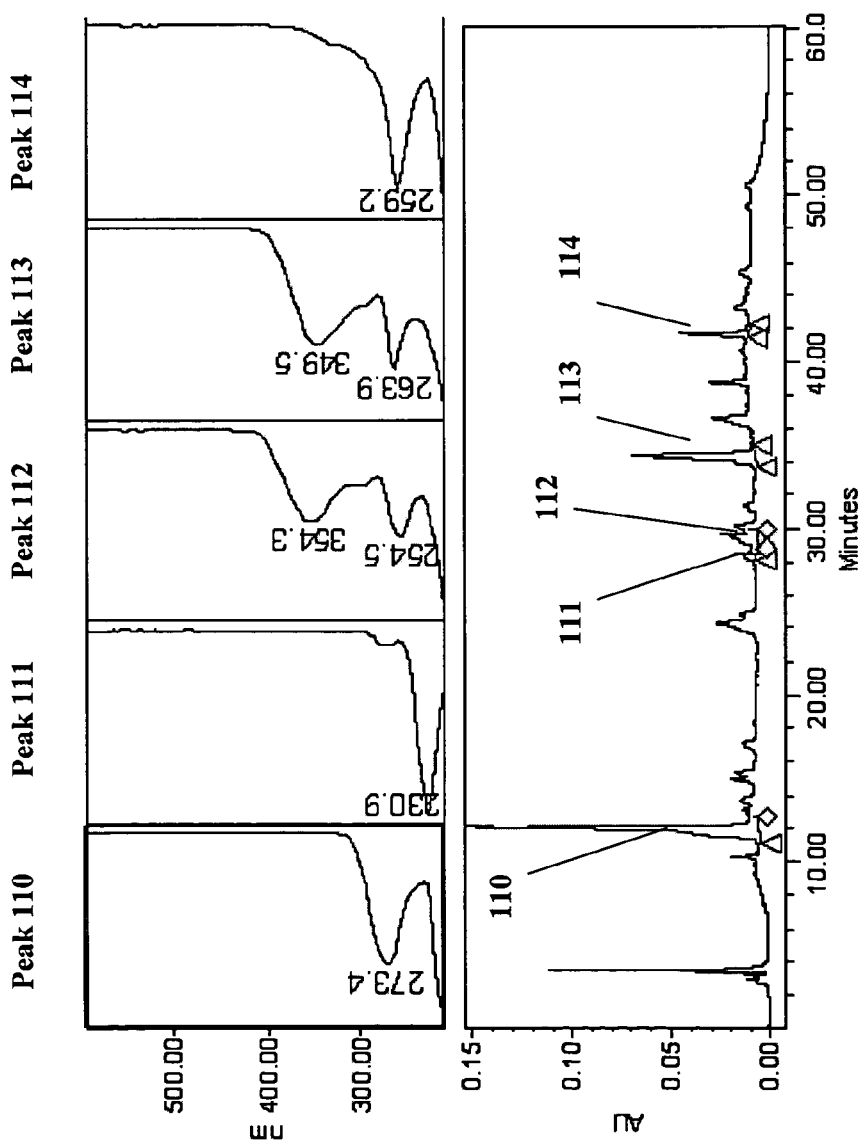
Figure 9. Chromatogram of an extract of flavonoids from 1 day germinated black bean variety NG-Perla obtained by HPLC-PDA at 262 nm with corresponding spectrums of the major peaks.

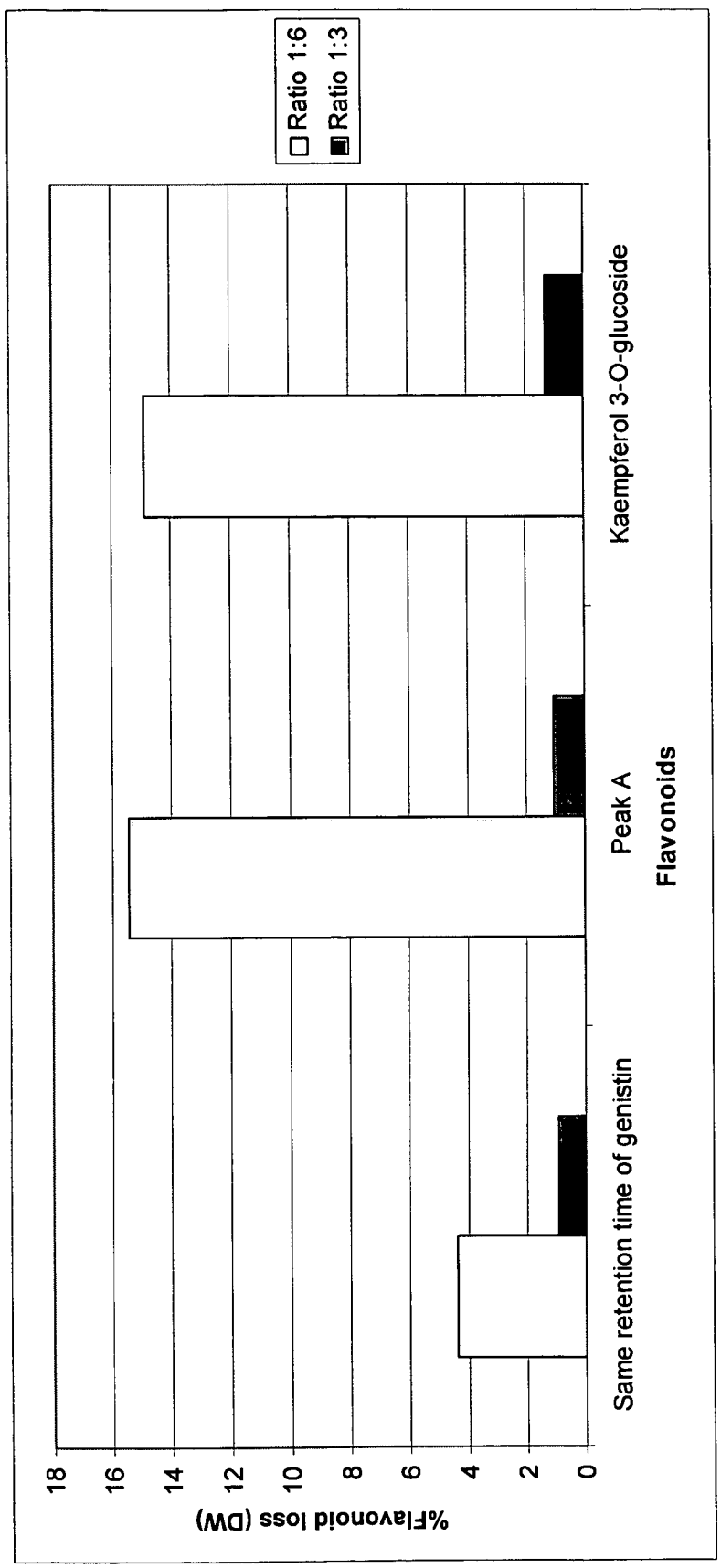
Figure 10. Effect of different bean:water ratios on flavonoid loss from beans into the soaking water.

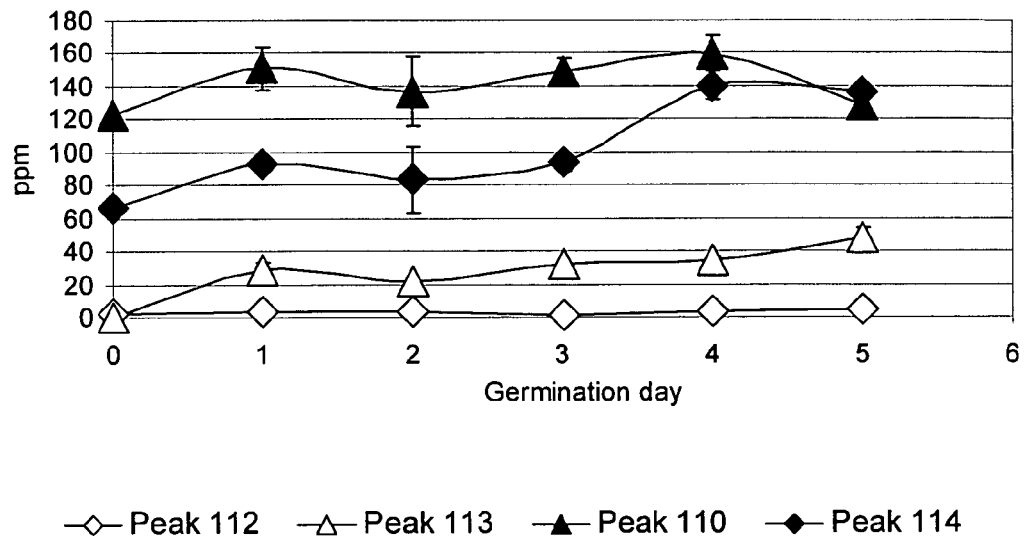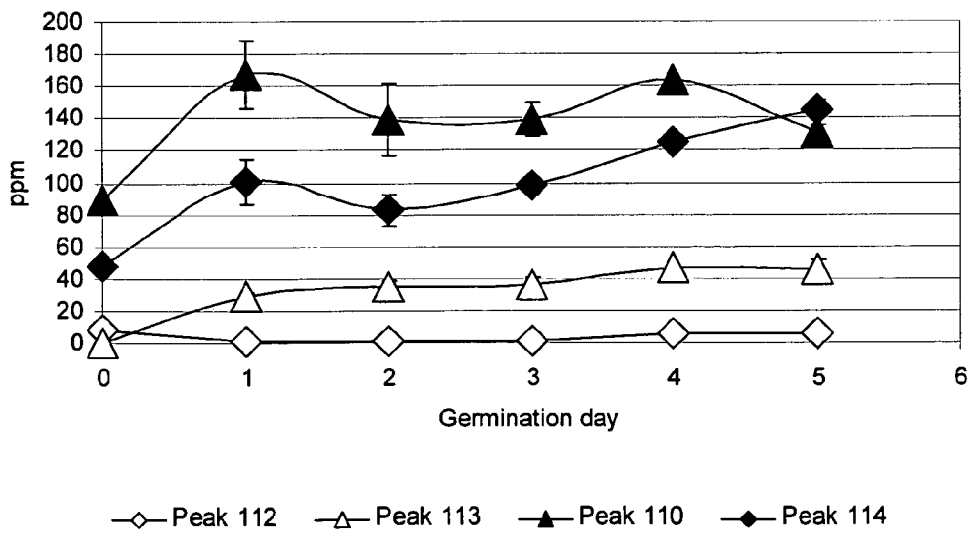
Figures 11A and 11B. Effect of germination time on the concentration of flavonoids.

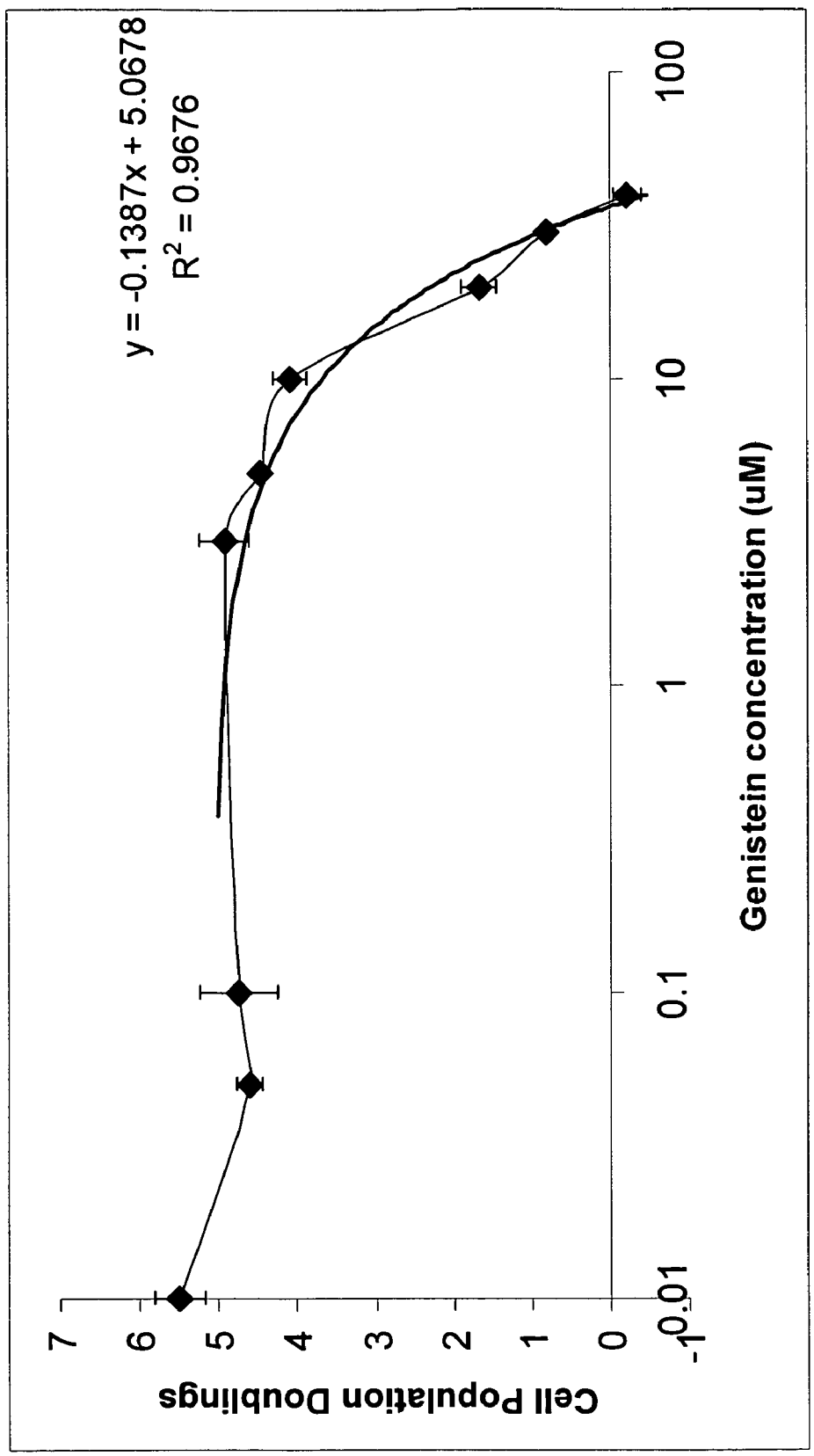
Figure 12. Effect of genistein concentration on *in vitro* mammary cancer cell (MCF-7) proliferation.

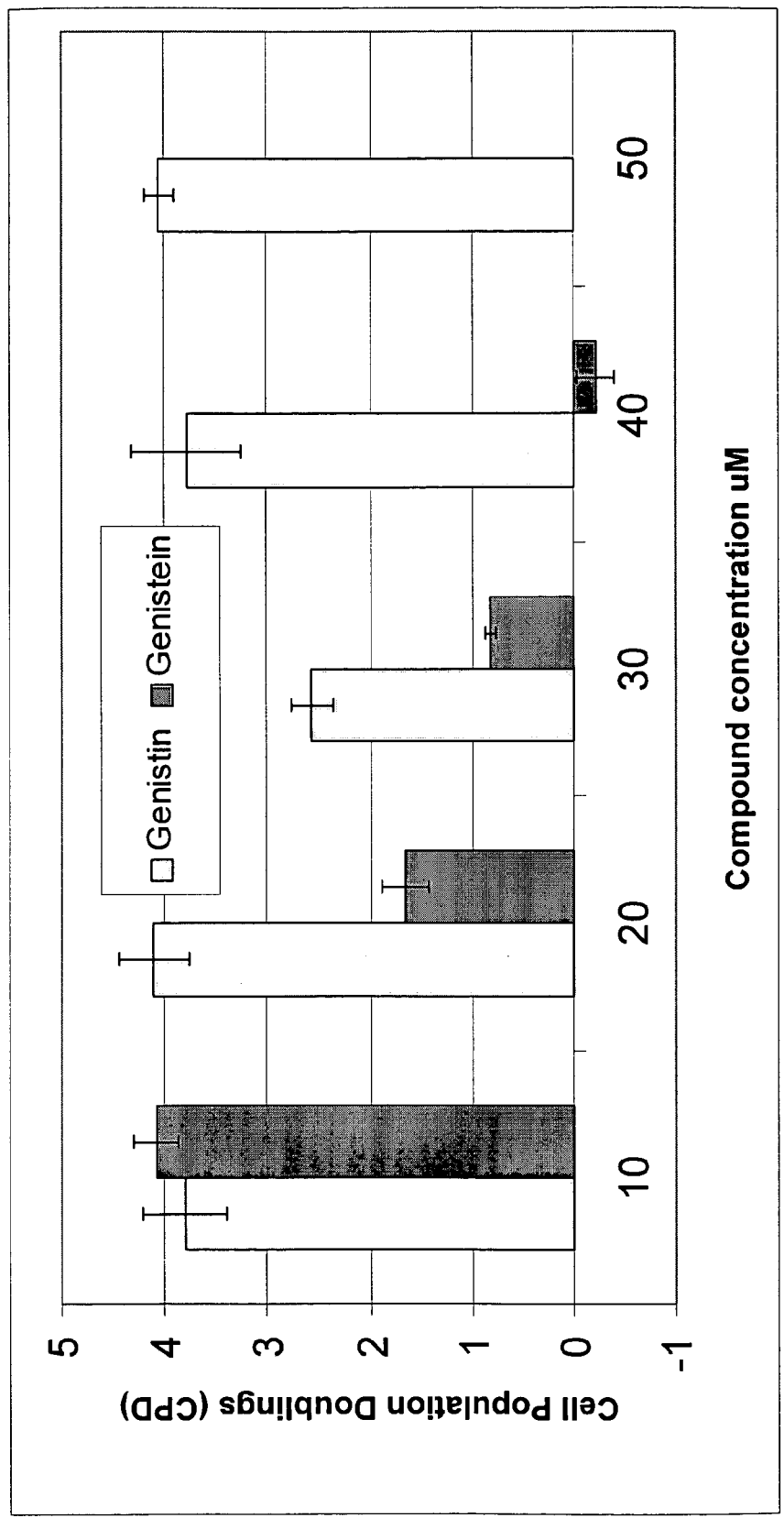
Figure 13. Comparison between inhibitory effects of genistin and genistein on *in vitro* mammary cancer cell (MCF-7) proliferation.

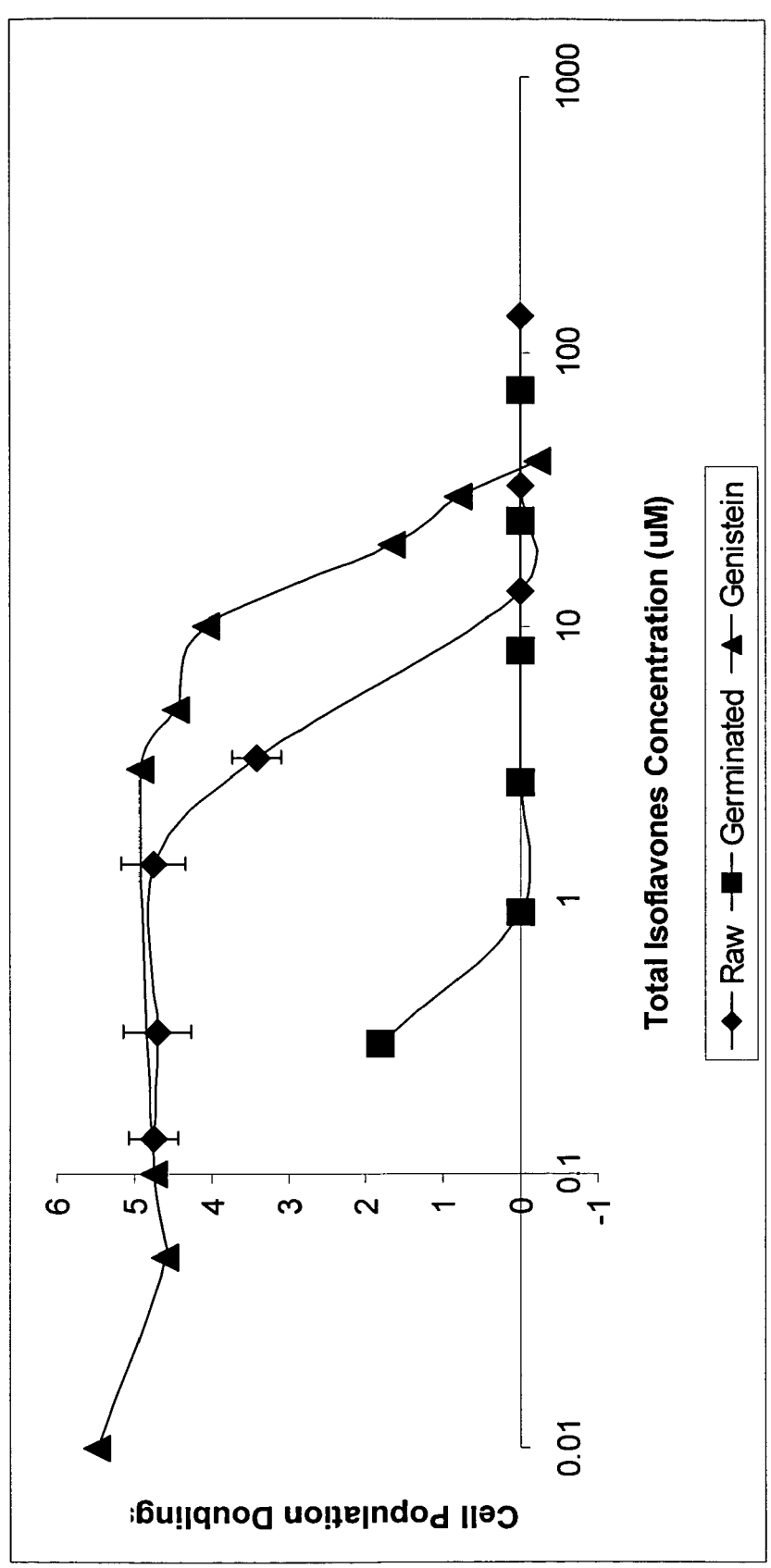
Figure 14. Comparison between raw and germinated black bean extracts and genistein on inhibition of mammary cancer cell (MCF-7) growth cultured *in vitro*.

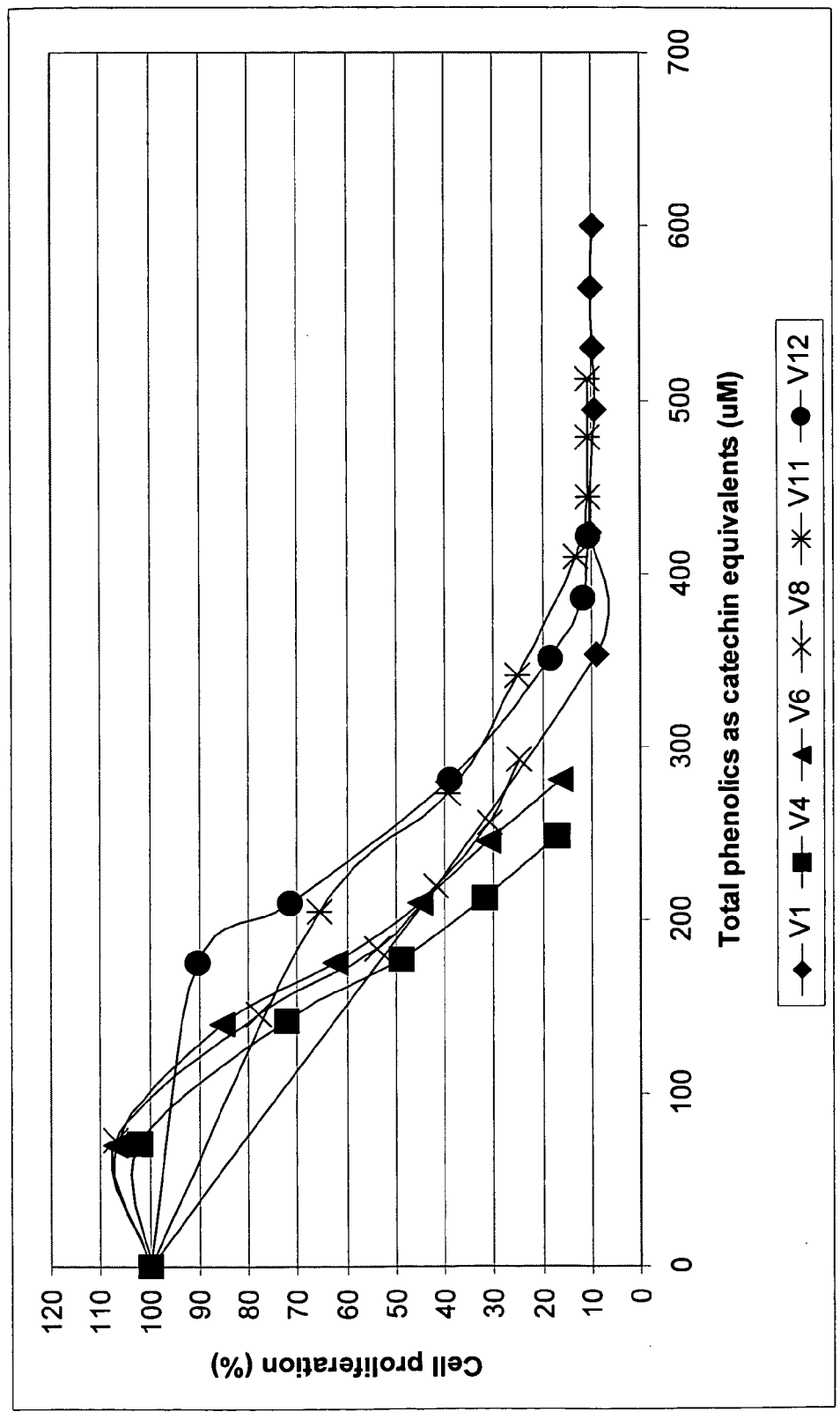
Figure 15. Percent *in vitro* cell proliferation of HepG$_2$ exerted by 6 black bean extracts.

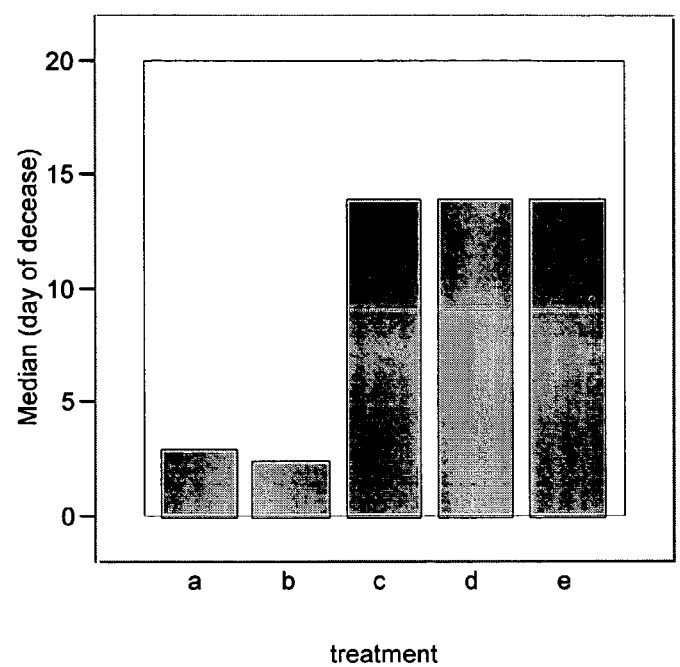
Figure 16. Median decease time (days) after administration of DMBA in Wistar rats that did not resist the induction.

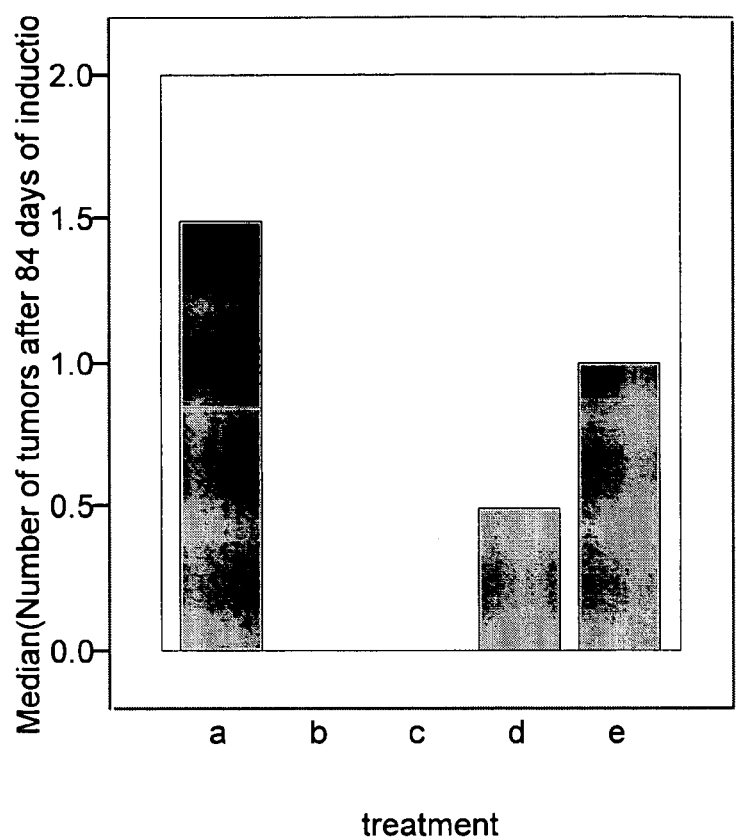
Figure 17. Median number of tumors after 84 days of DMBA cancer induction in Wistar rats that survived DMBA intoxication.

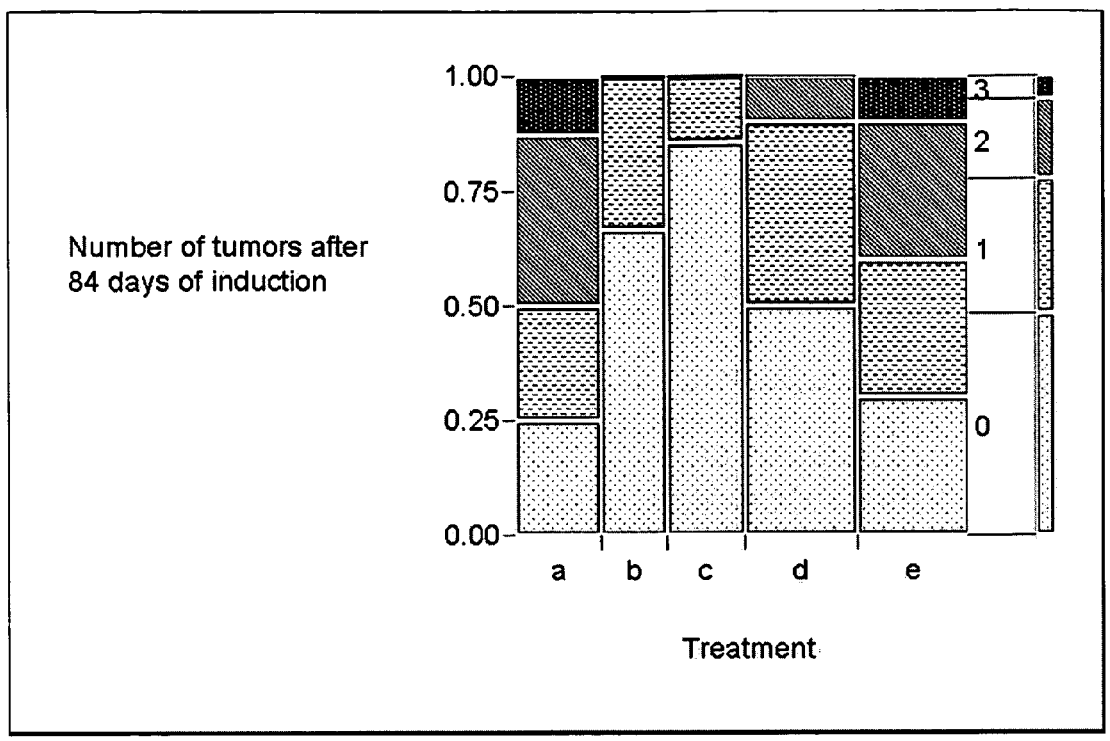
Figure 18. Analysis of number of tumors after 84 days of DMBA cancer induction by treatment consisting in diet for all Wistar rats tested.

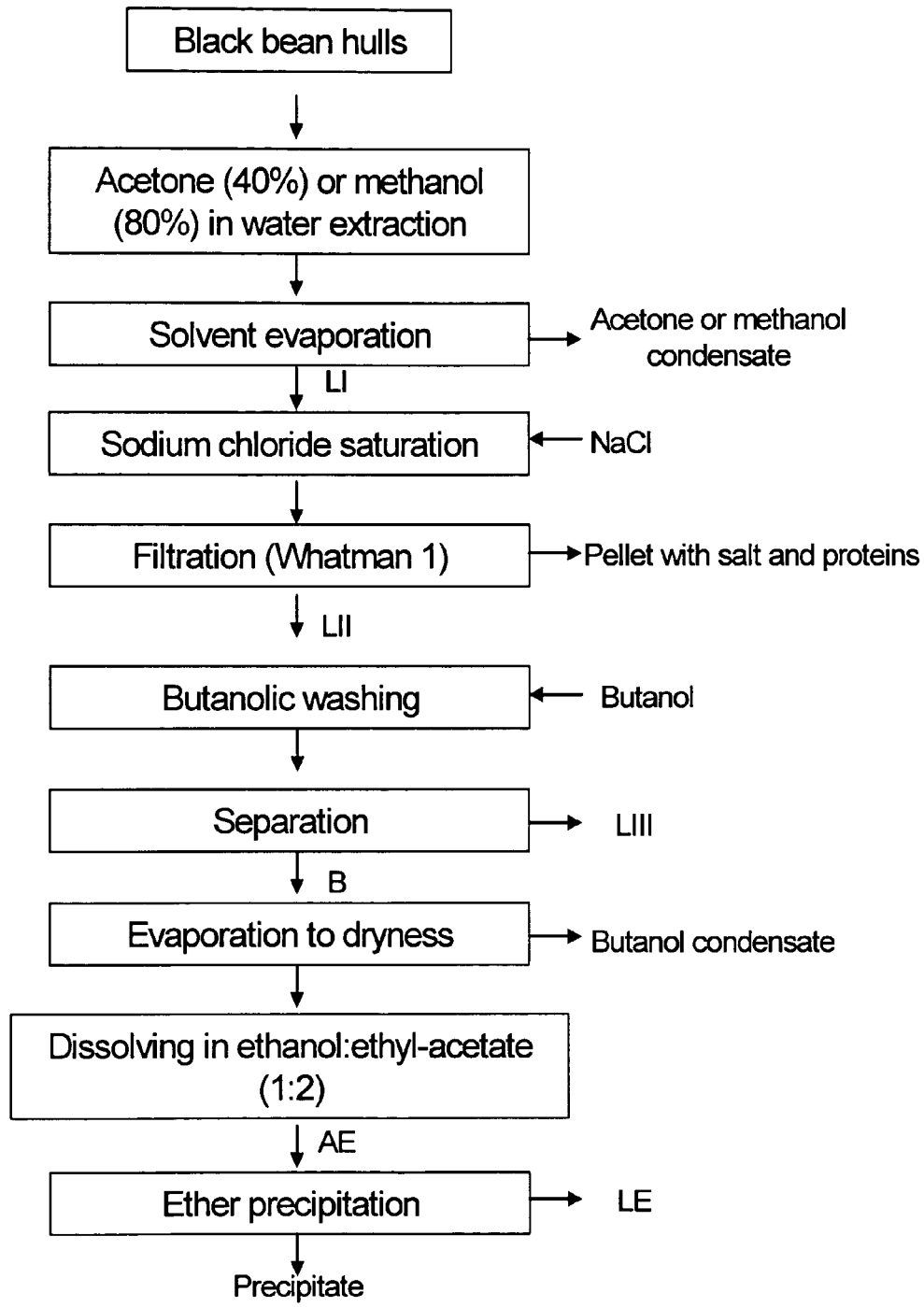
Figure 19. Sequential separation scheme developed to obtain different fractions with different concentrations and types of phenolics and related bioactive compounds

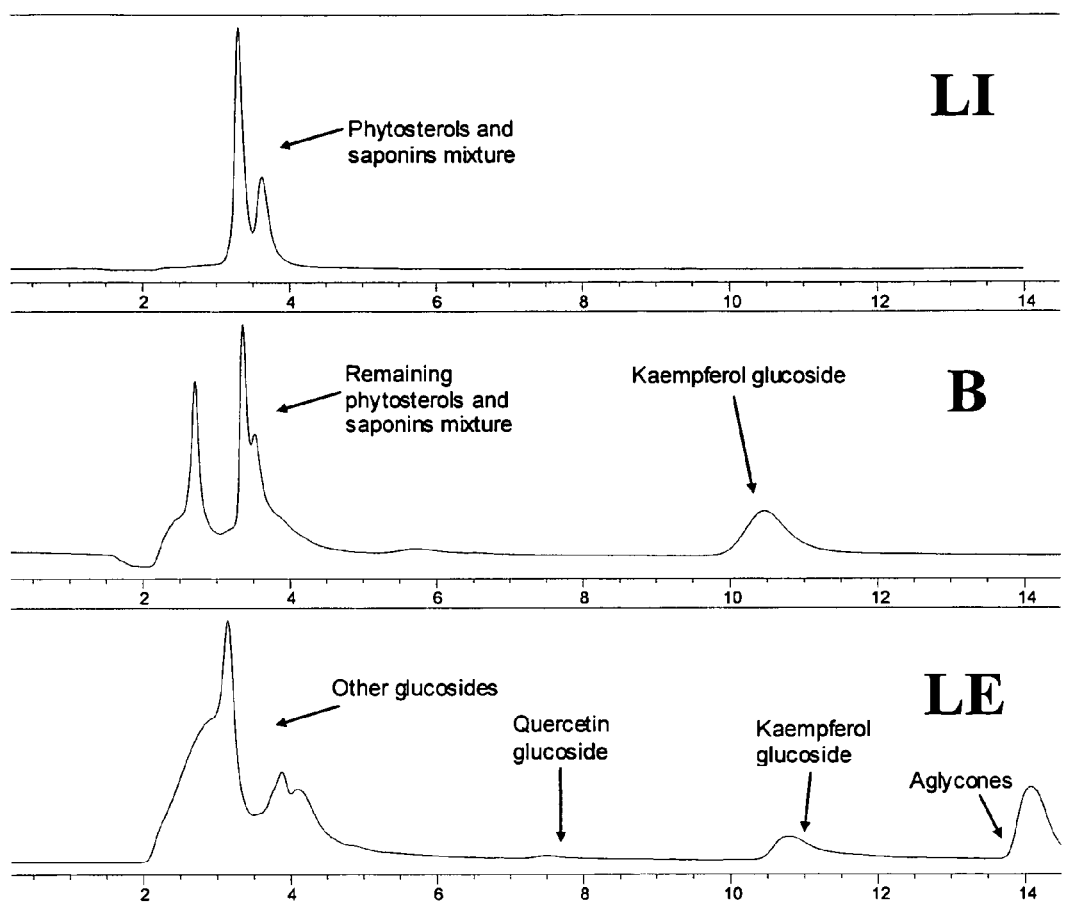
Figure 20. Chromatogram of the different fractions showing the purification of flavonol glycosides from black bean hulls extracts initially obtained with 80% methanol in wate

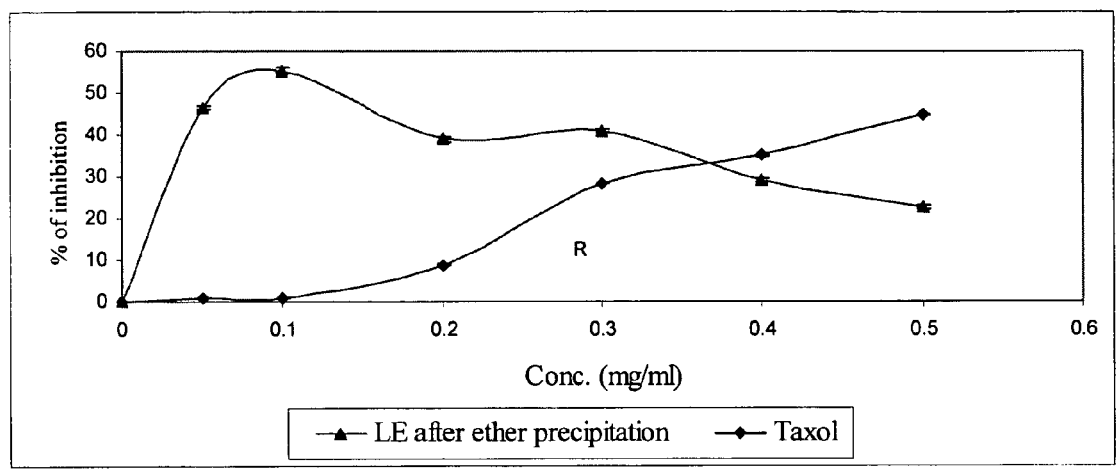
Figure 21. Comparative effect of the LE fraction obtained from black bean hulls initially extracted with 80% methanol and Taxol® on the *in vitro* growth of MCF- 7 mammary cancer cells.

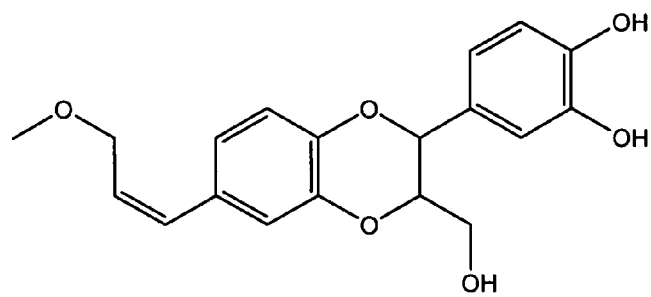
9'-O-Methylamericanol A
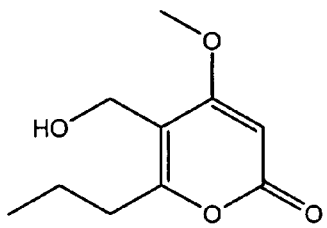
5-(hydroxymethyl)-4-methoxy-6-propyl-2H-pyran-2-one
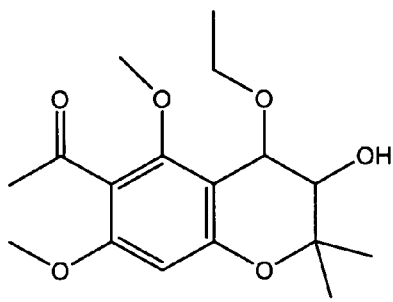
6-acetyl-4-ethoxy-3,4-dihydro-5,7-dimethoxy-2,2-dimethyl-2H-1-benzopyan-3-ol
Figure 22. Chemical structures of compounds with similar UV-light absorption spectrum than unknown compounds present in the LE fraction.

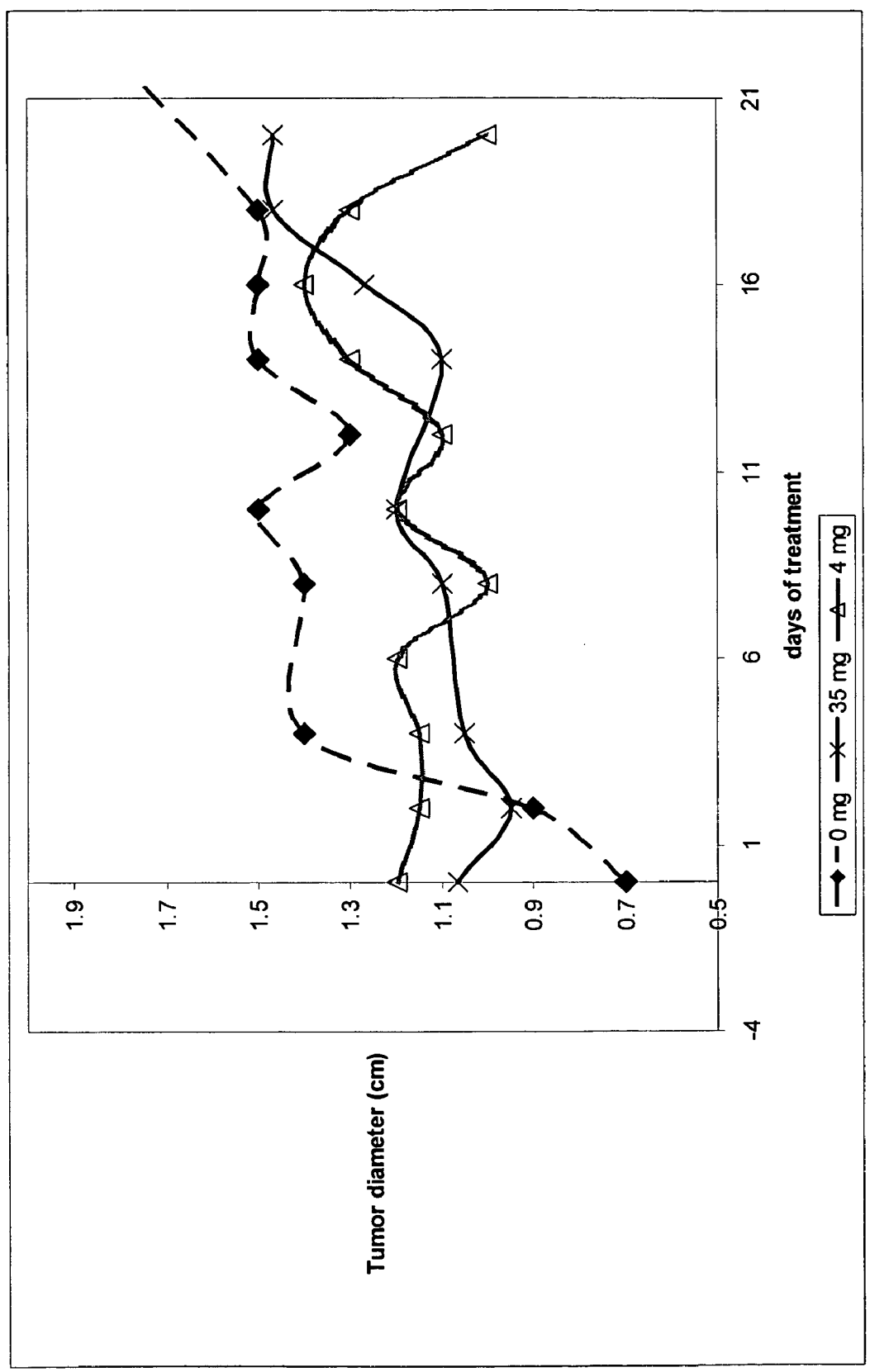
Figure 23a. Shows the tumor growth rate in Wistar rats administered extracts from raw black bean hulls.

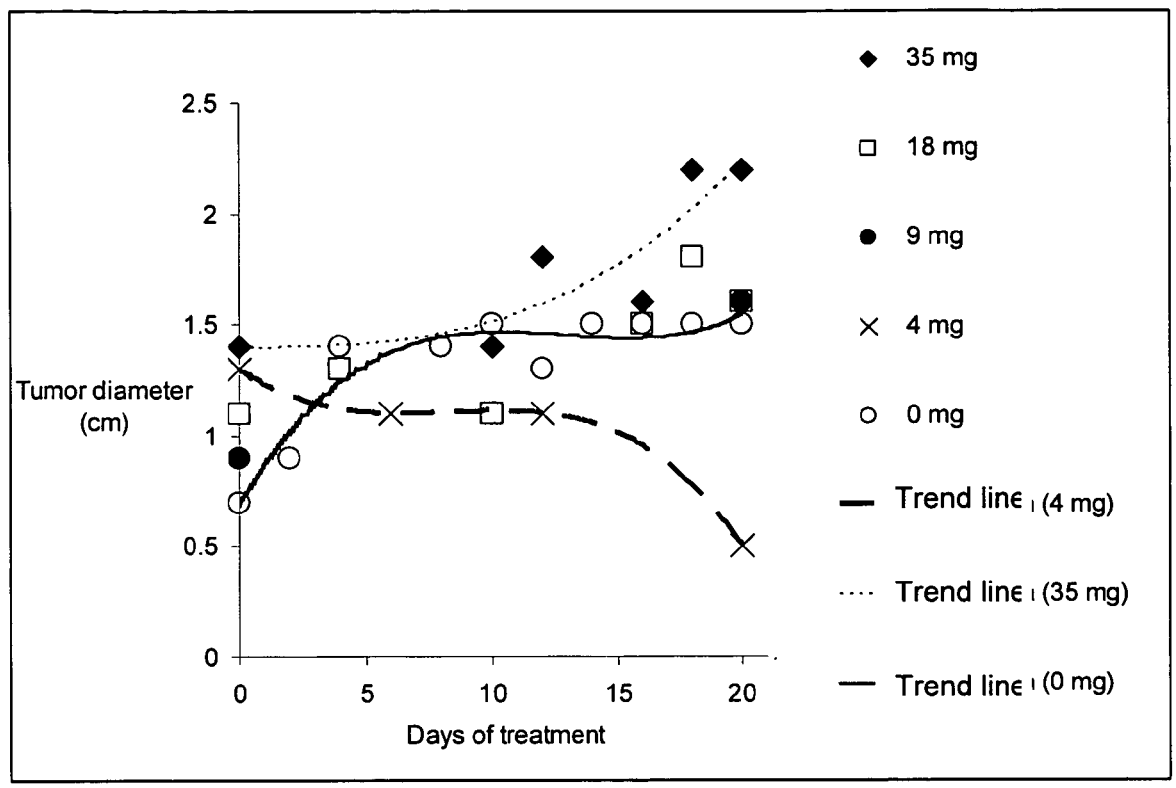
Figure 23b. Tumor growth using different concentrations of black bean hulls.

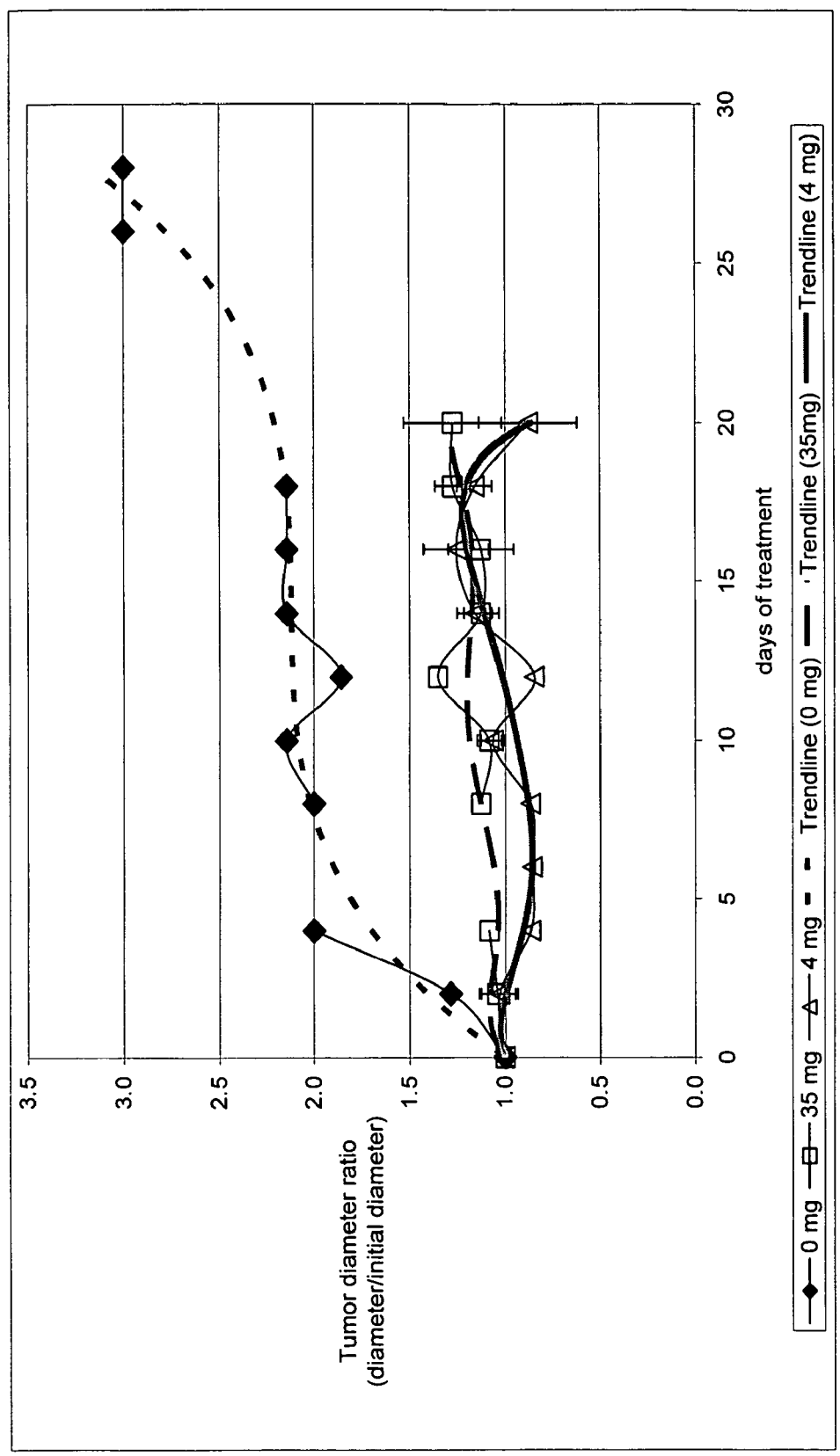
Figure 23c. Change of tumor diameter in Wistar rats.

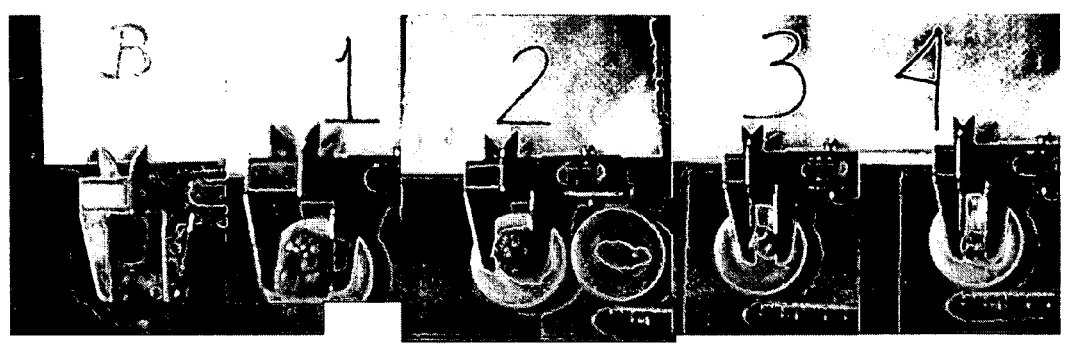
Figure 24. Comparison of tumor size of tumors extracted from Wistar rats.

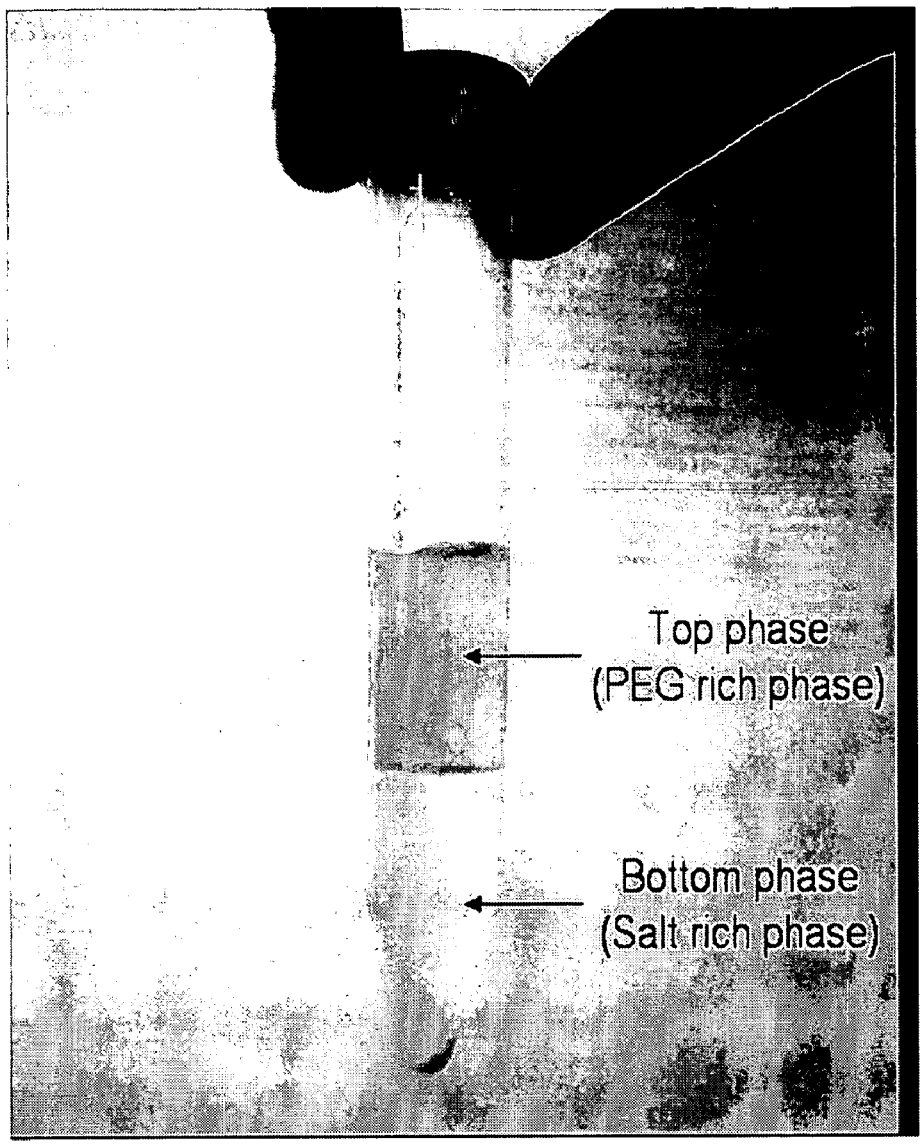
Figure 25. Example of an Aqueous-Two Phase System for the separation of phytochemicals from black bean.

CANCER CELL GROWTH INHIBITION BY BLACK BEAN (*PHASEOLUS VULGARIS* L) EXTRACTS

RELATED APPLICATION (foreign priority claim)

Benefit is claimed of the prior filing date of U.S. provisional application no. 60/570,029, filed May 10, 2004 in accordance with 37 CFR §1.55 and 35 USC §119.

RELATED APPLICATIONS/INCORPORATION BY REFERENCE

All documents cited or referenced herein ("herein cited documents"), and all documents cited or referenced in the herein cited documents, together with any manufacturer's instructions, descriptions, product specifications, and product sheets for any products mentioned herein or in any document incorporated by reference herein, are all hereby incorporated herein by reference, and may be employed in the practice of the invention.

FIELD OF THE INVENTION

This invention relates to processes or methods for the production of compositions comprising extracts of black beans containing phenolics, such as polyphenols, flavonoids, and tannins, phytosterols, and triterpenoids such as saponins and other natural products with proven antioxidant capacity, colorant capacity, and uses thereof, e.g., as antioxidants, nutritional supplements, as food, cosmetic or pharmaceutical antioxidants or colorants, as antineoplastic or anti-cancer or anti-tumor preparations, e.g., to treat, prevent and/or inhibit cancers or cancer cell growth, such as hormone dependent or hormone independent tumors or cancers or cancer cells. such as mammalian mammary, prostate, colon, hepatic, leukemia cancer or cancer cell growth, as active ingredient(s) in compositions for lowering cholesterol or lowering oxidation of LDL or for inhibiting cholesterol synthesis (or the enzyme therefor), as an active ingredient(s) in compositions, e.g., nutritional supplements. for reducing the symptoms of menopause or for calcium absorption in post-menopausal mammalian (e.g., human, animal such as companion animal, e.g., canine) females (as black bean extracts—from hull and/or beans—can have estrogenic activity; feminizing estrogenic activity), or as a strong antioxidant that may prevent chronic diseases such as cirrhosis. The invention also comprehends methods for using the compositions or preparations of the invention, as well as methods for making or formulating compositions or preparations of the invention. The invention also relates to the procedure for obtaining non-glycosidated phenolic-rich extracts by the germination or malting of black beans, an embodiment of the invention which yields extracts with greater properties (e.g., higher concentrations of active compounds) than raw extracts containing glycosides. The invention also relates to a method for obtaining hulls that have a high concentration of active compounds. The term "hulls" in this invention are the outside film of the whole bean after the whole bean is removed from the pod. Anatomically and biologically, legume hulls are named "testa" or "testae". In contrast, "pods" contain the whole bean as in a sack. The invention also related to a process for separating the complex mixture of phytochemicals from the black beans extracts via the use of "Aqueous two-phase systems" (ATPS).

BACKGROUND

Beans are one of the most important crops in Mexico, the annual average intake of common beans is approximately 22 kg/capita (Castellanos et al 1997); interestingly black and pinto beans are the most widely consumed. Furthermore, the inventors found it intriguing that the incidence of mammary cancer is significantly lower in states where women consume black beans in contrast with other states where other types of beans are usually ingested. In 1997, the average death rate of females older than 25 years due to breast cancer was 14.8 per 100,000 females whereas for counterparts living in states where black beans are frequently consumed, the rate was 8.2 (CONAPO, 2004). The inventors suspected that the more than 40% lower risk might be at least partially attributable to consumption of black beans. As occurs in other parts of the world, a higher incidence of breast cancer death occurs in post-menopause females older than 40 years. The highest incidence of deaths due to breast cancer is in geriatric women older than 65 years (42.4/100,000 females). See also Azevedo et al, 2003 (mice fed with black bean diets may have shown a lower incidence of CP-induced DNA damage, but note that the study did NOT use purified compounds or fractions from purifying black bean samples, and employed a comet assay that only detects primary DNA lesions, which might or might not be converted into mutations, thus providing nothing more to the art than the anecdotal observations in CONAPO, 2004).

Several phenolic compounds have been reported from *Phaseolus vulgaris*, most of them phytoalexins isolated from fungal infected beans (Burden 1972, Perrin 1972, Kim, 1988, Beninger et al. 1998, Beninger et al. 1999). Likewise, other phenolics with potential nutraceutical properties have also been extracted from healthy black beans. Tannins may contribute at least 4% of the composition of the hulls and this percentage increases according to variety and/or storage conditions. Cardador-Martinez et al (2002) found that most of the phenolics and antioxidants in common beans were concentrated in the hulls or testas and that these antioxidants had free radical scavenging activity with antimutagenic activity. Different flavonoids are involved in the seed color of beans, in particular anthocyanins, which may account for 2.5% of the seed coat. The level of anthocyanins in black beans (at least 200 mg/100 g beans) is comparable to that reported in fruits such as berries (Takeoka et al 1997). Compounds that may have been previously identified have not been shown to have the utilities set forth herein.

Anthocyanins like other flavonoids seem to play an important role in the prevention of human diseases associated with oxidative stress. These properties have been attributed to their high antioxidant activity that ranges from 6-42% of the radicals scavenged using the DPPH (1,1-diphenyl-2-picrylhydrazyl) method, a value that is greatly affected by the presence of sugars bound to the molecules. Bound sugars diminish the antioxidant activity of flavonoids (Kähkönen and Heinonen, 2003). The anthocyanin literature does not disclose or suggest black bean and/or hull thereof extracts, compounds thereof, and uses thereof as herein set forth.

Another group of flavonoids previously reported in the literature are the isoflavones, which possess estrogenic and other biological activities. These compounds are considered to be non-nutritive; however, interest in these compounds has arisen because of their beneficial or nutraceutical effects (Setchel and Cassidy 1999). Tabor, U.S. Pat. No. 6,482,448 and Kelly, U.S. Pat. No. 6,497,906, involve formulations or supplements obtained from soybeans containing isoflavones daidzein, genistein, formononetin, biochanin A and glycitein, in different ratios and concentrations, to treat or prevent pre-menopausal symptoms, heart/cardiovascular related conditions, osteoporosis, breast/prostate cancers, endometrium abnormalities and head/brain symptoms including Alzheimer's Disease. There is no teaching or suggestion in such literature and patents of extracts from black beans and/or hulls thereof, compounds thereof, and the utilities therefore as herein disclosed.

Many natural compounds, such as flavonoids and saponins, occur mainly in their glycoside forms; the basic structure is substituted with at least one molecule of simple sugars such as glucose, galactose, arabinose, rhamnose and xylose. Removal of the bound sugars via fermentation or glycosidic enzymes yields extracts with higher bioactivity because the resulting aglycones have more affinity for cell receptors. Several U.S. Patents involve methods for preparing aglycone isoflavones enriched products (U.S. Pat. Nos. 6,579,561, 6,500,965, 6,146,668, 5,320,949; 5,352,384; 5,637,561 and 5,637,562). Izumi et al (2000) investigated the difference in the absorption of soy isoflavones aglycones and glycosides in humans and found that a higher plasma concentration was observed after aglycone intake (more than two times greater) than the levels observed after glucoside ingestion. Setchell et al (2001) determined that aglycones genistein and daidzein attained peak plasma concentration faster than their corresponding glycosides. U.S. Pat. No. 6,607,757 involves a soybean (*Glycine max*) extract having isoflavones and saponins to treat postmenopausal symptoms and breast and prostate cancer. Hendler et al., U.S. Pat. No. 6,541,613 involves a modification by esterification of isoflavones to promote bioavailability and enhance hydrosolubility. The esterified isoflavones may be employed therapeutically or prophylactically for a variety of conditions. These articles and patents do not disclose or suggest black bean and/or hull thereof extracts, compounds therefrom, and uses thereof as herein disclosed.

Thurn and Huang, U.S. Pat. No. 6,004,558 involves the preparation of therapeutic compositions comprising extracts of red clover (*Tribolium* sp) or soybeans from which the isoflavones were removed and nevertheless the therapeutic use of these extracts were effective to treat or prevent a variety of cancers. Therefore other types of flavonoids and/or phenolic compounds and/or triterpenes and/or other natural compounds are also useful to treat cancer. For example, Prochaska et al (U.S. Pat. No. 5,336,685) involves a method of inhibiting the growth of multidrug resistant cancer cells with flavonoids such as alpha and beta naphthoflavones, flavone, and 2,3 dihydroflavone. Buchholz et al., U.S. Pat. No. 6,514,527, involves a composition containing a mixture of bioflavonols isoqueracetin, queracetin 4-glycoside, rutin and quercetin possessing antioxidant and preventive properties against damage to human tissues and cardiovascular disease. On the other hand, Romancyzk et al., U.S. Pat. Nos. 6,562,863 and 6,479,539 pertains to cocoa (*Theobroma cacao*) extracts rich in polyphenols or procyanidins for use as antioxidant and antineoplastic agents. Recently, Bawadi et al (2005) demostrated that condensed tannins isolated from black beans did not interfere with the proliferation of normal human fibroblast lung cells, but inhibited the growth of Caco-2 colon, MCF-7 and Hs578T breast, and DU 145 prostatic cancer cells by disrupting the cells. Interestingly, they found that ATP levels were reduced in tannin-treated cancer cells, which implies reduced cell proliferation and migration activity, and gross morphological examination of tannin-treated cells suggested that cell death occurred by apoptosis. Morre et al (U.S. Pat. No. 6,410,061) involves extracts based on catechins obtained from green tea (*Camellia sinensis*) to treat cancers or solid tumors. Composition of catechins includes epigallocatechin gallate, epicatechin, epicatechin gallate and epigallocatechin. Epigallocatechin gallate, the major catechin found in green tea, blocks DNA transcription of a number of genes in cancer cell lines and therefore acted as anti-carcinogenic. These patents do not disclose or suggest black bean and/or hull thereof extracts, compounds therefrom, and uses thereof as herein disclosed.

As mentioned, most phenolic compounds found in black beans are concentrated in the testa (Cardador-Martinez et al, 2002). Sosulski and Dabrowski (1984) found that dehulling substantially reduced phenolic composition of pigeon pea, faba bean, mungo bean and lentils but had little effect on the phenolic composition of field pea, navy bean, lima bean or chickpea. Ronzio et al., U.S. Pat. No. 5,762,936 involves the preparation of extracts of seed coats of lentil (*Lens esculenta*) rich in condensed tannins, flavanones, flavanols, and phenolic acids that have the ability to quench free radicals and inhibit certain cells responsible for inflammation. The present inventors found no literature providing bioactivity in black bean hulls. But Grabiel et al. in a recently published U.S. Patent Application 20040131749A1 describes the potential use of phytochemicals, in particular polyphenolics extracted from beans that naturally are rich in anthocyanins, flavonols, proanthocyanidins, isoflavones, saponins, sapogenins, lectines, vitamins, minerals and functional proteins. They propose a method where edible beans and an aqueous extract are obtained, this last one a potential significant source of flavonols and anthocyanins that can be separated and used for treatment or reducing the probability of developing cancer, stroke, elevated blood cholesterol, hypertension, myocardial infarction, diabetes, obesity and inflammatory disorders in humans. These documents do not disclose or suggest (or disclose or suggest after the claim for priority of this invention, e.g. Bawadi et al. (2005)) black bean and/or hull thereof extracts, compounds therefrom, and uses thereof as herein disclosed; and, do not disclose or suggest the method for dehulling of the instant invention or the use of hulls as herein disclosed.

Thus, none of the scientific reports or patents sets forth or claims the production and utilization of black bean and/or hull thereof extracts, compounds therefrom, and the uses thereof disclosed herein, or the use of germination to increase the bioactivity of the compounds in black bean and/or hulls thereof as herein disclosed. Nor does the art particularly teach toward the use of black bean and/or hull extracts as the generous source of especially useful compounds which the inventors discovered in the present invention.

OBJECTS AND/OR SUMMARY OF THE INVENTION

The invention involves novel compounds and compositions from extracts of black beans and/or hulls thereof and uses thereof, including methods for increasing active compounds in black beans and/or hulls thereof, and methods for obtaining hulls suitable for use in the invention. The use of extracts from black beans and/or hulls thereof provides a hitherto untapped source of active ingredients that can be prepared and used, e.g., administered advantageously in various ways, including combating cancers. This description will assist in understanding the present invention and how it goes beyond the prior knowledge hitherto.

There may be potential synergistic effects of different types of phenolic compounds in black bean and/or hull thereof extracts, e.g., to inhibit cancer cells, to provide an antioxidant effect, to provide a colorants effect, in lowering cholesterol or lowering oxidation of LDL (low density lipoproteins, plasma low density lipoproteins), in inhibiting cholesterol synthesis (or the enzyme therefor, e.g., 3-hydroxy-3-methylglutaryl coenzyme A reductase or HMG CoA, the first rate limiting enzyme in the chain of cholesterol synthesis from 3 acetyl CoA molecules), in reducing or preventing liver fibrosis, or in reducing the symptoms of menopause (e.g., hot flashes, vaginal drying, sleep disorders, e.g., due to hot flashes, depression, irritability, osteoporosis, cardiovascular disease) or in calcium absorption in post-menopausal mammalian (e.g., human, animal such as companion animal, e.g., canine) females (as black bean extracts—from hull and/or beans—can have estrogenic activity; feminizing estrogenic activity). Accordingly, the invention envisions the use of extracts, compounds thereof, and combinations of such compounds, alone or in combination with other known and effective nutraceutical compounds such as vitamins A,C,E, and/or selenium sources.

The invention provides processes or methods for the production of compositions comprising extracts of black beans and/or hulls thereof containing phytochemicals such as phenolics (polyphenols, flavonoids, tannins and related compounds), triterpenes such as saponins, and phytosterols with antioxidant capacity, colorant capacity, and uses thereof, e.g., as antioxidants, nutritional supplements, as food, cosmetic or pharmaceutical antioxidants or colorants, as antineoplastic or anti-cancer or anti-tumor preparations, e.g., to treat, prevent and/or inhibit cancers or cancer cell growth, such as hormone dependent or hormone independent tumors or cancers or cancer cells, such as one or more of mammalian mammary, prostate, colon, hepatic, leukemia (e.g., one or more of myelocytic or myelogenous or lymphocytic) cancer or cancer cell growth, as active ingredient(s) in compositions for lowering cholesterol or lowering oxidation of LDL (low density lipoproteins, e.g., plasma low density lipoproteins) or for inhibiting cholesterol synthesis (or the enzyme therefor, e.g., 3-hydroxy-3-methylglutaryl coenzyme A reductase or HMG coA, the first rate limiting enzyme in the chain of cholesterol synthesis from 3 acetyl-CoA molecules), or reducing or preventing liver fibrosis, as an active ingredient(s) in compositions, e.g., nutritional supplements, for reducing the symptoms of menopause (e.g., one or more of hot flashes, vaginal drying, sleep disorders, e.g., due to hot flashes, depression, irritability, osteoporosis, cardiovascular disease) or for calcium absorption in post-menopausal mammalian (e.g., human, animal such as companion animal, e.g., canine) females (as black bean extracts—from hull and/or beans—can have estrogenic activity; feminizing estrogenic activity).

The invention also provides methods for using the compositions or preparations of the invention, as well as methods for making or formulating compositions or preparations of the invention. The invention also provides a procedure for obtaining non-glycosidated phenolic-rich extracts by the germination or malting of black beans, an embodiment of the invention which yields extracts with greater properties (e.g., higher concentrations of active compounds) than raw extracts containing glycosides . The invention further provides to a method for obtaining hulls that have a high concentration of active compounds. Accordingly, while the invention need not have any particular object, and objects herein mentioned are suggested, and not mandatory, an object of the present invention can be to provide black bean (*Phaseoulus vulgaris*) extracts from the whole grain of different varieties. Another object of the present invention can be to advantageously provide black bean extracts from seed coats or hulls of different varieties. A further object of the present invention can be to provide black bean extracts from cooked whole grains. Another object of the present invention can be to provide black bean extracts from malted, sprouted or germinated whole grains and/or their hulls. A yet further object of the invention can be to provide methods to produce black bean extracts. A still further object of the invention can be to provide methods to fractionate black bean extracts. An even further object of the invention can be to provide an antioxidant composition from black beans. It is another object of the invention to provide black bean and/or hull extracts or compounds therefrom, either individually or in combination, that: inhibit cancer cell growth, prevent cancer and/or, lower cholesterol or lower oxidation of LDL (low density lipoproteins, e.g., plasma low density lipoproteins) and/or, inhibit cholesterol synthesis (or the enzyme therefor, e.g., 3-hydroxy-3-methylglutaryl coenzyme A reductase or HMG CoA, the first rate limiting enzyme in the chain of cholesterol synthesis from 3 acetyl-CoA molecules) and/or, reduce liver fibrosis reduce the symptoms of menopause (e.g., one or more of hot flashes, vaginal drying, sleep disorders, e.g., due to hot flashes, depression, irritability, osteoporosis, cardiovascular disease) and/or stimulate calcium absorption, e.g., in post-menopausal mammalian (e.g., human, animal such as companion animal, e.g., canine) females and/or, can have estrogenic activity; e.g., feminizing estrogenic activity and/or, are antioxidants, e.g., as an active ingredient in a nutritional supplement, and/or, are food, cosmetic or pharmaceutical antioxidants or colorants and/or, can be an active ingredient in an antineoplastic or anti-cancer or anti-tumor preparations, e.g., to treat, prevent and/or inhibit cancers or cancer cell growth, such as hormone dependent or hormone independent tumors or cancers or cancer cells, such as one or more of mammalian mammary, prostate, colon, hepatic, leukemia (e.g., one or more of myelocytic or myelogenous or lymphocytic) cancer or cancer cell growth, and/or, can be an active ingredient in compositions for lowering cholesterol or lowering oxidation of LDL (low density lipoproteins, e.g., plasma low density lipoproteins), e.g., nutritional supplement or over the counter preparation or prescription preparation and/or, can be an active ingredient in compositions for inhibiting cholesterol synthesis (or the enzyme therefor, e.g., 3-hydroxy-3-methylglutaryl coenzyme A reductase or HMG CoA, the first rate limiting enzyme in the chain of cholesterol synthesis from 3 acetyl-CoA molecules), e.g., nutritional supplement or over the counter preparation or prescription preparation, and/or, can be an active ingredient(s) in compositions, e.g., nutritional supplement or over the counter preparation or prescription preparation, for reducing the symptoms of menopause (e.g., one or more of hot flashes, vaginal drying, sleep disorders, e.g., due to hot flashes, depression, irritability, osteoporosis, cardiovascular disease) and/or, can be an active ingredient in a composition, e.g., nutritional supplement or over the counter preparation or prescription preparation, for stimulating calcium absorption, e.g., in post-menopausal mammalian (e.g., human, animal such as companion animal, e.g., canine) females, and/or, can be an active ingredient in a composition, e.g., nutritional supplement or over the counter preparation or prescription preparation providing estrogenic activity; e.g., feminizing estrogenic activity. A yet further object of the invention can be to identify natural compounds with proven bioactivity that can be synthesized. And an even further object of the invention can be to provide methods for making anti-cancer and anti-tumor black bean and/or hull extract compositions.

In view of the epidemiological evidence (Castellanos et al. 1997, CONAPO 2004, and Azevedo et al., 2003) and the bioactivity of black bean extracts, the consumption of black beans as part of the normal diet or as a dietary supplement as extracts or compounds of the present invention can have a beneficial preventive effect against cancer in humans and mammals. Thus, it is a further object of this invention to provide such a preventive effect against cancer in humans and mammals in an advantageous manner. For example, a dietary practitioner may adapt a preventive therapy by means of the principles of nutrition with the methods, compositions and extracts of the present invention. The present invention thus provides black bean and/or hull extracts from malted, sprouted or germinated whole grains and/or their hulls. The invention also provides methods to produce black bean extracts, e.g., via organic extraction, such as water or by a lower alkyl, e.g., $C_1$-$C_6$ alcohol, ether, ketone, aldehyde extraction, for instance, water, methanol, ethanol, acetone, ethyl ether, or ethyl acetate extraction; optionally followed advantageously by a separation, e.g., chromatography, such as column chromatography, e.g., C-18 column chromatography, for instance, to remove water soluble phenolic compounds and thereby provide flavonoids, optionally further followed by separation of individual compounds.

Accordingly, the invention provides methods to fractionate black bean and/or hull extracts. The invention even further provides an antioxidant composition from black beans and/or hulls thereof. Even further still, the invention provides black bean and/or hull extracts or compounds therefrom, either individually or in combination, that: inhibit cancer cell growth, prevent cancer and/or, lower cholesterol or lower oxidation of LDL (low density lipoproteins, e.g., plasma low density lipoproteins) and/or, inhibit cholesterol synthesis (or the enzyme therefor, e.g., 3-hydroxy-3-methylglutaryl coenzyme A reductase or HMG CoA, the first rate limiting enzyme in the chain of cholesterol synthesis from 3 acetyl-CoA molecules) and/or, reduce liver fibrosis, reduce the symptoms of menopause (e.g., one or more of hot flashes, vaginal drying, sleep disorders, e.g., due to hot flashes, depression, irritability, osteoporosis, cardiovascular disease) and/or stimulate calcium absorption, e.g., in post-menopausal mammalian (e.g., human, animal such as companion animal, e.g., canine) females and/or, can have estrogenic activity; e.g., feminizing estrogenic activity and/or, are antioxidants, e.g., as an active ingredient in a nutritional supplement, and/or, are food, cosmetic or pharmaceutical antioxidants or colorants and/or, can be an active ingredient in an antineoplastic or anti-cancer or anti-tumor preparations, e.g., to treat, prevent and/or inhibit cancers or cancer cell growth, such as hormone dependent or hormone independent tumors or cancers or cancer cells, such as one or more of mammalian mammary, prostate, colon, hepatic, leukemia (e.g., one or more of myelocytic or myelogenous or lymphocytic) cancer or cancer cell growth, and/or, can be an active ingredient in compositions for lowering cholesterol or lowering oxidation of LDL (low density lipoproteins, e.g., plasma low density lipoproteins), e.g., nutritional supplement or over the counter preparation or prescription preparation and/or, can be an active ingredient in compositions for inhibiting cholesterol synthesis (or the enzyme therefor, e.g., 3-hydroxy-3-methylglutaryl coenzyme A reductase or HMG CoA , the first rate limiting enzyme in the chain of cholesterol synthesis from 3 acetyl-CoA molecules), e.g., nutritional supplement or over the counter preparation or prescription preparation, and/or, can be an active ingredient(s) in compositions, e.g., nutritional supplement or over the counter preparation or prescription preparation, for reducing the symptoms of menopause (e.g., one or more of hot flashes, vaginal drying, sleep disorders, e.g., due to hot flashes, depression, irritability, osteoporosis, cardiovascular disease) and/or, can be an active ingredient in a composition, e.g., nutritional supplement or over the counter preparation or prescription preparation, for stimulating calcium absorption, e.g., in post-menopausal mammalian (e.g., human, animal such as companion animal, e.g., canine) females, and/or, can be an active ingredient in a composition, e.g., nutritional supplement or over the counter preparation or prescription preparation providing estrogenic activity; e.g., feminizing estrogenic activity.

The invention accordingly comprehends compositions comprising or consisting essentially of black bean and/or hull extracts or compounds therefrom, either individually or in combination, e.g., for any of the foregoing extracts or compounds described above; as well as methods for using black bean and/or hull extracts or compounds therefrom, either individually or in combination, e.g., administering black bean and/or hull extracts or compounds therefrom, either individually or in combination, in an effective amount for any of the foregoing extracts or compounds described above and/or contacting a food, pharmaceutical or cosmetic with black bean and/or hull extracts or compounds therefrom, either individually or in combination, in an amount effective, e.g., for colorant and/or antioxidant effect. And the invention comprehends methods for preparing such compositions, e.g., admixing a suitable carrier, diluent or excipient, e.g., a pharmaceutically or veterinarily acceptable carrier or diluent, with black bean and/or hull extracts or compounds therefrom, either individually or in combination, whereby the composition contains an amount effective for any of the foregoing extracts or compounds described above.

The invention even further provides a method to identify natural compounds with proven bioactivity that can be synthesized. The invention further provides a method to enrich or enhance the active compounds in a black bean or hull thereof extract comprising germinating the black bean prior to extraction. The invention also provides a method for obtaining dry bean hulls, advantageously dry black bean hulls, comprising dehulling, aspirating dehulled beans to obtain aspirated hulls and remains thereof, sieving the remains to obtain hull fines and cotyldedons, combining the aspirated hulls and hull fines, and drying the combined aspirated hulls and hull fines to obtain dry bean hulls, advantageously dry black bean hulls. The dry black bean hulls are useful for obtaining extracts that are useful in the practice of the invention. The invention further provides partially purified solvent derived black bean (*Phaseouls vulgaris* L) extracts comprising triterpenes, such as saponins, phytosterols, total phenolics, such as polyphenols, flavonoids and tannins with high anti oxidant capacity. The extracts of claim can be obtained from black bean hulls or seed coats. The extracts can be obtained from malted, germinated or sprouts of black beans. The extracts can be obtained from fermented black beans. The extracts can be obtained from black beans treated with enzymes or acid hydrolysis with the aim of increasing the amount of aglycone-flavonoids and/or saponins. The extracts can be partially or completely purified by chromatography and/or other physical and/or chemical and/or bioseparation methods. The extracts can be fractionated via high-pressure liquid chromatography. The high-pressure liquid chromatography can be reverse and/or normal high-pressure liquid chromatography. The high-pressure liquid chromatography can be preparative high-pressure liquid chromatography. The extracts can be fractionated via Sephadex.

The extracts can be obtained or fractionated via supercritical $CO_2$.

The extracts can be in a dry form or in liquid form or in freeze-dried or lyophilized form.

The solvent can be water, acetone, methanol, ethyl acetate, ethanol, or a combination thereof. The water can be pure or distilled.

The extracts can be admixed with one or more pharmaceutically or veterinarily acceptable carriers, excipients and/or diluents. And hence, the invention comprehends compositions comprising the extracts.

The invention further contemplates isolated or purified compounds obtained from black beans or hulls thereof. These compounds are useful alone or in combination in different concentrations. The compounds can be synthetically obtained, as well as modified by different means including combinatorial chemistry.

The invention also contemplates a process for separating the complex mixture of phytochemicals from the black beans extracts via the use of "Aqueous two-phase systems" (ATPS). Use of ATPS can reduce the amount of solvents required in the extraction process.

The invention thus envisions a substantially pure or partially pure black bean or hull thereof extract containing or consisting essentially of flavonoid(s), or synthetic flavonoid(s) comprising or consisting essentially of flavonoid(s) as in such an extract, and uses thereof, and compositions consisting essentially of or containing such an extract or synthetic flavonoid(s).

Compositions containing the inventive black bean and/or hull extract(s), e.g., flavonoid(s) can be prepared in accordance with standard techniques well known to those skilled in the pharmaceutical or veterinary or food or cosmetic arts.

Unless otherwise defined, all technical and scientific terms used herein have the same meaning as commonly understood by one of ordinary skill in the art to which this invention belongs. Although methods and materials similar or equivalent to those described herein can be used in the practice or testing of the present invention, suitable methods and materials are described below. All publications, patent applications, patents, and other references mentioned herein are incorporated by reference in their entirety. In the case of conflict, the present specification, including definitions, will control. In addition, the materials, methods, and examples are illustrative only and not intended to be limiting.

It is noted that in this disclosure and particularly in the claims, terms such as "comprises", "comprised", "comprising" and the like can have the meaning attributed to it in U.S. Patent law; e.g., they can mean "includes", "included", "including", and the like; and that terms such as "consisting essentially of" and "consists essentially of" have the meaning ascribed to them in U.S. Patent law, e.g., they allow for elements not explicitly recited, but exclude elements that are found in the prior art or that affect a basic or novel characteristic of the invention. Indeed, it is desired that claims not read upon the prior art and "consisting essentially of" and "consists essentially of" are envisioned to be used to avoid claims from reading that which may be in the art.

These and other objects, features, and advantages of the invention become further apparent in the following detailed description of the invention when taken in conjunction with the accompanying drawings that illustrate, by way of example, the principles of this invention.

BRIEF DESCRIPTION OF THE DRAWINGS

The following Detailed Description, given to describe the invention by way of example, but not intended to limit the invention to specific embodiments described, may be understood in conjunction with the accompanying FIGS. incorporated herein by reference, in which:

FIG. 1. shows total phenolic content expressed as catechin equivalents of 12 different types of black beans: 1=Mex 332, 2=NG-Coaxtla 91, 3=NG-8025, 4=NG-San Luis, 5=NG Altiplano, 6=NG-150, 7=NG-Sahuatoba, 8=NG Tacana, 9=NG-Viscaya, 10=Negro Otomi, 11=NG-Perla, 12=NG-INIFAP. Asterisk (*) denotes that total phenolics content was calculated as catechin equivalents (mg) per gram of dried black bean.

FIG. 2. shows a comparison of flavonoids that absorbed at 262 nm from extracts of soybean (Chromatogram 2A) and NG-Perla black bean variety (Chromatogram 2B) determined via HPLC-UV. Labelled peaks include: from Chromatogram 2A: 1 -diadzin, 2 -glycitin, 3 - genistin, from Chromatogram 2B: 10 -diadzin, 11 -compound with the same retention time of genistin; 12 -unidentified compound A; 13 -unidentified compound B.

FIG. 3. shows flavonoids types and concentrations of different varieties of black beans and soybeans quantified by HPLC-UV at 262 nm. Asterisk (*) denotes that flavanoid content was calculated as genistin eciuivalents (μg) per ml of the black bean extract in 100% methanol obtained after a $C_{18}$ separation. Key to black bean varieties: 1=Mex 332, 2=NG-Coaxtla 91, 3=NG-8025, 4=NG-San Luis, 5=NG Altiplano, 6=NG-150, 7=NG-Sahuatoba, 8=NG Tacana, 9=NG-Viscaya, 10=Negro Otomi, 11=NG-Perla, 12=NG-INIFAP.

FIG. 3a. shows the chemical structure of Phaseoloside E. Chemical formula is (12,15-Oleanadiene-3,23-diol 3-O-[β-D-Glucopyranosyl-(1→4)-β-D-glucopyranosyl-(1→4)-α-D-galactopyranosyl-(1→2)[α-L-rhamnopyranosyl-(1→6)]-β-D-glucopyranosyl-(1→4)-α-D-galactopyranosyl-(1→2)-α-L-arabinopyranosyl-(1→3)-β-D-glucuronoside].

FIG. 4a. shows HPLC-PDA chromatograms (262nm) and their corresponding Peak Spectra of NG-Perla black bean extracts "second fraction" treated without (Chromatogram 4A) acid hydrolysis. (Note:.

FIG. 4b. shows HPLC-PDA chromatograms (262nm) and their corresponding Peak Spectra of NG-Perla black bean extracts "second fraction" treated with (Chromatogram 4B) acid hydrolysis.

FIG. 5. shows concentration of anthocyanins deiphinidin, petudin and malvidin in the "second fraction" of 12 different black bean varieties: 1=Mex 332, 2=NG-Coaxtla 91, 3=NG-8025, 4=NG-San Luis, 5=NG-Altiplano, 6=NG-150, 7=NG-Sahuatoba, 8=NG Tacana, 9=NG-Viscaya, 10=Negro Otomi, 11=NG-Perla, 12=NG-INIFAP. Asterisk (*) denotes that anthocyanin content was calculated as μg of the corresponding anthocyanin per mL of the black bean extract in 100% methanol obtained after a $C_{18}$ separation.

FIG. 6a. shows a milling procedure to obtain seed coats or hulls from black beans.

FIG. 6b. shows a milling procedure with an initial drying step to obtain seed coats or hulls from black beans.

FIG. 7. shows a comparison of total phenolics from black bean hulls extracts obtained from water, 96% ethanol, 80% methanol and 70% acetone.

FIG. 8. shows Trolox equivalents (μM/μM of total phenolics) obtained by the ORAC method from raw extracts (acetone) of black bean varieties NG-Perla and Mex 332 hulls that were further purified with ether and fractionated with methanol and ethyl acetate.

FIG. 9. shows a chromatogram of an extract of flavonoids from 1 day germinated black bean variety NG-Perla obtained by HPLC-PDA at 262 nm with corresponding spectrums of the major peaks.

Peaks 110 and 114: Unknown isoflavones from 1 day germinated black bean extract.

Peak 111: Unknown flavonoid from 1 day germinated black bean extract.

Peaks 112 and 113: Remnants of flavonols present in raw black beans (see peaks 42 and 43 of FIG. 4A)

Note: UV absorption spectrums of the labeled compounds are shown above chromatogram.

FIG. 10. shows the effect of different bean:water ratios on flavonoid loss from beans into the soaking water.

FIG. 11A, 11B. shows the effect of germination time on the concentration of flavonoids for the NG-Perla black bean variety previously soaked with a bean:water weight ratios of 1:3 (FIG. 11A) and 1:6 (FIG. 11B).

FIG. 12. shows the effect of genistein concentration on in vitro mammary cancer cell (MCF-7) proliferation.

FIG. 13. shows a comparison between inhibitory effects of genistin and genistein on in vitro mammary cancer cell (MCF-7) proliferation.

FIG. 14. shows a comparison between raw and germinated black bean extracts and genistein on inhibition of mammary cancer cell (MCF-7) growth cultured in vitro.

FIG. 15. shows percent in vitro cell proliferation of HepG$_2$ exerted by 6 black bean extracts: V1=Mex 332; V4=NG-San Luis; V6=NG-150; V8=NG-Tacana;V11=NG-Perla and V12=NG-INIFAP.

FIG. 16 shows the median decrease time (days) after administration of DMBA in Wistar rats that did not resist the induction (death before 84 days post-DMBA administration); a=control diet, b=low level of germinated black bean meal, c=high level of germinated black bean meal, d=low level of germinated black bean meal phenolics extract.

FIG. 17 shows the median number of tumors 84 days after cancer induction by DMBA in surviving Wistar rats and fed with 5 different diets: a=Control diet; b=Low level of germinated black bean meal: c=High level of germinated black bean meal; d=Low level of genninated black bean meal phenolics extract; and e=High level of germinated black bean meal phenolics extract.

FIG. 18 Analysis of number of tumors after 84 days of DMBA cancer induction by treatment consisting in diet for all Wistar rats tested: a (control with no meal nor phenolic extract from germinated black bean); b (low level of germinated black bean meal); c (high level of germinated black bean meal); d (low level of germinated black bean phenolics extract); and e (high level of germinated black bean phenolics extract).

FIG. 19 shows a separation scheme to obtain different concentrations and types of phenolics and other phytochemicals.

FIG. 20 shows the content of the different fractions obtained from the separation scheme of FIG. 19.

FIG. 21 compares the effect against in vitro growth of MCF-7 mammary cancer cells of the LE fraction of FIG. 19 with Taxol®.

FIG. 22 shows the chemical structure of compounds with similar UV-vis absorption as the unknown compounds of the LE fraction.

FIG. 23a shows the tumor growth rate in Wistar rats administered extracts from raw black bean hulls. Tumor growth rate (cm/day) observed in experimental units administered with 25% DMSO with no extract, raw black bean hulls freeze-dried or semi-purified extract (treatments C, R or A from example 13) during 7 weeks and 10 weeks after cancer induction with DMBA.

FIG. 23b shows tumor growth in Wistar rats of different concentrations of freeze-dried 80% methanol black bean extract re-suspended in distilled water and administered intragastrically to Wistar rats presenting tumors induced with DMBA.

FIG. 23c shows change of tumor diameter when 0, 4 or 35 mg of freeze-dried 80% methanolic extract of black bean hulls resuspended in distilled water are administered intragastrically to Wistar rats presenting tumors induced with DMBA considering the diameter at day 0. (Results are an average of 3 experimental units per treatment).

FIG. 24 shows a comparison of tumor size of tumors extracted from Wistar rats with mammary cancer DMBA induced and administered with raw freeze-dried black bean hulls 80% methanolic extract re-suspended in distilled water at concentrations of 0, 35, 18, 9 and 4 mg/ml (B, 1, 2, 3 and 4, respectively).

FIG. 25 shows an example of an aqueous-two phase system for the separation of phytochemicals from black bean.

DETAILED DESCRIPTION

Although the related prior published documents indicated that extracts rich in phenolics, anthocyanins, flavonoids, isoflavones and/or tannins had antiproliferative activity against cancer cells, the inventors discovered that the activity of black bean extracts was unexpectedly higher than reported from other related sources. This surprising activity might be due to unique types of flavonoids that have not been previously noticed as anti-carcinogens. Black bean extracts obtained after treatment with at least one polar solvent, were discovered to be unexpectedly rich in phenolics, anthocyanins, flavonoids, isoflavones and tannins. Furthermore, screening variety tests showed that certain black bean types were more promising sources of active compounds than the prior art had in general shown.

In one embodiment of the invention, the black beans extracted are those which belong to *Phaseolus vulgaris*. In another embodiment of the invention, the genotypes of *Phaseolus vulgaris* used are Mex 332, NG-Coaxtla 91, NG-8025, NG-San Luis, NG Altiplano, NG-150, NG-Sahuatoba; NG Tacana, NG-Viscaya, Negro Otomi, NG Perla and NG-INIFAP. In another embodiment of the invention, the black beans are allowed to germinate prior to undergoing the extraction process.

In one embodiment of the invention, the extraction steps comprises milling of the whole black bean (i.e. the hull and the internal mass) until an average particle size is within the range of about U.S. mesh #20-150 (particle diameter size of about 100 μm to about 850 μm) is achieved. In another embodiment of the invention the average particle size is within the range of about U.S. mesh #60 to about #100 (particle diameter size of about 150 μm to about 250 μm). In yet another embodiment of the invention the average particle size is within the range of about U.S. mesh #40 to about #100 (particle diameter size of about 150 μm to about 420 μm).

The milled whole black bean is then extracted with at least one polar solvent. In one embodiment of the invention, the polar solvent is selected from the group consisting of $C_6$-$C_{10}$ heteroaryl, $C_1$-$C_6$-alcohol, $C_1$-$C_6$-aldehyde, $C_1$-$C_6$-mines, $C_1$-$C_6$-ketones, $C_2$-$C_6$ esters, $C_2$-$C_6$-ethers and mixtures thereof. In another embodiment of the invention, the solvent is selected from the group consisting of acetone, ethanol, methanol, water and mixtures thereof. In yet another embodiment of the invention, the solvent is a mixture of methanol and water. The milled black bean can be extracted with non-polar solvents to remove impurities, but the active components for the purposes of this invention reside in the polar solvent. The polar solvent black bean extract is the active component which provides for the treatment, prevention and inhibition of cancer, lowering of cholesterol, reduce the symptoms of menopause or provide anti-oxidant or colorant effect. The use of at least one polar solvent for extraction also applies to individual components of the black bean, i.e. the hull and the internal mass as well as germinated black beans.

In a further embodiment, more than one extraction with a polar solvent is performed wherein each of the extractions is performed with a different polar solvent. In one embodiment of the invention, the total extraction comprises an extraction with an aqueous ketone or aqueous alcohol in a first extraction step; followed by a second extraction step with a different alcohol than that used in the first extraction step; and is followed by a final extraction step which uses an alcohol and an ester wherein the alcohol is different that the alcohol used in the first two steps.

In one embodiment of the invention, the total phenolic content of the extract from milled whole black bean is at least about 1.5 mg/g expressed as catechin weight equivalents. In another embodiment of the invention, the total phenolic content is about 1.5 mg/g to about 4.5 mg/g expressed as catechin weight equivalents. In yet another embodiment of the invention, the total phenolic content is about 3.5 mg/g to about 4.5 mg/g expressed as catechin weight equivalents.

In one embodiment of the invention the extract can be further separated and purified via chromatographic means such preparative TLC, column chromatography, liquid chromatography and supercritical liquid chromatography. In another embodiment of the invention, high pressure liquid chromatography (HPLC) is employed.

Use of chromatographic means results in a first fraction which contains little to no flavonols, flavones or isoflavones and a second fraction which contains flavonoids and anthocyanins. The amount of genistin as one of the flavanoids in the extract is present in an amount which is at least about 9 times less in ppm than the amount of genistin in soybeans exposed to the same extraction conditions. In another embodiment of the invention, the amount of genisitin is about 9 to about 30 times less in ppm than the amount of genistin in soybeans exposed to the same extraction conditions. In yet another embodiment of the invention, the amount of genisitin is about 9 to about 20 times less in ppm than the amount of genistin in soybeans exposed to the same extraction conditions.

The anthocyanins in the second fraction from the chromatographic separation of black bean include delphinidin, petunidin and malvidin. In one embodiment of the invention, the concentration of delphinidin ranges from about 5 to 35 ppm, petunidin ranges from about 5 to about 40 ppm and malvidin ranges from about 5 to about 30 ppm. In another embodiment of the invention, the concentration of delphinidin ranges from about 5 to 20 ppm, petunidin ranges from about 5 to about 20 ppm and malvidin ranges from about 5 to about 20 ppm. In yet another embodiment of the invention, the concentration of delphinidin ranges from about 27 ppm, petunidin ranges from about 35 ppm and malvidin ranges from about 35 ppm. (ppm refers to calculation as µg of the corresponding anthocyanin per mL of the black bean extract in 100% methanol after a $C_{18}$ separation)

In another embodiment of the invention, a process for separating the complex mixture of phytochemicals from the black beans extracts via the use of "Aqueous two-phase systems" (ATPS) is described. Use of ATPS can reduce the amount of solvents required in the extraction process (e.g. organic solvent such as methanol, ethyl acetate, butanol, ethanol, ether or mixtures thereof). ATPS has been previously referred in the recovery of biological products of different biological sources (see e.g. Rito-Palomares, M. 2004). It has been established that ATPS form when combinations of hydrophilic solutes (polymers or polymer and certain salts) display incompatibility in aqueous solution above critical concentrations. This technology has several potential advantages, including biocompatibility, ease of scale-up and low cost, etc.

However, it is believed that heretofore no description of the use of ATPS has been applied to the recovery of products from black beans.

ATPS was used to fractionate the complex mixture of phytochemicals from black bean extracts, following a practical approach which exploits the known effect of systems parameters of the solvents and salt solutions, phase volume ratio (Vr; volume of the top phase/volume of the bottom phase), molecular weight of solvent and feedstock concentration upon molecular partition.

Such an approach was used in order to reduce the extent of the empirical experiments necessary to determine the process conditions of the ATPS extraction and reduce the use of organic solvents. All experimental systems used to establish the operating conditions for the ATPS process were prepared for convenience on a fixed mass basis.

Predetermined quantities of stock solutions of a solvent and a salt solution were mixed with the resulting black bean hulls extracts and mixed for a time to ensure adequate homogenization. Adjustment of pH can be accomplished using an appropriate acid or base. The resulting homogenized mixture of ATPS and black bean extract is then allowed to settle and achieve phase separation. Phase separation can be accelerated by standard means in the art, e.g. via centrifugation. The volumes of the phases were used to estimate the volume ratio (Vr)., Samples were carefully extracted from the phases (top phase, bottom phase and interface) and diluted for chemical analysis. The systems tie-line length (TLL), which represents the length of the line that connects the composition of the top and bottom phase of a defined ATPS, was calculated as described by Rito-Palomares (2004).

Smaller molecular weight compound would be expected to be present in the bottom salt-rich phase. Glycosidic flavonols, anthocyanins, and tannins would be expected to be present in the upper solvent phase. Resulting compounds retained in the upper solvent phase can be further separated with the addition of different amounts of salt solutions to form a new ATPS extraction system. Salt and solvent from the bottom and top. phase, respectively, can be removed from the phytochemicals preferably by ultrafiltration and/or reverse osmosis or other operations such as precipitation, dialysis, diafiltration, chromatographic methods and/or supercritical fluid extraction (e.g. using supercritical $CO_2$).

The main advantage of this method is to ease the scaleup of the process by the reduction of solvents used, performing the extraction at room temperature, and the savings of time, labor and equipment. Furthermore, the whole process can be performed in situ using the same agitation tank since for the separation of phases only a short decantation time was required.

The bioactivity of black bean extracts was greatly enhanced when the seed was germinated instead of subjecting the black beans to fermentation processes or to the use of exogenous glycosidic enzymes aimed at increasing the concentration of aglycones. Even more useful to the objective of this invention, the germination produced new types of flavonoids that were not present in raw seeds and that these compounds proved to be more effective against in vitro proliferation of cancer cells.

The black bean hulls surprisingly and unexpectedly contained approximately 20 times more phenolics than whole seeds. In one embodiment of the invention, extracts of black bean hulls have a total phenolic concentration from about 80 to about 300 mg/g, a total flavonoid concentration of from about 20 to about 50 mg/g and a total tannin concentration of from about 10 to about 55 mg/g (mg/g expressed as catechin equivalents on a dry matter basis). In another embodiment of the invention, the total added concentrations of phenolics, flavanoids and tannins is from about 275 mg/g to about 360 mg/g (mg/g expressed as catechin equivalents on a dry matter basis).

Since phytochemicals of interest were mainly present in the hulls and they only represented 7-13% of the seed weight, a mechanical dehulling process was developed. Black beans were pearled or dehulled with the aim of obtaining two fractions: hulls and cotyledons, i.e., the remainder of the whole bean.

In one of the embodiments of this invention, the process of dehulling the black beans begins with a step wherein the black beans are tempered to increase their moisture content from about 8% to about 24% by weight, preferably about 12% to about 20% by weight and more preferably about 16% by weight based on the total weight of the black bean and dehulled mechanically in a grain decorticator equipped with abrasive disks.

In another embodiment of the invention, the decortation time is the time required to remove about 6% to about 16% of the black bean weight. Preferably, the time required is about 8% to about 14% of the black bean weight. Particularly preferably, is the time required to remove about 10% to about 14% of the black bean weight.

In another embodiment of the invention, in the process of dehulling described above, the step of increasing moisture is substituted with a drying step. In one embodiment of the invention, the drying time is between about 6 to about 12 hours at a temperature of about 50° C. to about 70° C. In another embodiment of the invention, the drying time is between about 8 to about 10 hours at a temperature of about 60° C. This process is advantageous over the process which increases moisture content as it requires less processing or decortication time.

The hull rich material is then separated advantageously from the cotyledon-rich material by sieving through a 2 mm diameter sieve, by air aspiration, or other suitable method or device suitable for this purpose. The inventors found that, for the purpose of the present invention, hulls were thus more generally a more effective source material, on an equivalent weight basis, against cancer cell proliferation than whole-seed extracts, but with the understanding that the invention is not limited to hull extracts, as other factors may lead the practitioner to elect another embodiment of the invention as the need may be.

In one embodiment of the invention, the black bean extracts of the invention can be used to treat, prevent or inhibit cancers. In one embodiment of the invention, the black bean extract of the invention show an inhibition rate of MCF-7 mammary cancer cells of about 35% to about 60% relative to a control. In another embodiment of the invention, the black bean extracts of the invention have an $EC_{50}$ against Caco-2 cells of about 100 to about 500 µg/mL and/or the black bean extracts of the invention have an $EC_{50}$ against human liver cancer cells HepG2 of about 500 µg to about 1300 µg.

In another embodiment of the invention, the black bean extract of the invention show a greater percent inhibition of cancer at identical concentrations of Taxol® (paclitaxel) and/or show the same percent inhibition of cancer at lower concentrations relative to Taxol®. In yet another embodiment of the invention, the cancer is breast cancer. In still another embodiment of the invention, the black bean extract concentration shows a greater percent inhibition over the concentration range of about greater than zero to about 0.35 mg/mL.

In one embodiment of the invention, the black bean extracts of the invention also show unexpectedly superior antioxidative effects even against fruits known to be anthocyanin rich. In another embodiment of the invention, black bean hull extracts are disclosed with a total phenol concentration of about 2 to about 6 mM and an antioxidant capacity of about 40 µmol to about 80 µmol Trolox equivalents per gram. In another embodiment of the invention, black bean hull extracts are disclosed with a total phenol concentration of about 3.5 to about 4.5 mM and an antioxidant capacity of about 55 µmol to about 60 µmol Trolox equivalents per gram.

Given the activity and the physical characteristics of the black bean extracts of the invention, these extracts are useful in the pharmaceutical, cosmetic, food and feed industries either as an active ingredient, a nutritional supplement or as a colorant. The black bean extracts are prepared so that they may be administered orally, dermally, parenterally, nasally, ophthalmically, otically, sublingually, rectally or vaginally. Dermal administration includes topical application or transdermal administration. Parenteral administration includes intravenous, intraarticular, intramuscular, and subcutaneous injections, as well as use of infusion techniques. One or more compounds of the invention may be present in association with one or more non-toxic pharmaceutically acceptable ingredients and optionally, other active anti-proliferative agents, to form a composition. These compositions can be prepared by applying known techniques in the art such as those taught in *Remington's Pharmaceutical Sciences*, Mack Publishing Co. (1999) or "*Pharmaceutical Dosage Form and Drug Delivery Systems*" (Sixth Edition), edited by Ansel et al., Williams & Wilkins, (1995), each of which is hereby incorporated by reference. In one embodiment of the invention, the adminstration of the black bean extract is oral.

Commonly used pharmaceutical ingredients which can be used as appropriate to formulate the composition for its intended route of administration include but are not limited to: acidifying agents (examples include but are not limited to acetic acid, citric acid, fumaric acid, hydrochloric acid, nitric acid); alkalinizing agents (examples include but are not limited to ammonia solution, ammonium carbonate, diethanolamine, monoethanolamine, potassium hydroxide, sodium borate, sodium carbonate, sodium hydroxide, triethanolamine, trolamine); adsorbents (examples include but are not limited to powdered cellulose and activated charcoal); aerosol propellants (examples include but are not limited to carbon dioxide, $CCl_2F_2$, $F_2ClC-CClF_2$ and $CClF_3$); air displacement agents (examples include but are not limited to nitrogen and argon); antifungal preservatives (examples include but are not limited to benzoic acid, butylparaben, ethylparaben, methylparaben, propylparaben, sodium benzoate, propionic acids or its salts); antimicrobial preservatives (examples include but are not limited to benzalkonium chloride, benzethonium chloride, benzyl alcohol, cetylpyridinium chloride, chlorobutanol, phenol, phenylethyl alcohol, phenylmercuric nitrate and thimerosal); antioxidants (examples include but are not limited to ascorbic acid, ascorbyl palmitate, butylated hydroxyanisole, butylated hydroxytoluene, hypophosphorus acid, monothioglycerol, propyl gallate, sodium ascorbate, sodium bisulfite, sodium formaldehyde sulfoxylate, sodium metabisulfite, tocopherol, vitamin E); binding materials (examples include but are not limited to block polymers, natural and synthetic rubber, polyacrylates, polyurethanes, silicones and styrene-butadiene copolymers); buffering agents (examples include but are not limited to potassium metaphosphate, potassium phosphate monobasic, sodium acetate, sodium citrate anhydrous and sodium citrate dihydrate); carrying agents (examples include but are not limited to acacia syrup, aromatic syrup, aromatic elixir, cherry syrup, cocoa syrup, orange syrup, syrup, corn oil, mineral oil, peanut oil, sesame oil, bacteriostatic sodium chloride injection and bacteriostatic water for injection); chelating agents (examples include but are not limited to edetate disodium and edetic acid); colorants (examples include but are not limited to FD&C Red No. 3, FD&C Red No. 20, FD&C Yellow No. 6, FD&C Blue No. 2, D&C Green No. 5, D&C Orange No. 5, D&C Red No. 8, caramel, ferric oxide red, natural colorants such as bixin, norbixin, carmine); clarifying agents (examples include but are not limited to bentonite); emulsifying agents (examples include but are not limited to acacia, cetomacrogol, cetyl alcohol, glyceryl monostearate, lecithin, sorbitan monooleate, polyethylene 50 stearate); encapsulating agents (examples include but are not limited to gelatin and cellulose acetate phthalate); fillers (examples include but are not limited to sugars, lactose, sucrose, sorbitol, cellulose preparations, calcium phosphates, natural or synthetic gums, solid starch, starch pastes); flavorants (examples include but are not limited to anise oil, cinnamon oil, cocoa, menthol, orange oil, peppermint oil and vanillin); humectants (examples include but are not limited to glycerin, propylene glycol and sorbitol); levigating agents (examples include but are not limited to mineral oil and glycerin); oils (examples include but are not limited to arachis oil, mineral oil, olive oil, peanut oil, sesame oil and vegetable oil); ointment bases (examples include but are not limited to lanolin, hydrophilic ointment, polyethylene glycol ointment, petrolatum, hydrophilic petrolatum, white ointment, yellow ointment, and rose water ointment); penetration enhancers (transdermal delivery) (examples include but are not limited to monohydroxy or polyhydroxy alcohols, saturated or unsaturated fatty alcohols, saturated or unsaturated fatty esters, saturated or unsaturated dicarboxylic acids, essential oils, phosphatidyl derivatives, cephalin, terpenes, amides, ethers, ketones and ureas); plasticizers (examples include but are not limited to diethyl phthalate and glycerin); solvents (examples include but are not limited to alcohol, corn oil, cottonseed oil, glycerin, isopropyl alcohol, mineral oil, oleic acid, peanut oil, purified water, water for injection, sterile water for injection and sterile water for irrigation); stiffening agents (examples include but are not limited to cetyl alcohol, cetyl esters wax, microcrystalline wax, paraffin, stearyl alcohol, white wax and yellow wax); suppository bases (examples include but are not limited to cocoa butter and polyethylene glycols (mixtures)); surfactants (examples include but are not limited to benzalkonium chloride, nonoxynol 10, oxtoxynol 9, polysorbate 80, sodium lauryl sulfate and sorbitan monopalmitate); suspending agents (examples include but are not limited to agar, bentonite, carbomers, carboxymethylcellulose sodium, hydroxyethyl cellulose, hydroxypropyl cellulose, hydroxypropyl methylcellulose, kaolin, methylcellulose, tragacanth and veegum); sweetening agents (examples include but are not limited to aspartame, dextrose, fructose, glycerin, mannitol, propylene glycol, saccharin sodium, sorbitol and sucrose); tablet anti-adherents (examples include but are not limited to magnesium stearate and talc); tablet binders (examples include but are not limited to acacia, alginic acid, carboxymethylcellulose sodium, compressible sugar, ethylcellulose, gelatin, liquid glucose, methylcellulose, povidone and pregelatinized starch); tablet and capsule diluents (examples include but are not limited to dibasic calcium phosphate, kaolin, lactose, mannitol, microcrystalline cellulose, powedered cellulose, precipitated calcium carbonate, sodium carbonate, sodium phosphate, sorbitol and starch); tablet coating agents (examples include but are not limited to liquid glucose, hydroxyethyl cellulose, hydroxypropyl cellulose, hydroxypropyl methylcellulose, methylcellulose, ethylcellulose, cellulose acetate phthalate and shellac); tablet direct compression excipients (examples include but are not limited to dibasic calcium phosphate); tablet disintegrants (examples include but are not limited to alginic acid, carboxymethylcellulose calcium, microcrystalline cellulose, polacrillin potassium, sodium alginate, sodium starch glycollate and starch); tablet glidants (examples include but are not limited to colloidal silica, corn starch and talc); tablet lubricants (examples include but are not limited to calcium stearate, magnesium stearate, mineral oil, stearic acid and zinc stearate); tablet/capsule opaquants (examples include but are not limited to titanium dioxide); tablet polishing agents (examples include but are not limited to carnuba wax and white wax); thickening agents (examples include but are not limited to beewax, cetyl alcohol and paraffin); tonicity agents (examples include but are not limited to dextrose and sodium chloride); viscosity increasing agents (examples include but are not limited to alginic acid, bentonite, carbomers, carboxymethylcellulose sodium, methylcellulose, povidone, sodium alginate and tragacanth); and wetting agents (examples include but are not limited to heptadecaethylene oxycetanol, lecithins, polyethylene sorbitol monooleate, polyoxyethylene sorbitol monooleate, polyoxyethylene stearate,).

Depending on the route of administration, the compositions can take the form of aerosols, cachets, capsules, creams, elixirs, emulsions, foams, gels, granules, inhalants, liposomes, lotions, magmas, microemulsion, microparticles, ointments, peroral solids, powders, sprays, syrups, suppositories, suspensions, tablets and tinctures. In addition, the black bean extract can be added to a food product or feed product with anti-oxidative effect.

The black bean extracts of the invention can optionally comprise a suitable amount of a pharmaceutically acceptable vehicle so as to provide the form for proper administration to the subject.

In a specific embodiment, the term "pharmaceutically acceptable" means approved by a regulatory agency of the Federal or a state government or listed in the U.S. Pharmacopeia or other generally recognized pharmacopeia for use in rats, mammals, and more particularly in humans. The term "vehicle" refers to a diluent, adjuvant, excipient, or carrier with which a compound of the invention is administered. Examples of suitable pharmaceutical vehicles are described in Remington's Pharmaceutical Sciences, Alfonso R. Gennaro ed., Mack Publishing Co. Easton, Pa., 19th ed., 1995, pp. 1447 to 1676, incorporated herein by reference.

In a preferred embodiment, the compounds of the invention are formulated in accordance with routine procedures as a pharmaceutical composition adapted for oral administration to human beings. Compositions for oral delivery may be in the form of tablets, lozenges, aqueous or oily suspensions, granules, powders, emulsions, capsules, syrups, or elixirs, for example. Orally administered compositions may contain one or more agents, for example, sweetening agents such as fructose, aspartame or saccharin; flavoring agents such as peppermint, oil of wintergreen, or cherry; coloring agents; and preserving agents, to provide a pharmaceutically palatable preparation. Moreover, where in tablet or pill form, the compositions can be coated to delay disintegration and absorption in the gastrointestinal tract thereby providing a sustained action over an extended period of time. Selectively permeable membranes surrounding an osmotically active driving compound are also suitable for orally administered compositions.

In these later platforms, fluid from the environment surrounding the capsule is imbibed by the driving compound, which swells to displace the agent or agent composition through an aperture. These delivery platforms can provide an essentially zero order delivery profile as opposed to the spiked profiles of immediate release formulations. A time delay material such as glycerol monostearate or glycerol stearate may also be used. Oral compositions can include standard vehicles such as mannitol, lactose, starch, magnesium stearate, sodium saccharine, cellulose, magnesium carbonate, etc. Such vehicles are preferably of pharmaceutical grade. Typically, compositions for intravenous administration comprise sterile isotonic aqueous buffer. Where necessary, the compositions may also include a solubilizing agent.

In another embodiment of the present invention, the black bean extract of the invention can be used in combination therapy with at least one other therapeutic agent and/or colorant agent. The black bean extract of the invention and the therapeutic agent can act additively or, more preferably, synergistically. In a preferred embodiment, a composition comprising a black bean extract of the invention is administered concurrently with the administration of another therapeutic agent, which can be part of the same composition as or in a different composition from that comprising black bean extract of the invention. In another embodiment, a composition comprising a black bean extract of the invention is administered prior or subsequent to administration of another therapeutic agent. As many of the disorders for which the compounds of the invention are useful in treating are chronic, in one embodiment combination therapy involves alternating between administering a composition comprising a black bean extract of the invention and a composition comprising another therapeutic agent, e.g., to minimize the toxicity associated with a particular drug. The duration of administration of the compound of the invention or therapeutic agent can be, e.g., one month, three months, six months, a year, or for more extended periods. In certain embodiments, when a compound of the invention is administered concurrently with another therapeutic agent that potentially produces adverse side effects including, but not limited to, toxicity, the therapeutic agent can advantageously be administered at a dose that falls below the threshold at which the adverse side is elicited.

For treating, preventing and/or inhibiting cancer or cancer cell growth, the therapeutic agent can be an anti-cancer agent. Useful anti-cancer agents include, but are not limited to, Erbitux, methotrexate, taxol, mercaptopurine, thioguanine, hydroxyurea, cytarabine, cyclophosphamide, ifosfamide, nitrosoureas, cisplatin, carboplatin, mitomycin, dacarbazine, procarbizine, etoposides, campathecins, bleomycin, doxorubicin, idarubicin, daunorubicin, dactinomycin, plicamycin, mitoxantrone, asparaginase, vinblastine, vincristine, vinorelbine, paclitaxel, and docetaxel, γ-radiation, alkylating agents including nitrogen mustard such as cyclophosphamide, ifosfamide, trofosfamide, chlorambucil, nitrosoureas such as carmustine (BCNU), and lomustine (CCNU), alkylsulphonates such as busulfan, and treosulfan, triazenes such as dacarbazine, platinum containing compounds such as cisplatin and carboplatin, plant alkaloids including vinca alkaloids, vincristine, vinblastine, vindesine, and vinorelbine, taxoids including paclitaxel, and docetaxol, DNA topoisomerase inhibitors including epipodophyllins such as etoposide, teniposide, topotecan, 9-aminocamptothecin, campto irinotecan, and crisnatol, mitomycins such as mitomycin C, anti-metabolites, including anti-folates such as DHFR inhibitors, methotrexate and trimetrexate, IMP dehydrogenase inhibitors including mycophenolic acid, tiazofurin, ribavirin, EICAR, ribonucleotide reductase inhibitors such as hydroxyurea, deferoxamine, pyrimidine analogs including uracil analogs 5-fluorouracil, floxuridine, doxifluridine, and ratitrexed, cytosine analogs such as cytarabine (ara C), cytosine arabinoside, and fludarabine, purine analogs such as mercaptopurine, thioguanine, hormonal therapies including receptor antagonists, the anti-estrogens tamoxifen, raloxifene and megestrol, LHRH agonists such as goscrclin, and leuprolide acetate, anti-androgens such as flutamide, and bicalutamide, retinoids/deltoids, Vitamin D3 analogs including EB 1089, CB 1093, and KH 1060, photodyamic therapies including vertoporfin (BPD-MA), phthalocyanine, photosensitizer Pc4, Demethoxy-hypocrellin A, (2BA-2-DMHA), cytokines including Interferon, α-Interferon, γ-interferon, tumor necrosis factor, as well as other compounds having anti-tumor activity including isoprenylation inhibitors such as lovastatin, dopaminergic neurotoxins such as 1-methyl-4-phenylpyridinium ion, cell cycle inhibitors such as staurosporine, alsterpaullone, butyrolactone I, Cdk2 inhibitor, Cdk2/Cyclin Inhibitory Peptide I, Cdk2/Cyclin Inhibitory Peptide II, Compound 52 [2-(2-hydroxyethylamino)-6-(3-chloroanilino)-9-isopropylpurine], Indirubin-3'-monoxime, Kenpaullone, Olomoucine, Iso-olomoucine, $N^9$-isopropyl-olomoucine, Purvalanol A, Roscovitine, (S)-isomer Roscovitine and WHI-P180 [4-(3'-hydroxyphenyl)amino-6,7-dimethoxyquinazoline, actinomycins such as actinomycin D and dactinomycin, bleomycins such as bleomycin A2, bleomycin B2, and peplomycin, anthracyclines such as daunorubicin, doxorubicin (adriamycin), idarubicin, epirubicin, pirarubicin, zorubicin, and mitoxantrone, MDR inhibitors including verapamil, and $Ca^{2+}$ ATPase inhibitors such as thapsigargin.

For lowering cholesterol or lowering oxidation of LDL or for inhibiting cholesterol synthesis, the therapeutic agent includes but is not limited to, fibrates such as bezafibrate, ciprofibrate, clinofibrate, clofibrate, fenofibrate, gemfibrozil, simfibrate; nicotinic acid and its derivatives such as nicomol, niceritol; dextran sulfate; colesevelam, colestipol, cholestyramine; probucol; 3-hydroxymethylglutaryl(HMG) CoA reductase inhibitors ("statin" inhibitors) including but not limited to atorvastatin (LIPITOR®), cerivastatin, fluvastatin (LESCOL®), lovastatin (MEVACOR®), mevastatin, pravastatin (PRAVACHOL®), simvastatin (ZOCOR®); MTP inhibitors including but not limited to BMS-201038, dietary and biliary cholesterol absorption inhibitors such as ezetimbe; ACAT inhibitors including but not limited to avasimibe. In one embodiment of the invention, the therapeutic agent is a 3-hydroxymethylglutaryl(HMG)CoA reductase inhibitor ("statin" inhibitors) selected from the group consisting of atorvastatin (LIPITOR®), cerivastatin, fluvastatin (LESCOL®), lovastatin (MEVACOR®), mevastatin, pravastatin (PRAVACHOL®) and simvastatin (ZOCOR®)

For reducing the symptoms of menopause or for calcium absorption in post-menopausal mammalian females, therapeutic agents include but are not limited to bisphosphonates including but not limited to alendronate (FOSAMAX®), pamidronate, residronate, ibandronate; calcitonon, calcium, conjugated estrogens (e.g. conjugated equine estrogen (PREMARIN®), ethinyl estradiol, selected estradiol receptor modulators (SERMS) including but not limited to raloxifene; thiazide diuretics including but not limited to hydrochlorothiazide, vitamin D and analogs thereof. Other natural therapeutic agents for reducing the symptoms of menopause include but are not limited to phytoestrogens such as isoflavones from soybeans and/or red clover.

For producing antioxidative effect, therapeutic agents include but are not limited to alpha tocopherol, ascorbic acid, ascrobyl palmitate, fumeric acid, malic acid, sodium ascorbate, sodium metabisulfate, n-propyl gallate, BHA (butylated hydroxy anisole), BHT (butylated hydroxy toluene) monothioglycerol and the like, may be added to the present formulation.

As the black bean extracts of the invention can contain anthocyanins, they are suitable for use in hair colorant, food colorant or dye products. Additional coloring agents may be added to the hair colorant or dye products and include but are not limited to the color additives:

(1) approved in Japan under Ministerial Ordinance No. 30 of 1966 as amended by MWH Ordinance No.55 in 1972; representative examples include but are not limited to Aka2, Aka102, Aka202, Aka404, Aka505, Ao1, Ao201, Ao404, Daidai201, Daidai401, Katsu201, Ki4, Ki204, Kuro401, Midoi202, Midoi402, Murasaki201, Murasaki401;

(2) approved in the European Union (EU) under Annex IV of the Cosmetics directive 76/768/EEC; representative examples include but are not limited to Acid Red 195, aluminum hydroxide, aluminum powder, aluminum stearate, anthocyanins, beetroot red, bromocresol green, bromothymol blue, calcium stearate, capsanthin/capsorubin, caramel, CI 10006, CI 11680, CI 12120, CI 14270, CI 15510, CI 21108, CI 28440, CI 42080, CI 44045, CI 45425, CI 58000, CI 69800, CI 71105, CI 77489, curcumin, lactoflavin, magnesium stearate, zinc stearate;

(3) batch certified by the U.S. Food and Drug Administration including but not limited to Blue 1, Blue 4, Brown 1, Ext. Violet 2, Ext. Yellow 7, Green 3, Green 6, Green 8, Orange 4, Orange 5, Orange 10, Orange 11, Red 4, Red 6, Red 7, Red 17, Red 21, Red 22, Red 27, Red 28, Red 30, Red 31, Red 33, Red 34, Red 36, Red 40, Violet 2, Yellow 5, Yellow 6, Yellow 7, Yellow 8, Yellow 10, Yellow 11;

(4) exempt from batch certification by the U.S. Food and Drug Administration including but not limited to aluminum powder, annatto, bismuth citrate, bismuth oxychloride, bronze powder, caramel, carmine, beta-carotene, chlorophyllin-copper complex, chromium hydroxide green, copper powder, dihydroxyacetone, disodium EDTA-copper, ferric ammonium ferrocyanide, ferric ferrocyaniode, guaiazulene, guanine, henna, iron oxides, lead acetate, magnesium violet, mica, pyrophyllite, silver, titanium dioxide, ultramarines, zinc oxide;

(5) classified as "coal tar hair dyes: in the U.S. Food, Drug and Cosmetic Act; representative examples include but are not limited to Acid Blue 62, Acid Orange 24, 2-amino-4-nitrophenol, 4-amino-2-nitrophenol, Basic Blue 9, Basic Brown 4, Basic Green 1, Basic Orange 2, Basic Red 1, Basic Red 46, Basic Violet 3, Basic Violet 16, Basic Yellow 40, Basic Yellow 87, HC Blue No. 5, HC Blue No. 14, HC Brown No. 1, HC Green No. 1, HC Orange No. 2, HC Red No. 3, HC Red No. 10, HC Violet No. 1, HC Violet No. 2, HC Yellow No. 4, HC Yellow No. 12, see also *International Cosmetic Ingredient Dictionary and Handbook* (9$^{th}$ Edition)—Chemical Classes—Coloring Additives—Hair (2002), which is incorporated by reference;

(6) batch certified by the U.S. Food and Drug Administration including but not limited to Blue 1 Lake, Ext. Yellow 7 Lake, Green 3 Lake, Orange 4 Lake, Orange 5, Orange 10 Lake, Red 4 Lake, Red 6 Lake, Red 7 Lake, Red 21 Lake, Red 27 Lake, Red 28 Lake, Red 30 Lake, Red 21 Lake, Red 33 Lake, Red 34 Lake, Red 36 Lake, Red 40 Lake, Yellow 5 Lake, Yellow 6 Lake, Yellow 7 Lake, Yellow 10 Lake;

(7) not classified above and listed in the *International Cosmetic Ingredient Dictionary and Handbook* (9$^{th}$ Edition)—Chemical Classes—Coloring Additives—Miscellaneous (2002), which is incorporated by reference.

The amount of black bean extract of the invention that will be effective in the treatment of a particular disorder or condition disclosed herein will depend on the nature of the disorder or condition, and can be determined by standard clinical techniques. In addition, in vitro or in vivo assays may optionally be employed to help identify optimal dosage ranges. The precise dose to be employed will also depend on the route of administration, and the seriousness of the disease or disorder, and should be decided according to the judgment of the practitioner and each subject's circumstances.

The prescribed dosage ranges for the additional therapeutic agents can either be based on the same suggested dosage ranges described for the black bean extract or based on commercially available dosage teachings known in the art. Such compositions can be administered to a subject or subject in need of such administration in dosages and by techniques well known to those skilled in the medical, pharmaceutical, nutritional or veterinary arts taking into consideration the data herein, knowledge in the art as to compounds or extracts from other food sources, doses of other flavonoid or flavonoid-derived actives, and such factors as the age, sex, weight, genetics and condition of the particular subject or subject, the condition being addressed, the route of administration, relative concentration of particular compounds, the dose that is shown to achieve 50% activity, e.g., $IC_{50}$ as to inhibiting cancer cell growth, and toxicity (e.g., $LD_{50}$). Doses can range from a few micrograms to a dose on the order of milligrams or even hundreds of milligrams, e.g., 0.01 µg to 500 mg, e.g., in a liquid form, from 0.01 µg/mL to 250 µg/mL, such as 60-100 or 60-80 or 80-100 µg/mL, or an approximate effective dose in the range 100 to 800 mg/day depending on the individual activities of the compounds or extracts in question and for a subject of average (70 kg) bodyweight, with more usual dosage rates for the preferred and more active compounds or extracts being in the range 200 to 800 mg/day, more preferably, 200 to 500 mg/day, most preferably from 200 to 250 mg/day. They may be given in single dose regimes, split dose regimes and/or in multiple dose regimes lasting over several days. For oral administration they may be formulated in tablets, capsules, solution or suspension containing from 100 to 500 mg of compound per unit dose. Alternatively and preferably the compounds will be formulated for parenteral administration in a suitable parenterally administrable carrier and providing single daily dosage rates in the range 200 to 800 mg, preferably 200 to 500, more preferably 200 to 250 mg. Such effective daily doses will, however, vary depending on inherent activity of the active ingredient(s) and on the bodyweight of the subject, such variations being within the skill and judgment of the physician or veterinarian or nutritionalist. Furthermore, compositions can be co-administered with other agents or actives, e.g., other agents or actives for conditions herein mentioned, for instance, with other antineoplastic, anti-tumor or anti-cancer agents or antioxidant, or estrogenic, or enzyme inhibiting agents and/or with agents which reduce or alleviate ill effects of agents or actives for herein mentioned conditions, e.g., antineoplastic, anti-tumor or anti-cancer agents or antioxidant or enzyme inhibiting agents; again, taking into consideration such factors as the age, sex, weight, and condition of the particular subject, and, the route of administration.

Examples of compositions of the invention for human or veterinary use include edible compositions for oral administration, such solid or liquid formulations, for instance, capsules, tablets, pills and the like, as well as chewable solid or beverage formulations, to which the present invention may be well-suited since it is from an edible source (e.g., bean flavored solid or liquid compositions); liquid preparations for orifice, e.g., oral, nasal, anal, vaginal etc., administration such as suspensions, syrups or elixirs (including bean flavored compositions); and, preparations for parental, subcutaneous, intradermal, intramuscular or intravenous administration (e.g., injectable administration) such as sterile suspensions or emulsions. However, if the active ingredient in the compositions may complex with proteins, such that when administered into the bloodstream, clotting may occur due to precipitation of blood proteins, the skilled artisan should take this into account. In such compositions the active black bean or hull extract or compound(s) thereof may be in admixture with a suitable carrier, diluent, or excipient such as sterile water, physiological saline, glucose, DMSO, ethanol, or the like. The active black bean or hull extract or compound(s) thereof of the invention can be provided in lyophilized form for reconstituting, for instance, in isotonic aqueous, saline, glucose or DMSO buffer. Indeed, given that black beans are edible and that those who ingest them have been observed to have lower cancer rates, oral or peripheral administration may be advantageous.

Further, the invention also comprehends a kit wherein the active black bean or hull extract or compound(s) thereof is provided. The kit can include a separate container containing a suitable carrier, diluent or excipient. The kit can also include an additional agent, e.g., an additional agent for a herein mentioned condition, such as an additional anti-cancer, anti-tumor or antineoplastic agent or antioxidant or enzyme inhibiting agent and/or an agent which reduces or alleviates ill effects of an agent or active of a condition herein mentioned, e.g., an antineoplastic, anti-tumor or anti-cancer agents or antioxidant or enzyme inhibiting agents for co- or sequential-administration. The additional agent(s) can be provided in separate container(s) or in admixture with the active black bean or hull thereof extract or compound(s) thereof. Additionally, the kit can include instructions for mixing or combining ingredients and/or administration.

Furthermore, while the invention is described with respect to black bean or hull extracts preferably comprising flavonoids and/or saponins, from this disclosure the skilled organic chemist will appreciate and envision synthetic routes to obtain the active compounds. Accordingly, the invention comprehends synthetic black bean or hull extract compounds such as flavonoids and/or saponins or their derivatives which include, but are not limited to glycosides, gallates, esters, etc. and the like.

For uses in the food or cosmetic compositions, the black bean or hull extract or compound(s) thereof are used in amounts typically used for colorants and antioxidants, e.g., about 0.1% w/w to about 5% w/w of the food or cosmetic.

The compounds of the invention are preferably assayed in vitro and in vivo, for the desired therapeutic or prophylactic activity, prior to use in humans. For example, in vitro assays can be used to determine whether it is preferable to administer a compound of the invention alone or in combination with another compound of the invention and/or a therapeutic agent. Animal model systems can be used to demonstrate safety and efficacy.

EXAMPLES

This invention will now be described with reference to the following non-limiting examples and the figures. The description and examples will refer to the methods and steps that may be followed in the application of the present invention as regards the obtaining, assessing and comparison of different varieties of black beans and to the various aspects and ways of determining the intrinsic advantages of the relative sources of black beans in terms of the concentration and bioactivity of a given set of black bean varieties and thus deriving from this characterization the most advantageous use of the extracts and compounds present in any given variety of black beans in order to treat or prevent different types of cancers as well as the various means of administering those for that purpose within the scope of this invention. Although the description and examples will be set forth in regard to certain black bean varieties of Mexico that the inventors used in their work and conception of the invention, it will be evident to those expert in the pertinent arts that the present invention can be extended in a similar manner to black bean varieties of other countries of the world or to new or other black bean varieties as these may evolve or in turn be considered, without departing from the general scope and coverage of this invention.

Example 1

A General Example and Methods of Application

Raw, germinated or cooked black beans are dried by either sun-drying or applied heat. The material is ground and the resulting meal extracted with a mixture of water miscible organic solvents and/or water to produce a raw extract. In the same manner as above, an extract can be prepared from black bean hulls or seed coats that were previously separated from the cotyledons. An aqueous raw extract may be passed through a C-18 column to remove simple water-soluble phenolics and water-soluble saponins and further eluted to produce flavonoid and triterpenes rich extracts. If the purification step by chromatography is omitted, the initial supernatants are physically separated from undissolved material, and the organic solvent is removed by distillation and lyophilized. After removal of the solvents, the solid material is recuperated to give a powder, which can be used alone or in combination with other nutrients or nutraceutical compounds, or dissolved in water, ethanol, other organic solvents or mixtures thereof to produce an extract rich in phenols, flavonoids, anthocyanins, tannins and/or isoflavones and/or triterpenes and/or phytosterols. Raw and/or C-18 extracts can be mixed with excipients to produce tablets or mixed and diluted with pharmaceutical grade sterile water and/or solvents to yield formulations for subcutaneous or intramuscular injections. Extracts can also be mixed with isotonic solutions to produce mixtures suitable for injection into the blood stream (parenteral application). Although this invention is expressed and referred to extracts from the natural source, and many of the active compounds have been identified, it is evident that these compounds may also be synthesized or modified by new methods such as combinatorial chemistry. The inventors consider that it is within the broader aspects of this invention that synthetic black bean compounds may be used separately or in a combined manner to produce therapeutic extracts thereof.

Example 2

Black Bean Varieties Tested and Method of Assaying These Initially

Twelve different black bean varieties were obtained from INIFAP (Instituto Nacional de Investigación Forestal Agrícola y Pecuaria) of Mexico and were chemically characterized in order to determine their phenolic and flavonoid concentrations with the aim of learning about these and assisting the practitioner of the invention in selecting the ones with more potential to be used as a source of nutraceuticals. Genotypes, tested are identified as follows: 1=Mex 332, 2=NG-Coaxtla 91, 3=NG-8025, 4=NG-San Luis, 5=NG Altiplano, 6=NG-150, 7=NG-Sahuatoba, 8=NG Tacana, 9=NG-Viscaya, 10=Negro Otomi, 11=NG-Perla, 12=NG-INIFAP. The main visual differences among the 12 varieties analyzed are the size and dullness. These varieties are selected based on adaptation to weather conditions and different types of soils, yield potential, and disease resistance, which indeed are among some of the reasons for their development and commercial release. For example, NG-Tacana (8) essentially has almost the same characteristics than NG-Cotaxtla 91 (2) but the first was developed with a particular resistance to viruses mostly found in Mexican tropical zones. The average yield of NG-Tacana (8) during the first year of commercial production (1994) was 1.214 tons/ha (Lopez-Salinas et al, 1994). More recently, NG-8025 (3) was also developed for this type of environment and has a higher yield, wider adaptation, more stability, and rust and anthracnosis resistance. Some varieties such as NG-Altiplano and NG-Viscaya (5) were developed because of their adaptability to semiarid zones.

Total Phenolic Quantification by Folin Calorimetric Assay (Vinson et al 2001):

As a first step to characterize the varieties, whole black bean samples (hull and internal mass composed essentially of cotyledons and embryo) were milled as a whole and the resulting whole meals extracted with 80% methanol in water and assayed for total phenols using the Folin calorimetric assay (Vinson et al 2001). FIG. 1 shows that the total phenolic content of the 12 varieties of black bean is at least 1.5 mg/g expressed as catechin weight equivalents, which is high compared to other legumes rich in phenolic compounds such as soybeans that generally have less than 1 mg/g and that were analyzed using the same conditions. Black bean varieties that contained the highest amount of total phenolics, expressed as catechin weight equivalents, were, as labeled, 1=Mex 332, 2=NG-Coaxtla 91, 3=NG-8025, 6=NG-150, 7=NG-Sahuatoba, and 10=Negro Otomi (FIG. 1).

Partial Fractionation via a Sep-Pak® $C_{18}$ Column and HPLC-UV Analysis:

Since not all the phenolic compounds have the same bioactivity, the inventors further pursued the characterization and analysis of the phenolic composition of each of the 12 black bean varieties. To analyze the phenolic composition, the above 80% methanol in water extracts were passed using a 10 ml plastic syringe through a Sep-Pak® $C_{18}$ column (Waters, Milford, Mass.) to remove compounds with greater hydrosolubility such as sugars. The methanol extract (10 ml) was diluted with 40 ml of distilled water and passed through the C18 column previously conditioned with 10 ml methanol and 10 ml water. The resulting 50 ml solution was passed through the column and then the column washed with 20 ml water. Then 2 ml of 30% methanol-water was passed through the column in order to elute "the first fraction". A "second fraction" was obtained by passing 2 ml methanol 100% through the column. Both, "first" and "second fraction" were analyzed to measure the concentration of the flavonoids of interest using an HPLC-UV.

HPLC Conditions:
Column: 150×3.9 mm Nova-Pak $C_{18}$ (4 µm) Column
Detector: HP 1100 UV-vis detector @ 262 nm
Flow rate: 0.4 ml/min
Column temperature: 25° C.
Injection: 20 µl of a preparation (1:1) water:methanol "second fraction"

Gradient:

| Time (min) | 60% Methanol in water | Water | 100% Methanol |
|---|---|---|---|
| 0 | 60 | 40 | 0 |
| 20 | 100 | 0 | 0 |
| 34 | 100 | 0 | 0 |
| 38 | 90 | 0 | 10 |

The "first fraction" of all the varieties analyzed did not appear to contain any appreciable amount of flavonols, flavones or isoflavones (less than 1% by weight based on dry weight of the compounds in the first fraction). However, the "second fraction", as expected, contained flavonoids and anthocyanins which were characterized further as described in the following examples.

The presence of isoflavones in black bean has been previously reported by Franke et al (1994), indicating the amount of 698.5 mg of daidzein, and 612.2 mg of genistein per kg of dry bean flour. Both isoflavones are also reported in higher or similar concentrations in soybeans (Nakamura et al, 2000). The chromatograms shown in FIG. 2 compare the types and concentrations of flavonoids extracted from black bean variety NG-Perla (11) and a commercial soybean flour, both chromatograms were obtained at a wavelength of 262 nm.

Chromatograms of FIGS. 2A and 2B are for soybean and black bean, respectively. Chromatogram FIG. 2B showed surprisingly that black beans did not contain any appreciable amount of daidzin (observe peak 1 of chromatogram FIG. 2A for soybeans versus negligible peak 10 of chromatogram 2B for "NG-Perla" black bean). Furthermore, soybeans apparently contained at least 9 times more genistin than black beans (observe peak 3 of chromatogram 2A versus peak 11 of chromatogram 2B and as reflected in the bar graph of total isoflavones in FIG. 3 for all 12 black bean varieties). Interestingly, when peak 11 of chromatogram 2B was further analyzed by HPLC-MS, its molecular weight did not match with genistin but with a flavonol glycoside. Likewise and somewhat surprisingly, all the black bean varieties showed the same typical chromatographic profile of FIG. 2B where it was observed that the black bean varieties tested did not contain daidzin, glycetin, diadzein, and genistein which are generally found in soybeans.

All black beans contained high amounts of now known or novel flavonoids, which elute at 13.032 minutes (note peak 12 in Chromatogram 2B) and 16.835 minutes (notice peak 13 in Chromatogram FIG. 2B) besides the one at 10.032 minutes that was confounded with genistin (note peak 11 in Chromatogram 2B). To generalize, all black bean varieties contained mainly three flavonoids (peaks 11, 12 and 13 of chromatogram 2B of FIG. 2B) that were compared to common isoflavone standards which included genistin, daidzin, genistein, glycitein, dadizein, equol, and biochanin A. After comparing with retention times of standards, it was concluded that, contrary to what was expected, the possible presence of known isoflavones in black bean samples was apparently reduced to only the compound represented by peak 11 in chromatogram 2B, which had the same retention time as genistin. As to identifying the compounds in peaks 12 and 13 of Chromatogram FIG. 2B, for brevity, the compound in FIG. 2 assumed eluting at peak 12 was cited and temporarily labeled as "A" and the compound eluting at peak 13 was temporarily cited as "B" pending further identification as explained in Example 3.

Considering that the now discovered flavonoids are related to genistin, in regard of their molecular weight and ultraviolet molecular extinction coefficient, the areas under the peaks (11, 12 and 13 in Chromatogram 2B) were converted to mg per kg (ppm) using genistin information and then the concentration expressed as genistin equivalents. FIG. 3 therefore presents, in terms of bars comprised of genitsin, compounds "A" and "B", the summary of the flavonoids absorbing at 262 nm for all the 12 varieties of black beans and the soybean comparator. The bar graph shows the corresponding sum of peaks 11,12 and 13 of chromatogram 2B as well as the genitsin peak for the soybean bar. The 12 black bean varieties contained less flavonoids by weight (absorbing at 262 nm) than the soybean sample analyzed (FIG. 3). Interestingly, as can be observed in FIG. 3, the black bean variety denoted as 11=NG-Perla contained approximately 6-times higher concentration of flavonoids than the rest of the varieties tested (FIG. 3). In contrast to soybeans (190 ppm of genistin), the NG-Perla variety had 120 ppm of flavonoids as genistin weight equivalents.

Example 3

Identification of Unknown Black Bean Flavonoids

HPLC-MS Analysis for Determination of Molecular Weights:

As to identification of black bean flavonoids, the inventors then proceeded as follows: The "second fraction" obtained and analyzed as described in Example 1 was further examined using a method for High Pressure Liquid Chromatography coupled to a Mass Spectrometry unit (HPLC-MS) with the following conditions:
Column: 150×1 mm VYDAC $C_{18}$ (5 μm)
Detector: Agilent 1100 UV-vis detector @ 262 nm
Flow rate: 0.075 ml/min
Column temperature: ambient
Injection: 20 μl of a preparation (1:1) water:methanol "second fraction"
Gradient:

| Time (min) | 100% Methanol | Water |
| --- | --- | --- |
| 0 | 25 | 75 |
| 6 | 27 | 73 |
| 11 | 40 | 60 |
| 32 | 60 | 40 |
| 62 | 100 | 0 |

An objective of the analysis was to confirm the presence of genistin according to the molecular mass obtained for peak 11 (Chromatogram 2B). Furthermore HPLC-MS would help to determine whether or not compounds A and B (peaks 12 and 13 of Chromatogram 2B) might be glycosidic-flavonoids, and obtain the molecular mass of their glycosides and corresponding aglycones.

First, only the compounds that absorbed at 262 nm were analyzed to limit the results mainly to isoflavones. Surprisingly, the results showed that the peak 11 from chromatogram 2B, previously identified as genistin because of its retention time, was not this type of isoflavone. As can be seen in Table 1, the HPLC-MS analysis showed that the black bean compound of peak 11 of chromatogram 2B (FIG. 2) had a higher molecular weight than genistin (480 daltons for peak 11 vs 432 daltons for genistin). Therefore, in view of this unexpected result, a further analysis of the peak 11 matter was done by double mass spectrometry (DMS) with the aim of finding out if the compound represented by peak 11 could have a bound sugar different from glucose attached to genistein. Results showed that the split molecule obtained from the DMS yielded two fractions, one with a molecular weight of 319 daltons and the other with 162 daltons. The lower molecular weight fraction (162) was likely the bound sugar (apparently glucose). Thus, this DMS result confirmed that the aglycone was not genistein (aglycone of genistin) that has a molecular weight of 271 daltons, not 319. After performing this DMS analysis, the inventors were thus faced with a dilemma since peak 11 was not confirmed as genistin and further identification was needed, since now the three peaks were still unknown compounds (peaks 11, 12 and 13).

Though not wishing to be bound by a specific theory at this moment, this apparently surprising difference of peak 11 may be attributed to the presence of additional hydroxyl groups and or the methylation of at least 2 hydroxyl groups present in the molecule. Nevertheless, the double mass spectrometry confirmed the presence of glycosidic forms of flavonoids (see Table 1) where the three major types observed had molecular weights of 448, 464 and 480 daltons. The corresponding double mass spectrometry resulted in split or disaggregated products of around 162 (bound sugar) and 286, 302 and 318, thus representing the bound sugar and the corresponding aglycone of the flavonoids.

TABLE 1

Molecular weight of flavonoids present in 12 black bean varieties and their corresponding aglycones.

| Compound | Glucosides MW* | Aglycones MW* | Bound sugar MW* |
| --- | --- | --- | --- |
| Previously identified as genistin (peak 11) | 480 | 318 | 162 |
| "A" (peak 12) | 464 | 302 | 162 |
| "B" (peak 13) | 448 | 286 | 162 |

MW*: Molecular weight in daltons

The inventors thus became aware at this point that apparently the potential of black beans had been overlooked by other workers in the field precisely because of the assumption that the apparent genistin peak was indeed genistin and so turned to other more prolific sources of genistin, not being aware that important non-genistin compounds were potentially present in the phantom genistin peak. Thus, others overlooked this important feature of black bean extracts and failed to characterize those for their potential bioactivity as the present inventors in contrast proceeded to do.

All the previous analysis of "second fraction" were done following the theory that the main compounds that should be found were isoflavones or related compounds that have a $UV_{max}$ around 262 nm. But since HPLC-MS permits the detection of all the molecules that can be ionized under the conditions previously mentioned, surprisingly there were other compounds present in the analyzed fractions that did not absorb at 262 nm but had high intensity peaks in the HPLC-MS chromatograms. These were less water-soluble than isoflavones since they started to appear when most of the mobile phase was methanol. The molecular weights of the positive ions of these molecules were higher than 900 daltons. When these compounds were double ionized they yielded a wide variety of molecular fractions. For example, the double ionization of a 981 daltons positive ion gave positive ions of 797, 635, 599 and 441 daltons indicating the presence of different monomeric units of polyphenols and/or molecules such as Phaseoloside D or E that have at least 6 molecules of glucose and/or galactose and/or arabinose and/or rhmanose bonded between them and attached to the third carbon of 12,15-Oleanadiene-3,23-diol as can be seen in FIG. 3A. No further analysis was done with these compounds since the main interest of the present invention is to evaluate less complex molecules that can be absorbed more easily and inhibit cancer cell growth. That is not the case of polyphenols that only can be used to treat certain types of cancer, such as colon, where they have more opportunity to be absorbed.

HPLC-PDA Identification:

In addition to the molecular weights obtained to describe applicants newly discovered flavonoids found in black beans, another technology used for the identification was the determination of their UV-VIS spectrums obtained using a Photo Diode Array detector with the High Pressure Liquid Chromatograph (HPLC-PDA). The "second fraction" (Example 1) from different varieties of black bean was injected in the system using the same conditions as in the case of HPLC-UV/vis except with different equipment. The samples were injected in a HPLC-PDA (Waters, Milford, Mass., USA) and the pH of water used as mobile phase was adjusted to 2.4 with o-phosphoric acid. In addition, the samples were hydrolyzed to obtain the corresponding UV spectrums for the aglycones. These chromatographic conditions, including the equipment, allowed the detection of an additional compound that eluted before the 3 flavonoids previously described in this Example and in Example 1 (peaks 11, 12, 13 of Chromatogram 2B). The mentioned compound is present in hydrolyzed and non-hydrolyzed samples as can be seen in FIG. 4 chromatogram 4A (peak 40) and chromatogram 4B (peak 50).

Furthermore, the hydrolysis conditions using 5 M HCl for 120 min or 5 M $H_2SO_4$ for 30 min in boiling water did not seem to affect the basic structure of the flavone used as internal standard (peak 44 of Chromatogram 4A and peak 54 of chromatogram 4B), since its retention time and the corresponding spectrum remained the same. Hydrolysis served to break glycosidic bonds of conjugated flavonoids as will be further explained in the following paragraphs. FIG. 4 shows differences in retention times of chromatograms obtained at 262 nm of the major black bean compounds (peaks 41, 42, 43 of chromatogram 4A vs peaks 51, 52, 53 of chromatogram 4B) and also shows changes in the spectrums obtained without hydrolysis (spectrum above Chromatogram 4A) and after acid hydrolysis (spectrum above Chromatogram 4B).

According to literature comparisons, the $UV_{max}$ of 285.8 nm obtained for the spectra of peak 40 from Chromatogram 4A (FIG. 4) can correspond to the characteristic band of absorption between 270 and 295 nm of the ring B of flavanones or dihydroflavonols (Mabry 1970). Other compounds that can correspond to the spectrum obtained for peak 40 are a group of isoflavones previously reported by Woodward (1979) in fungal contaminated French beans. These compounds have a peculiar band of absorption at wavelengths higher than 270 nm that are rarely found in isoflavones. One of the compounds is 7,2',4'-trihydroxy-8-(3,3-dimethylallyl) isoflavanone $C_{20}H_{20}O_5$, also known as 5-deoxykievitone, with a mass of 340.13 and a $UV_{max}$ of 286 nm; the other is phaseollin $C_{20}H_{18}O_4$ with a mass of 322 and a $UV_{max}$ of 279 nm. Interestingly, after hydrolysis of the black bean extracts, the retention time of peak 40 in comparison with the corresponding peak 50 (FIG. 4) did not change considerably but the $UV_{max}$ switched from 285 to 275 nm. Thus, considering the complex structures of the isoflavone candidates that have prenyl groups instead of a glycosidic substitution in ring B, it is possible that the compound represented by peak 40 in Chromatogram 4A might show this same characteristic. This previous consideration can explain why the retention time (as an indicator of the polarity of the compound) did not increase after the hydrolysis.

Peaks 41, 42 and 43 of Chromatogram 4A (FIG. 4) showed two bands in the UV spectra more related to the behavior of flavonols. Since rings A and B of flavonols may absorb light, their spectrums show two distinctive bands, one between 328-357 nm (Band I corresponding to ring A) and another between 240-280 nm (Band II corresponding to ring B). In fact, Band I of the UV spectrums of peaks 41, 42, 43 (FIG. 4) is characteristic of flavonols with a 3-hydroxyl substitution. Noteworthy, differences between UV spectrums from peaks 41, 42, 43 compared to peaks 51, 52, 53 are due to the change in the wavelength of Band I. For example, band I of peak 43 switched from 346.5 to 366.6 nm observed in peak 53. This change may be attributed to the hydrolysis of the substitution in the 3-hydroxyl since flavonols with a free 3-hydroxyl in ring A absorb between 352-385 nm (Mabry 1970).

With the previous information and conclusions reached after analyzing data there is a list of candidates for our newly discovered compounds (Table 2) previously characterized in chromatographs of FIG. 4. Identification was made with information obtained from the Dictionary of Natural Compounds (Chapman & Hall/CRC Press, 2004). For the compound represented by the peak 43 in Chromatogram 4A (FIG. 4) which is not hydrolyzed, there were other glycosidated forms of kaempferol that matched the spectrum criteria, but astragalin also matched the melting point between 180-190° C. Likewise, kaempferol is the best match for peak 53. Interestingly, in the data obtained from the analysis by HPLC-MS shown in Table 1, compound B had a molecular weight of 448 daltons, same as the molecular weight of kaempferol-3-O-glucoside. Likewise the non-glycosidated form of kaempferol has a molecular weight that corresponds to this particular compound. (Chapman & Hall/CRC Press, 2004). For peaks 41 and 42 and their corresponding aglycones (peaks 51 and 52) occurred the same case as for kaempferol but it was not confirmed with other physicochemical determinations.

TABLE 2

Identification of the Flavonols in the Black Bean Extracts shown in FIG. 4

| Before hydrolysis | | | After hydrolysis | | |
|---|---|---|---|---|---|
| Relative RT* or name | $UV_{max}$ (nm) Band I | $UV_{max}$ (nm) Band II | Relative RT* or name | $UV_{max}$ (nm) Band I | $UV_{max}$ (nm) Band II |
| 0.27 (peak 41) Myricetin 3'-rhamnoside ($C_{21}H_{20}O_{12}$) | 357 350 + 308 (sh) | 261 262 | 0.44 (peak 51) Myricetin 3',4',5',5,7-Pentahydroxyflavonol ($C_{15}H_{10}O_8$) | 370 374 | 254 254 |

TABLE 2-continued

Identification of the Flavonols in the Black Bean Extracts shown in FIG. 4

| | Before hydrolysis | | After hydrolysis | | |
|---|---|---|---|---|---|
| Relative RT* or name | $UV_{max}$ (nm) Band I | $UV_{max}$ (nm) Band II | Relative RT* or name | $UV_{max}$ (nm) Band I | $UV_{max}$ (nm) Band II |
| 0.37 (peak 42) | 354 | 257 | 0.59 (peak 52) | 370 | 254 |
| Quercitin 3-O-galactoside ($C_{21}H_{20}O_{12}$) | 358 | 255 | Quercetin 3',4',5,7-Tetrahydroxyflavonol ($C_{15}H_{10}O_7$) | 370 | 255 |
| Quercetin 3-glucopyranoside ($C_{21}H_{20}O_{12}$) | 358 | 256 | | | |
| Quercetin 4'-galactoside ($C_{21}H_{20}O_{12}$) | 356 | 257 | | | |
| 0.47 (peak 43) | 347 | 265 | 0.72 (peak 53) | 367 | 265 |
| Kaempferol 3-O-glucoside (Astragalin) ($C_{21}H_{20}O_{11}$) MW: 448.38 | 350 | 264 | Kaempferol or 4',5,7-Trihydroxyflavonol ($C_{15}H_{10}O_6$) | 367 | 266 |

*Relative retention time (RT): Ratio between the retention time of the internal standard (flavone) and the compound of interest under the same HPLC conditions.

Human hormone dependent mammary cancer cells (MCF-7) were used to conduct bioassays to test growth inhibitory effects of commercially available quercetin alone and in presence of other flavonols and phytochemicals found in black bean extracts described in Table 2. Quercetin alone did not have any inhibitory effect on MCF-7 growth whereas the extract rich in flavonols and other phytochemicals inhibited 50% of the growth at a concentration of 1.5 mg/mL.

Example 4

Anthocyanin Quantification

Since black beans are rich in anthocyanins and a characteristic red color in the "second fraction" (described in Example 2) was observed, the inventors quantified and characterized these compounds before testing the bioactivity of the "second fraction". The method used was modified from the one described by Mazza et al (1999) using HPLC-UV-vis with the following conditions:

Column: 250×4.6 mm Supelcosil $C_{18}$, 5 µm (Supelco Co., Bellefonte, Pa., USA)
Detector: HP 1100 UV-vis detector @ 525 nm
Flow rate: 0.35 ml/min
Column temperature: ambient
Injection: 20 µl of a preparation (1:1) water:methanol "second fraction"
Gradient:

| Time (min) | 5% (v/v) aqueous formic acid | 100% Methanol |
|---|---|---|
| 0 | 100 | 0 |
| 2.5 | 95 | 5 |
| 3 | 83 | 17 |
| 10 | 81 | 19 |
| 12 | 72 | 28 |
| 22 | 66 | 34 |
| 28 | 30 | 70 |
| 29 | 0 | 100 |
| 31 | 0 | 100 |
| 32 | 95 | 5 |
| 35 | 95 | 5 |

As in the case of flavonols reported in Example 3, anthocyanins are present as glycosides and the concentration is expressed as weight equivalents of the corresponding aglycones. All 12 of the tested black bean varieties had significant levels of anthocyanins delphinidine, petunidine and malvidin (FIG. 5). Interestingly the Mex-332 variety contained at least twice as much anthocyanins as the rest of the 12 tested black bean varieties. Interestingly, the ratio of these anthocyanins remained the same regardless of black bean variety. In conclusion, the "second fraction" (as described in Example 2 ) contained a mixture of flavonols, isoflavones and anthocyanins, which are proven antioxidant compounds that when present together act synergistically to lower proliferation of cancer cells and enhance other health benefits.

In addition, these anthocyanins containing extracts can be used as a natural source of coloring agents for different industries in substitution of synthetic FD&C color agents. Most synthetic color agents, especially FD&C red #2 or erythrosine, have important harmful health effects. Some of these synthetic dyes are prohibited by regulatory agencies in different countries around the world. Accordingly, natural color agents from beans for foods, cosmetics and drugs have significant utility. The extracts of the invention can be used as food colorants or cosmetic colorants or as food antioxidants or as cosmetic antioxidants in amounts typically used for colorants and antioxidants in food and cosmetics. For instance, the extract of the invention can be used in the amounts that are used for red #2 in food and cosmetics. Or, as substitute for other anthocyanins rich extracts, such as extracts obtained from *Vitis vinifera* currently used as a natural antioxidant in cosmetics.

Example 5

Dehulling and Characterization of Black Bean Hulls

It was interesting to analyze differences between the phenolics found in the whole black beans versus their hulls, since most of these compounds are concentrated in the hulls. Twelve different black bean varieties were independently conditioned with distilled water for 8 to 24 hours at room temperature in preparation for manual dehulling. Removed seed coats were weighed, dried at 60° C. for 12 hours and then milled into flour. The weight of the seed coats averaged 7 to 13% (dry basis) as can be observed in Table 3.

TABLE 3

Effect of black bean variety on the yield of seed coats or hulls

| Black Bean Variety | % Seed Coats ± Std. Error |
|---|---|
| 1. Mex-332 | 7.55 ± 1.22 |
| 2. NG-Cotaxtla 91 | 9.33 ± 0.68 |
| 3. NG-8025 | 9.20 ± 0.24 |
| 4. NG-San Luis | 9.23 ± 0.09 |
| 5. NG-Altiplano | 9.52 ± 0.33 |
| 6. NG-150 | 10.60 ± 0.67 |
| 7. NG-Sahuatoba | 10.66 ± 0.39 |
| 8. NG-Tacana | 12.94 ± 2.05 |
| 9. NG-Viscaya | 9.50 ± 0.77 |
| 10. Otomi | 8.21 ± 1.48 |
| 11. NG-Perla | 9.54 ± 1.29 |
| 12. NG-INIFAP | 10.87 ± 1.74 |

Black beans were also mechanically pearled or dehulled following the process summarized in FIG. 6a. The objective of the milling procedure was to obtain two different fractions: a seed testas rich material and a cotyledons rich material. Grains were first tempered to increase their moisture content to 16% for 12-16 hrs prior to dehulling. Conditioned seeds were mechanically dehulled in a PRL mill (Nutana Machine Co., Saskatoon Canada) equipped with abrasive disks. The optimum decortication was the time required to remove 13-15% of the grain weight in order to assure total removal of the hulls. The seed coat rich material was separated from the cotyledon rich material by air aspiration and then by sieving through a 2 mm diameter sieve.

Thus, FIG. 6a shows tempering or increasing moisture of beans, advantageously black beans, dehulling, aspirating dehulled beans to obtain aspirated hulls and remains thereof, sieving the remains to obtain hull fines and cotyldedons, combining the aspirated hulls and hull fines, and drying the combined aspirated hulls and hull fines to obtain dry bean hulls, advantageously dry black bean hulls.

The phenolic compounds from manually obtained hulls were extracted using 70% acetone, as will be further described in the following example, and chemically characterized. As in the case of the whole beans described in Example 2 , the total phenolic concentration in the hulls is different among varieties. Seed coats contained up to 20 times more phenolic compounds than their respective whole grains. So for some applications of the present invention, this consideration may lead the practitioner to prefer the embodiment of this invention which features a dehulling of the black bean source.

The total flavonoid and condensed tannin concentration was analyzed in black bean hulls. The black bean variety "NG-Perla" contained the highest concentration of flavonoids as can be observed in Table 4. Preliminary chemical tests indicated that most of the tannins were located in the seed coats. The varieties that contained the highest concentration of tannins in the hulls were NG-8025 (3) and NG-Sahuatoba (7) as can be observed in Table 4.

TABLE 4

Total phenolic, flavonoid, and tannin concentration of hulls manually removed from 12 black bean varieties.

| Black Bean Variety | Total phenolic concentration ± Std. Error (mg/g)* | Total flavonoid concentration ± Std. Error (mg/g)* | Total tannin concentration ± Std. Error (mg/g)* |
|---|---|---|---|
| 1. Mex-332 | 234.74 ± 15.22 | 39.16 ± 3.06 | 30.12 ± 0.96 |
| 2. NG-Cotaxtla 91 | 153.59 ± 37.05 | 23.76 ± 3.32 | 33.14 ± 0.59 |
| 3. NG-8025 | 199.20 ± 24.46 | 28.01 ± 1.00 | 53.76 ± 0.90 |
| 4. NG-San Luis | 212.45 ± 37.89 | 36.25 ± 6.09 | 27.05 ± 0.60 |
| 5. NG-Altiplano | 143.86 ± 33.21 | 29.07 ± 3.38 | 23.19 ± 0.70 |
| 6. NG-150 | 137.40 ± 00.35 | 27.56 ± 0.32 | 12.18 ± 0.30 |
| 7. NG-Sahuatoba | 84.92 ± 18.58 | 20.11 ± 3.84 | 33.98 ± 0.63 |
| 8. NG-Tacana | 107.45 ± 35.15 | 26.96 ± 4.96 | 23.93 ± 0.42 |
| 9. NG-Viscaya | 94.20 ± 35.94 | 23.42 ± 4.86 | 25.61 ± 0.42 |
| 10. Otomi | 149.64 ± 23.19 | 31.82 ± 3.53 | 37.94 ± 1.01 |
| 11. NG-Perla | 277.00 ± 16.86 | 47.91 ± 4.00 | 31.06 ± 0.89 |
| 12. NG-INIFAP | 186.35 ± 17.35 | 38.73 ± 2.55 | 15.76 ± 5.78 |

*All values are expressed as catechin equivalents on dry matter basis.

To confirm the presence of anthocyanins in the hulls of black beans, a thorough HPLC analysis was performed using acid-hydrolyzed anthocyanins. It was confirmed that the hulls of black bean variety MEX-332 have the highest anthocyanin concentration. The inventors found intriguing and interesting that this variety contained petunidin, pelargonidin and malvidin in addition to delphinidin and cyanidin that are present in all black bean varieties.

In another procedure to obtain testas and cotyledons from black beans, the beans were placed in a convection oven set at 60° C. for at least 6 hours, preferably for 8-10 hrs. During this time-temperature dehydration treatment, the testas became loose and were easier to separate after dehulling. Beans were mechanically pearled or dehulled with the aim of obtaining two fractions: seed testas or hulls and cotyledons. The optimum decortication was the time required to remove 13 to 15% of the grain weight. The seed coat rich material was separated from the cotyledon rich material by air aspiration and then by sieving through a sieve with 2 mm diameter circular holes. This procedure for mechanical fractionation is shown in FIG. 6b. This procedure was more effective than the above described procedure of FIG. 6a because it greatly reduced processing or decortication time.

Example 6

Extractions of Black Bean Hulls Using Different Solvents

Different solvents were used to evaluate their ability to isolate the compound of interest from black bean hulls prepared as described in Example 5. The different solvent systems evaluated included water, 80% methanol, 96% ethanol or 70% acetone (examples of water or aqueous solution and lower alkyl, e.g., $C_1$-$C_6$ alcohol, ketone/aldehyde, useful as solvents in the practice of the invention; lower alkyl ethers, such as ethyl ether are also useful as solvents in the invention). Extracts were obtained by mixing 100 ml of the solvent system with 5 grams of hulls. Mixtures were homogenized with a tissuemizer (Ultra-Turrax T25 basic, IKA Works Inc., Wilmington, N.C.) during 5 minutes at speed 3 and then kept in low agitation for 1 hr in a shaker (Bellco Glass Inc., Vineland, N.J.) at room temperature. An aliquot of the extract was sampled to determine total phenolic content by the Folin-Ciocalteu method and also to find out if there was a significant difference between this value and the one obtained from counterparts left overnight at refrigeration (4° C.) in darkness. After extraction, the resulting extracts were filtered through a Whatman 1 filter and the solid residue resuspended in 100 ml of fresh solvent. The process of adding 100 ml of solvent to the solid residues was repeated 3 times so at the end, the total extraction volume was 400 ml. The resulting volume was concentrated using a rotavapor Buichi (Scientific Glass Apparatus, Inc., Bloomfield, N.J.) at 40° C. to near dryness and resuspended in 100 ml of pure methanol.

Both 70% acetone and pure water were found to have excellent extraction of total phenolic compounds as observed in FIG. 7. For pharmaceutical and food grade commercial processes and regulatory agencies, water might be a better option according to the results shown in FIG. 7. Also, based on the bioactivity results, described herein and validated with an 80% methanol extract, it appears that water presents selectivity for the compounds of interest.

Example 7

Antioxidant Evaluation of Black Bean Hull Extracts

Surprisingly, a crude acetone black bean hull extract, with a total phenolic concentration of approximately 4 mM, had an antioxidant capacity of 58 µmol Trolox equivalents (TE) per gram (dry basis). This value is unexpectedly higher in reference to other anthocyanin-rich fruits such as highbush blueberries (4.6-31.1 µmol TE/g (fresh weight); Ehlenfeldt and Prior, 2001), strawberries (18.3-22.9; Kalt et al 1999), raspberries (19.2-22.6; Kalt et al 1999), blackberries (13.7-25.1; Wang and Lin, 2000), cranberries (8.20-14.5; Wang and Stretch, 2001), and muscadine grape juice (18.2-26.7; Talcott et al 2003).

To further evaluate the solubility characteristics of the bioactive compounds, the inventors proceeded to work with a crude methanol extract that was refined with ethyl ether to remove non-polar compounds. The remaining polar phase rich in phenolic compounds was further fractionated using a $C_{18}$ chromatographic column. Compounds were separated according to their polarity using sequentially methanol and ethyl acetate.

Fractions had different antioxidant capacities due to their diverse phenolic compositions (FIG. 8). Interestingly, 1 µmol of the phenolic compounds mixture obtained after the raw acetone hull extract that was further refined with ethyl ether and fractionated in methanol, showed an equivalent activity of approximately 2.5 µmol Trolox. The main phenolic compounds of this fraction were anthocyanins whereas the ethyl acetate fraction contained only traces of these compounds. Interestingly the ethyl acetate fraction selectively isolated most of the isoflavones, flavones and flavonols.

The antioxidant value obtained for the methanol fraction may be compared to synthetic butylated hydroxyanisole or BHA (2.43 TE) and the one from the ethyl acetate was between caffeic acid and quercetin (6.63-10.5 TE) (Dávalos, 2004). [note by PWM: What is "TE" - - - , Trolox Equivalent? or What? I don't see the definition anywhere, maybe I missed it or I just don't know what the terminology is.] This implies that both fractions have similar or higher antioxidant capacity than synthetic antioxidants commonly used by the food, cosmetics, pharmaceutical and feed industries. The antioxidant promoting natural compounds identified as whole or individually in this invention might substitute totally or partially for synthetic antioxidants that have proven harmful effects on health, such as cancer. Moreover, these compounds may be used as antioxidants in food, pharmaceutical or cosmetic products; and, black bean extracts, such as black bean hull extracts may be useful as a nutritional supplement.

Example 8

Malting/Germination Extracts of Whole Black Beans

A methodology for malting or germination beginning with whole black beans was developed with the aim of producing sprouts rich in aglycone-flavonoids. Preliminary malting tests indicated that apparently the optimum malting conditions were: soaking raw grains in water at 20° C. for 18-24 hr under aeration followed by germination in a controlled environment of 20° C. and 85% relative humidity. Under these conditions approximately 85% of the grains germinated during 3 days under controlled conditions of temperature (20° C.) and relative humidity (85%). The NG-Perla black bean variety was chosen to study the effect of malting time on glycosidation patterns of flavonoids, because it contained the highest amount of flavonols and isoflavones among the group of 12 varieties screened.

It would be evident to those skilled in the pertinent arts that it is within the scope of this invention to apply a similar method to dehulled whole black beans.

To analyze the effect of germination time on the black bean flavonoid concentration and profile, NG-Perla beans were soaked in 10 parts distilled water for 18 hours, the soaking water discarded, seeds germinated for five additional days at 20° C. and characterized daily. Germination was stopped by drying or dehydration at temperatures no greater than 60° C. to keep endogenous enzymes undamaged. Representative samples of raw and malted beans were ground and resulting meals extracted with 80% methanol and passed through the C-18 column as explained in Example 2 to quantify the flavonoid content using an HPLC-PDA with the following conditions:

Column: 250×4.6 mm Symmetry C-18 Waters Co. (Milford, Mass., USA)
Detector: Waters PDA 2996 (Milford, Mass., EUA.)
Flow rate: 0.8 ml/min
Column temperature: ambient
Injection: 20 µl of a preparation (1:1) water:methanolic "second fraction"
Gradient:

| Time (min) | Water* | 60:40 (v/v) Methanol:Water* |
|---|---|---|
| 0 | 95 | 5 |
| 5 | 95 | 5 |
| 55 | 35 | 65 |
| 58 | 0 | 100 |
| 60 | 95 | 5 |

*Both mobile phases were adjusted to pH 2.4 using o-phosphoric acid.

Interestingly, chromatograms of germinated black beans showed some different compounds, as the one represented by peak 114 in FIG. 9, in contrast to non-germinated raw black beans whether the latter were hydrolyzed or not. But, turning to FIG. 4, peaks 42 and 43 of chromatogram 4A, that correspond to non-hydrolyzed raw black bean extracts, these are the only flavonoids that showed up in the germinated beans.

As observed in FIG. 9, the corresponding spectrums of peaks 112 and 113 are similar to the ones obtained for the previously mentioned peak 42 and 43.

Unexpectedly, however, 1-day germinated black bean has a compound that also appeared in the hydrolyzed raw black bean extract previously analyzed. Comparing peak 110 of FIG. 9 with peak 50 of chromatogram 4B of FIG. 4, both have a spectrum and elution properties that are very similar even though peak 50 corresponds to a hydrolyzed extract and peak 110 is germinated rather that hydrolyzed. This is an interesting example of how germination may act to produce simpler compounds as in the case of acid hydrolysis that converted the compound in peak 40 to the one in peak 50, which is similar to the case of peak 110.

At the initial step of germination, soaking in excess water, the total flavonoid content of the black beans decreased when compared with the raw non-germinated grain. The soaking water was analyzed for flavonoids after an 18 hr steeping. As can be observed in FIG. 10, there may have been an important loss of flavonoids from the whole grain in the water. Only 1% of the flavonoids of interest were lost in the soaking water of grains soaked with 3 parts water whereas losses ranged from 4 to 15% in grains soaked with 6 parts water. Thus, the amount of water used for soaking may be reduced to avoid loss of flavonoids due to the leaching of these compounds.

Malting time had a significant effect on the concentration and types of flavonoids. The concentration of flavonoids gradually increased until the 4-day germination when it reached the maximum concentration in the germinated black bean (FIG. 11).

Thus, germination can be used to increase the bioactivity of flavanoids.

Although this example is related to effects of germination, there are other ways to increase the bioactivity of flavonoids. For example, the use of fermentation processes, acid hydrolysis and extrinsic enzymes that hydrolyze bound sugars (see U.S. Pat. Nos. 6,579,561, 6,500,965, 6,146,668, 5,320,949; 5,352,384; 5,637,561 and 5,637,562) may be employed. Nevertheless, germination of black beans is one of the embodiments of the invention that may be particularly advantageous, since it is a natural and simple process that increases the bioactivity of the compounds object of the present invention.

Example 9

In vitro Characterization Assays of Black Bean Raw and Malted Extracts against Proliferation of Hormone Dependent Mammary Cancer Cells MCF-7

Methanol extracts of raw and 5-day malted NG-Perla black beans were obtained by the methods described in Examples 2 and 8, respectively, and used to test their effects on hormone dependent mammary cancer cell proliferation (MCF-7).

Since isoflavones found in black beans may show estrogenic activity, and MCF-7 are hormone dependent mammary cancer cells; tests were conducted in hormone-free serum to discard the possibility of enhanced proliferation instead of inhibition. First assays were conducted on 2.5% bovine serum free of estrogens to prove that even if some flavonoids have estrogenic activity, they would inhibit cell proliferation. Thus, MCF-7 cells were first cultured with purified commercial standards of genistein (Indofine Chemical Company, Hillsborough, N.J.) and genistin (Sigma-Aldrich Chem. Co., St. Louis, Mo.) as positive controls with the aim of testing their effects on proliferation of this cancer cell line.

As shown in FIG. 12, as expected, genistein effectively inhibits the proliferation of MCF-7 after 13 days of incubation in vitro. The genistein concentration required to lower the cell population doublings from 6 to 3 (50% inhibition) was estimated by curve fit to the data of FIG. 12 as 18.5 µM. Genistin., The glycosidic form of genistein, did not have the same inhibitory effect even at concentrations higher than 20 µM, as can be observed in FIG. 13. Glucosidation has a negative effect over the activity of isoflavones in vitro, since genistin did not show proliferation inhibition in the range and conditions tested.

The "second fraction" of NG-Perla black bean extract obtained as described in Example 2, had an inhibitory effect on mammary cancer cell proliferation (FIG. 14). Interestingly, there were no viable cells after 13 days incubation when the medium contained concentrations higher than 13.6 µM of "second fraction" flavonoids. FIG. 14 shows that at concentrations higher than 1.36 µM of the compounds extracted from malted seeds, a strong inverse lineal relationship was found between isoflavone concentration and cell proliferation, with complete inhibition near 1.36 µM. This data clearly demonstrates that the utilization of germinated black bean extracts is about 10 times more effective than extracts obtained from whole raw seeds.

According to these results and comparing with pure genistin and genistein, it was concluded that flavonoids present in black beans had a much better effect and that the compounds obtained from malted black beans had a considerably stronger inhibitory potential. Enzymes (i.e. glucosidases) generated during the malting process hydrolyzed glycosides from flavonoids producing more biologically active aglycones and new isoflavones as described in Example 8.

Furthermore, assays using serum without previous hormone removal were performed using the same cell line (MCF-7). In addition, the raw extract of black bean hulls obtained and fractionated as described in Example 7 was used to differentiate the bioactivity of the phenolic compounds according to their sequential solubility in methanol and ethyl acetate. As in the case of hormone-free conditions, all extracts show strong inhibition as can be observed in Table 5. It is important to point out that raw extracts had the highest inhibitory effect, because their phenolic compounds needed to be less concentrated in comparison with the rest of the fractions tested.

In the case of the ethyl acetate fraction, where isoflavones and flavonols are present, a 50% inhibitory effect was not reached, since the concentration of total phenols was less than 30 µM. A higher concentration might be needed in order to obtain positive results.

TABLE 5

Comparison of inhibitory capacity of different solvent fractions obtained from crude acetone black bean extract on cancer cells (MCF-7) cultured in regular serum

| Fraction | $EC_{50}$* on MCF 7 (µM) |
| --- | --- |
| Crude acetone extract | 74.14 |
| Crude acetone extract after separation of ethyl ether soluble compounds | 92.07 |
| Methanol fraction | 107.75 |
| Ethyl acetate fraction | — |

$EC_{50}$* = Total phenolics concentration (µM) in cell growth media to inhibit 50% proliferation of MCF-7 cancer cells.

It was intriguing that such an inhibition of hormone dependent mammary cancer cells were observed when black bean extracts rich in phenolics were tested. Inhibition of MCF-7 cells using phenolic compounds was not predictable. For example, some flavonoids such as myricetin and epicatechin do not inhibit MCF-7 cells grown in regular serum conditions. On the other hand, a concentration of at least 200 µM of quercetin is needed to inhibit 50% of MCF-7 cancer cells under the same conditions (Rodgers, 1998). In U.S. Pat. No. 6,562,863, Romanczyk et al. found that more than approximately 100 µg/ml of cocoa procyanidins were needed to inhibit 50% MCF-7 in vitro cell proliferation. Interestingly, cocoa procyanidins were ineffective when fractionated indicating that the antiproliferative activity was achieved due to synergistic effects among different types of procyanidins.

In the current invention it was found that a lower concentration of total phenolic compounds in the medium was needed, when the raw extract was used, when compared with the methanol extracted fraction. Accordingly, there may be synergistic effects by the use of several compounds in a black bean extract (hull and/or bean). This demonstrates that there can also be a utility for black bean extract (hull and/or bean) as a nutritional supplement.

To provide further evidence of synergistic effects, assays were also conducted to compare crude extracts from malted beans in which the extracts differed in the amounts of triterpene-saponins and flavonols. The extracts with higher amounts of these triterpene-saponins and flavonols had a higher inhibitory effect than counterparts with lower concentration of these triterpene-saponins and flavonols. It is well known that saponins have affinity for estrogen receptors and therefore could enhance the activity of flavonoids.

Example 10

In vitro Characterization Assays of Black Bean Hull Extracts against Proliferation of Hepatic and Colon Cancer Cells Raw extracts of seed coats of different varieties of black beans were prepared and used to test their inhibitory effect on Caco-2 and HepG2 hepatic cancer cells. Seed coats (2 g) were mixed with 20 ml of 80% acetone, and the extract was obtained as described in Example 7. For both types of cells, the most antiproliferative extract was the one obtained from black bean variety 1 (Mex 332). The rest of the extracts also showed a great inhibitory capacity compared with other reported sources of flavonoids in foods. For example, Eberhardt et al (2000), working with apple extracts at concentrations of 50 mg/ml achieved 43 and 57% in vitro proliferation of Caco-2 and HepG2 cancer cells. In contrast, the black bean extracts at a concentration of less than 1 mg/ml lowered the proliferation of Caco-2 cancer cells to less than 20%. This means that black bean extracts were approximately at least 100 times more effective than apple extracts. Black bean extracts also showed great potency against HepG2 cancer cell proliferation, particularly when produced from black bean variety 1 (Mex 332). FIG. 15 shows the inhibitory effect of raw extracts from the Mex-332 black bean variety on HepG2 cancer cell proliferation. About 90% inhibition was observed when extracts contained more than 500 µM of total phenolics expressed as catechin equivalents.

The $EC_{50}$ or median effective dose for all extracts are listed in Table 6. The most effective extract for colon and hepatic cancer cell growth inhibition was the one produced from black bean Variety 1 (Mex 332). At equivalent concentrations, extracts were 4 to 5 times more effective against colon (Caco2) cancer cells in comparison to hepatic cancer (HepG2). The concentrations required to reach the median effective dose are very low in contrast with other reported extracts obtained from spinach, cabbage, or red pepper with $EC_{50}$ of 42.51±1.68, 56.26±2.24, 76.75±3.04 mg/ml, respectively (Chu et al, 2002). Black bean Mex-332 (1) at a concentration of 0.119 and 0.508 mg testa/ml cell medium inhibited 50% of Caco-2 and HepG2 cell proliferation, meaning that black bean extracts have several hundred times more bioactivity than extracts obtained from the horticultural crops mentioned above.

In general, black bean extracts may be used at very low concentrations to effectively inhibit a wide range of cancer cell lines, especially when extracts are obtained from hulls or germinated seeds. It also important to point out that different mixtures of the phenolic compounds have a higher bioactivity against cancer cell growth inhibition and antioxidant capacity.

TABLE 6

$EC_{50}$ values of antiproliferative activities towards human colon cancer Caco-2 cells and human liver cancer HepG2 cells by black bean extracts

| Sample | | $EC_{50}$ (µg/mL) | |
|---|---|---|---|
| No. | Variety | Caco-2 | HepG$_2$ |
| 1 | Mex 332 | 119 ± 18 | 508 ± 12 |
| 2 | NG-Cotaxtla 91 | 171 ± 6 | 615 ± 19 |
| 3 | NG-8025 | 247 ± 8 | 843 ± 14 |
| 4 | NG-San Luis | 173 ± 18 | 581 ± 5 |
| 5 | NG-Altiplano | 176 ± 4 | 804 ± 255 |
| 6 | NG-150 | 274 ± 3 | 796 ± 4 |
| 7 | NG-Sahuatoba | 469 ± 14 | — |
| 8 | NG-Tacana | 255 ± 14 | 745 ± 17 |
| 9 | NG-Voscaya | 227 ± 5 | — |
| 10 | Otomi | 190 ± 10 | — |
| 11 | NG-Perla | 241 ± 12 | 984 ± 90 |
| 12 | NG-INIFAP | 333 ± 11 | 1266 ± 243 |

Example 11

Protective Effect of Germinated Black Bean Extracts Against DMBA (9, 10-Dimethyl-1,2.benzanthracene) Induced Cancer using Wistar Rats The preventive effect of germinated black bean meal and its 80% methanol crude extract was tested using Wistar rats. To differentiate the effect of non-flavonoids compounds found in germinated black bean, an extraction was performed using 80% methanol in water in a 1:10 meal:solvent ratio. The amount of meal or extract was established according to the concentration of total phenolics in the diet considering 2 levels in the experiment: 13 mg/kg and 55 mg/kg. There were 4 experimental treatments and a control diet with 12 experimental units (27 days old) that were blocked by initial weight. Treatments were as follows:

a: Control diet
b: Low level of germinated black bean meal
c: High level of germinated black bean meal
d: Low level of germinated black bean meal phenolics extract
e: High level of germinated black bean meal phenolics extract DMBA was used as the chemical cancer inducer, dosing intragastrically 1 ml of an oil suspension of 20 mg/ml DMBA in corn oil. Induction was performed when rats were 50 days old with an average weight of 150 grams.

After cancer induction, 18 rats presented side effects to the DMBA and died before a visual evidence of tumors. The most affected treatments were b and c with only 50 and 58% survival after 14 days of induction with DMBA. FIG. 16 shows the median of the time in which DMBA-treated rats died, showing that most of the experimental animal units from treatment b died within the first 2.5 days post DMBA application; on the other hand, rats fed treatment c died 14 days after cancer induction. Only 25% of the subjects of the control treatment died during the first 3 days and 17% from treatment d and e died but after 14 days of chemical cancer induction. In comparison with control, treatments c, d, and e prevented early deceases due to DMBA toxicological reasons.

Tumors began to appear at day 59 after cancer induction in one animal from treatment d and the rat survived only 23 days with a tumor of 3.5 cm diameter that grew at a rate of approximately 0.1 cm/day. Rats from the control treatment showed palpable tumors by day 76 after cancer induction. In fact, some rats presented more than 1 tumor by day 84 but rats from treatments b and c did not present any tumors. FIG. 17 shows that rats from treatment A (control) were the most affected and most presented more than 1 tumor. Treatments d and e did not prevent as much tumor formation in comparison with treatments b and c. FIG. 17 shows that rats fed the diet containing the extract low in phenolics prevented cancer better than the diet containing the extract with a high phenolic concentration. Most of the rats of treatment d had none or only 1 tumor whereas rats of treatment e had higher incidence of tumors (FIG. 17). The difference between treatments with the whole germinated black bean (b and c) and with their methanol extracts (treatments d and e) indicated that there might be other compounds not necessarily flavonoids that prevent DNA oxidation induced by DMBA. On the other hand, treatments d and e demonstrated protection against DMBA toxicity at the same level but there is a substantial difference of cancer prevention between the low and the high level. Probably the high dose of extract in the diet promoted oxidation as it occurs with some other natural antioxidants.

The number of Wistar rats and their corresponding number of tumors after 84 days of cancer induction can be observed in FIG. 18. Taking into account all the experimental units, 49% of the rats did not present tumors, 29% had only one, 17% had 2, and the remaining 5% had 3 tumors. Treatments a (control) and e (high level of germinated black bean phenolics extract) were the most affected since tumor prevention in their corresponding rats was only 25 and 30%, respectively. Rats under treatment c were the least affected since only 14% of the experimental units presented tumors 84 days post-induction, followed by treatment b with 33%. In both treatments b and c, there was only one tumor in the affected rats. 50% of the rats of treatment a, 40% of treatment e and 10% of treatment d had at least 2 tumors.

Example 12

Fractionation of Black Bean Hulls Extracts using Solvents with Different Polarity to Increase their Cancer Inhibitory Effect A separation scheme using solvents with different polarity was developed for the isolation of bioactive flavonoids from black bean seed coats or hulls initially extracted with 40% acetone or 80% methanol. A general quantification of phenolic compounds was performed in each sequential step in order to determine the fate of these compounds and find out the fraction(s) with the highest concentration of bioactive compounds. FIG. 19 shows the steps involved in this separation scheme with the different fractions, where LI is the liquid obtained after solvent evaporation, LII is the liquid stream after salt precipitation and from which a butanolic (B) and a water stream (LIII) are going to be obtained after several washes with butanol. From the dried butanolic fraction an ethanol:ethyl acetate solution is going to be used to obtain a precipitate once ether is added to the mixture and the rest of the compounds will be in solution in LE.

Since most of the bioactivity of black bean hulls has been attributed to the flavonols such as the glycosides of myricetin, quercetin and kaempferol, the aim of the separation scheme was to eliminate as much as possible all the other foreign chemical compounds originally found in the acetone or methanol crude extracts. FIG. 20 shows that flavonols were not detected in raw extracts LI due to the high concentration of other compounds, mainly saponins and phytosterols. In fraction B, flavonol glycosides appeared in significant quantities as can be seen in the chromatogram (FIG. 20). However, the fraction LE obtained after ether precipitation contained the highest and purest concentration of these bioactive compounds.

As expected (Table 7) a different bioactivity against the growth of MCF-7 mammary cancer cells was observed in vitro when using the different fractions which demonstrates that there may be some compounds that are exerting the highest bioactivity and others that probably interfere with the antiproliferative activity. An interesting observation was obtained when using the raw extract (LI), because instead of having an inhibitory effect there was an increase in the number of MCF-7 cancer cells probably due to the significant quantities of phytosterols present in black bean hulls. According to Ju (2004) these phytochemicals promote the in vitro cell growth of MCF-7 cancer cells. The final product obtained from the flavonoids dissolved in butanol and treated as described in FIG. 19 (LE) had the highest bioactivity against cancer cell growth. Only 0.1 mg/ml were needed to inhibit 55% of the cell growth. The most interesting results were obtained with the fraction obtained after ether precipitation of the evaporated fraction B. A concentration of 0.05 mg/ml was sufficient to inhibit in vitro cancer growth by 46%. According to LeBail et al (1998) some flavonols inhibit cancer cell growth at low concentrations and promotes growth at higher concentrations when incubated in presence of estrogens. Results of Table 7 agree with these previous investigations.

TABLE 7

Comparison of percentage growth inhibition of MCF7 mammary cancer cells after 48 h incubation using different solvent fractions.

| Concentration in growth media | Fraction | | |
| --- | --- | --- | --- |
| | LI | B | LE after ether precipitation of contaminants |
| 0.05 mg/ml | −18.8% | 0% | 46.45% |
| 0.1 mg/ml | −41.55% | 35% | 55.31% |
| 0.2 mg/ml | −19.66% | 43% | 39.26% |
| 0.25 mg/ml | −19.41% | 42.87% | 40.99% |

Results obtained for the final fraction (LE) of the separation scheme was compared with a commercial product commonly used to treat cancer (Taxol(®, SIGMA). Data shows the potential therapeutic potential of the mixture of compounds obtained after the sequential fractionation scheme shown in FIG. 19. As can be seen in FIG. 21, at a concentration of 0.5 mg/ml, fraction LE was more effective than Taxol®. At this concentration, the experimental extract had the same effectiveness of Taxol® when the former compound was used at 10 times higher concentration. Extract LE had the highest effectiveness at concentrations less than 0.1 mg. The separation of the bioactive compounds of this extract via Preparative HPLC or other methods might yield pure pharmaceutical compounds that can be used at lower concentrations than Taxol®. The other advantage of using these natural phytochemicals is that they may have less toxicological and side effects than Taxol®.

The LE extract contained glycosidic flavonols, phaseoloside E and other related compounds and the surprisingly effective inhibitory activity of fraction LE could be due to the synergistic effect of flavonols and other compounds found in this extract such as the ones documented in FIGS. 3A and 22 or due to one particular phytochemical present in this extract. Except for flavonols and their glycosidic forms, all the compounds eluted during the first 5 minutes in the chromatograms shown in FIG. 20. The possible synergistic effect may be due to the presence of compounds with high estrogenic activity found in LE (such as flavonols, i.e. myricetin) that may allow the migration or entrance into the cell of other compounds that are better apoptosis inducers than flavonols. In other words, the growth inhibition and/or apoptosis of human mammary cancer cells may be greatly enhanced when both types of compounds are present in the extract.

Example 13

Therapeutic Effect of Black Bean Hulls Extract and Its Purified Fraction Against DMBA-Induced Mammary Cancer Using Wistar Rats A lyophilized black bean hull extract obtained using 80% methanol in water was further purified as described in Example 12. The freeze-dried raw extract and its semi-purified fraction were tested as therapeutic agents against mammary cancer cell growth using Laboratory Wistar rats. Five groups of 6 to 8 rats were induced with 15 mg of DMBA suspended in 1 ml of corn oil administered intragastrically when they reached between 40 to 50 days old. Experimental units that presented palpable tumors in less than 10 weeks after cancer induction were not included in the experiment and instead used for another experiment that will be described later.

Extracts were dissolved in 25% DMSO in water and 0.5 ml were administered intragastrically every 2 days during 7 weeks. Two concentrations of raw and semipurified extracts were used, giving the following treatments:
C: Control (only 25% DMSO)
R1: Raw extract (35 mg d.w./ml)-(d.w.—dry weight)
R2: Raw extract (3.5 mg d.w./ml)
A1: Semi-Purified extract (5 mg d.w./ml)
A2: Semi-Purified extract (0.5 mg d.w./ml)
FIG. 23a shows the tumor growth rate observed in Wistar rats administered with 25% DMSO with no extract (control) and with extracts defined above.

The main differences among treatments detected after 7 weeks were on number of tumors per rat (metastasis), time needed for metastasis, time to growth arrest, and tumor growth rate. Metastasis was observed in 50% of the control rats, only 25% of the rats administered the raw extract at high concentration had metastasis whereas no metastasis was observed in rats given the semi-purified extract. There was an interesting difference between rats treated with the raw extract and control in the time needed for the second tumor to be palpable, 28 days and 1-14 days respectively.

Growth rate of the first palpable tumor in control rats was around 0.35 cm/day until reaching a maximum size of 1.5-2.0 cm. Tumors from rats treated with semi-purified extract in low and high concentration grew at a daily rate between 0.05-0.1 cm. A similar trend was observed in rats treated with raw extract with the difference that for counterparts administered the semipurified extract the appearance of a second tumor was non-existent or nil. Second palpable tumors in rats treated with raw extract grew at a rate of 0.05 cm/day that represents one fifth of the average rate observed in control rats.

Tumor growth was arrested only when raw or semipurified extract were administered. In both cases tumor diameter remained in approximately 0.5 cm forty days after they were first palpable.

The freeze-dried raw extract described in the previous example was tested at four different concentrations to evaluate the effect on mammary cancer tumor growth using the experimental units with higher susceptibility to DMBA cancer induction. Laboratory Wistar rats that presented palpable tumors before a 10 weeks period after DMBA administration were used for this experiment. During 3 weeks 1 ml of distilled water with freeze-dried raw extract in concentrations of: 35, 18, 9, 4 and 0 mg/ml were administered intragastrically every 2 days.

As can be observed in FIG. 23b, there was a significant decrease in tumor size when 4 mg/ml were administered to a rat with a tumor of 1.3 cm diameter that after 3 weeks decreased to 0.5 cm. When only distilled water was administered the opposite effect was observed since tumor diameter increased from 0.7 to 1.5 cm. There was an interesting effect when using a dose of 35 mg/ml since tumor diameter was arrested in a value of 1.4 cm during 12 days but then increased to 2.2 cm. Other experimental units that were administered with 35 mg/ml have not shown this considerable increase. It is important to consider the initial diameter of tumor to compare the growth rate of each treatment. As can be observed in FIG. 23c there is an important difference between experimental units treated with freeze-dried raw extracts and controls. Furthermore, there is no significant difference in administering 35 or 4 mg/ml. Apparently there is a tendency to increase rate when 35/ml are administered after 20 days, opposite to the decrease tendency observed when using 4 mg/ml, but the error bars are transposed indicating the need of more experimental units to conclude this.

It is important to consider that besides the size of the tumor, there is a significant morphological difference between the tumors of rats that received the extract and the ones where only distilled water was administered intragastrically. FIG. 24 clearly shows that tumors from rats administered with the extract were less irrigated than the blank using only water, this may be related with the lower incidence of metastasis that has been observed. Because even if there were 2 tumors in one of the experimental units, both were in the same region and they appeared more like a splitting up of the initial tumor.

Example 14

Application of ATPS in Separating of Phytochemicals from Black Bean Extracts

ATPS (Aqueous two-phase systems) were characterized by the use of polyethyleneglycol (PEG) and potassium phosphate solution. System parameters included the concentration of PEG and potassium phosphate solution, the molecular weight of PEG (from 8,000 to 20,000 g/gmol), the volume ratio between the two immiscible phases and the amount of crude extract initially added to the system.

Predetermined quantities of stock solutions of polyethylene glycol (PEG) and potassium phosphate were mixed with a complex mixture of black bean hulls extracts at different concentration (from 5 to 20% of sample in the whole system), to give a final weight of 10 g. The stock solutions (PEG or salts) were mixed and phases dispersed by gentle mixing for 30 min at 25° C. Adjustment to pH 7 was made by addition of orthophosphoric acid or sodium hydroxide. Complete phase separation was achieved by low speed batch centrifugation at 1500 g for 5-20 min at 25° C. Estimates of the volumes of top and bottom phases and solids, were made in graduated centrifuge tubes. The volumes of the phases were used to estimate the volume ratio (Vr). Samples were carefully extracted from the phases (top phase, bottom phase and interface) and diluted for chemical analysis (see FIG. 25 for pictoral representation). The systems tie-line length (TLL), which represents the length of the line that connects the composition of the top and bottom phase of a defined ATPS, was calculated as described by Rito-Palomares (2004).

In all the systems, it was observed that the compounds with smaller molecular weights, such as the ones shown in FIG. 22, were predominant in the bottom salt-rich phase. On the other hand, in the top PEG-rich phase concentrated all the glycosidic flavonols, anthocyanins, and tannins. Resulting compounds retained in the top PEG-rich phase can be further separated with the addition of different amounts of salt solutions to form a new ATPS extraction system. Salt and PEG from the bottom and top phase, respectively, can be removed from the phytochemicals preferably by ultrafiltration and/or reverse osmosis or other operations such as precipitation, dialysis, diafiltration, chromatographic methods and/or supercritical $CO_2$.

TABLE 8

Distribution as percentage of phytochemicals in the bottom and top phase of 16 Aqueous-Two Phase Systems.

| System | $V_R$ | PEG (M.W.) | TLL | Sample Conc. | % Bottom | % Top |
|---|---|---|---|---|---|---|
| 1 | 0.2 | 8000 | 20% | 5% | 14.98 ± 3.19 | 85.02 ± 3.19 |
| 2 | 0.2 | 20000 | 20% | 5% | 12.12 ± 2.23 | 87.88 ± 2.23 |
| 3 | 0.2 | 8000 | 20% | 10% | 12.05 ± 1.37 | 87.95 ± 1.37 |
| 4 | 0.2 | 20000 | 20% | 10% | 7.12 ± 0.93 | 92.88 ± 0.93 |
| 5 | 0.2 | 8000 | 30% | 5% | 11.43 ± 1.21 | 88.57 ± 1.21 |
| 6 | 0.2 | 20000 | 30% | 5% | 11.45 ± 1.48 | 88.55 ± 1.48 |
| 7 | 0.2 | 8000 | 30% | 10% | 5.69 ± 3.14 | 94.31 ± 3.14 |
| 8 | 0.2 | 20000 | 30% | 10% | 6.58 ± 0.51 | 93.42 ± 0.51 |
| 9 | 1.0 | 8000 | 20% | 5% | 19.77 ± 2.57 | 80.23 ± 2.57 |
| 10 | 1.0 | 20000 | 20% | 5% | 16.25 ± 1.72 | 83.75 ± 1.72 |
| 11 | 1.0 | 8000 | 20% | 10% | 18.12 ± 1.34 | 81.88 ± 1.34 |
| 12 | 1.0 | 20000 | 20% | 10% | 15.09 ± 2.55 | 84.91 ± 2.55 |
| 13 | 1.0 | 8000 | 30% | 5% | 22.28 ± 3.40 | 77.72 ± 3.40 |
| 14 | 1.0 | 20000 | 30% | 5% | 20.70 ± 2.85 | 79.30 ± 2.85 |
| 15 | 1.0 | 8000 | 30% | 10% | 19.71 ± 1.96 | 80.29 ± 1.96 |
| 16 | 1.0 | 20000 | 30% | 10% | 18.14 ± 3.18 | 81.86 ± 3.18 |

This process resulted in a reduction of the amount of solvents used relative to traditional extraction techniques and was also beneficial in that the extraction was able to be performed at room temperature. In addition, the process could be performed in situ using the same agitation tank since for the separation of phases only a short decantation time was required.

Having thus described in detail advantageous embodiments of the present invention, it is to be understood that the invention defined by the above paragraphs is not to be limited to particular details set forth in the above description as many apparent variations thereof are possible without departing from the spirit or scope of the present invention.

REFERENCES

U.S. Patent Documents

| | | | |
|---|---|---|---|
| US2004/0131749 A1 | Grabiel et al | Jul. 8, 2004 | 426/629 |
| US2003/0068329 A1 | Kosuna et al | Apr. 10, 2003 | 429/195.15 |
| US2003/0078214 A1 | Kelly | Apr. 24, 2003 | 514/27 |
| US2003/0068329 A1 | Ramot et al | Jun. 5, 2003 | 424/757 |
| US2003/0068329 A1 | Meijer et al | Jun. 12, 2003 | 424/439 |
| US2003/0113390 A1 | Hoie | Jun. 19, 2003 | 424/757 |
| US2003/0118675 A1 | Waggle et al | Jun. 26, 2003 | 424/757 |
| US2003/0125229 A1 | Rodriguez | Jul. 3, 2003 | 514/1 |
| US2003/0125265 A1 | Kosuna et al | Jul. 3, 2003 | 429/195.15 |
| US2003/0129217 A1 | Festo | Jul. 10, 2003 | 429/439 |
| US2003/0129258 A1 | Pushpangadan et al | Jul. 10, 2003 | 424/725 |
| U.S. Pat. No. 6,607,757 | Bombardelli et al | Aug. 19, 2003 | 424/757 |
| U.S. Pat. No. 6,579,561 | Bryan et al | Jun. 17, 2003 | 426/634 |
| U.S. Pat. No. 6,562,863 | Romanczyk et al | May 13, 2003 | 514/453 |
| U.S. Pat. No. 6,562,380 | Kelly | May 13, 2003 | 424/757 |
| U.S. Pat. No. 6,541,613 | Hendler et al | Dec., 15, 2002 | 536/8 |
| U.S. Pat. No. 6,514,527 | Buchholz et al | Feb. 4, 2003 | 424/464 |
| U.S. Pat. No. 6,500,965 | Paracchini | Dec. 31, 2002 | 549/403 |
| U.S. Pat. No. 6,497,906 | Kelly | Dec. 24, 2002 | 424/757 |
| U.S. Pat. No. 6,482,448 | Tabor | Nov. 19, 2002 | 424/757 |
| U.S. Pat. No. 6,479,539 | Romanczyk et al | Nov. 12, 2002 | 514/453 |
| U.S. Pat. No. 6,410,061 | Morre et al | Jun. 25, 2002 | 424/729 |
| U.S. Pat. No. 6,146,668 | Kelly et al | Nov. 14, 2000 | 426/46 |
| U.S. Pat. No. 6,004,558 | Thurn and Huang | Dec. 21, 1999 | 424/757 |
| U.S. Pat. No. 5,762,936 | Ronzio et al | Jun. 9, 1998 | 424/757 |
| U.S. Pat. No. 5,637,562 | Shen et al | June 1997 | 435/125 |
| U.S. Pat. No. 5,637,561 | Shen et al | June 1997 | 435/125 |
| U.S. Pat. No. 5,352,384 | Shen | October 1994 | 424/195 |
| U.S. Pat. No. 5,336,685 | Prochaska et al | Aug. 9, 1994 | 514/455 |
| U.S. Pat. No. 5,320,949 | Shen | June 1994 | 424/195 |

Foreign Patent Documents

| | | |
|---|---|---|
| JP 5170756 | | July 1993 |

Literature

Adom, K. K., Liu, R. H. 2002. Antioxidant activity of grains. J. Agric. Food Chem. 50: 6182-6187.

Azevedo, L., Gomes, J. C., Stringheta, P. C., Gontijo, A. M. M. C., Padovani, C. R., Ribeiro, L. R., Salvadori, D. M. F. 2003. Black bean (*Phaseolus vulgaris* L.) as a protective agent against DNA damage in mice. Food and Chemical Toxicology. 41: 1671-1676.

Bawadi, H. A., Bansode, R. R., Trappey II. A., Truax, R. E., Losso, J. N. 2005. Inhibition of Caco-2 colon, MCF-7 and Hs578T breast, and DU 145 prostatic cancer cell proliferation by water-soluble black bean condensed tannins. Cancer Letters. 218: 153-162.

Beninger et al., "Flavonol Glycosides from the Seed Coat of a New Manteca-Type Dry Bean (*Phaseolus vulgaris* L.)," J Agric Food Chem 46:2906-2910 (1998).

Beninger et al., "Flavonol Glycosides from Montcalm Dark Red Kidney Bean:implications for the Genetics of Seed Coat Color in *Phaseolus vulgaris* L.," J Agric Food Chem 47:4079-4082 (1999).

Burden, R. S., Bailey, J. A., Dawson, G. W. 1972. Structures of three new isoflavonoids from *Phaseolus vulgaris* infected with tobacco necrosis virus. Tetrahedron Letters. 41: 4175-4178.

Cardador-Martinez, A., Loarca-Piña, G., Oomah, B. D. 2002. Antioxidant activity in common beans (*Phaseolus vulgaris* L.) J. Agric. Food Chem. 50: 6975-6980.

Castellanos, J. Z. Guzmán, H., Jiménez, A., Mejía, C., Muñoz, J., Acosta, J. A., Hoyos, G. López, E., González, D., Salinas, R., González, G., Muñoz, J., Fernández, P., Cáceres, B. 1997 Hábitos Preferenciales de los Consumidores de Frijol Común (*Phaseolus vulgaris* L.) en México. Archivos Latinoamericanos de Nutrición. 47 (2):163-167. Chapman & Hall/CRC Press. 2004. Dictionary of Natural Products. Accesed on Feb. 02, 2004 at: http://www.chem-netbase.com.millenium.itesm.mx/

Chu, Y. F., Sun, J., Wu, X., Liu, R. H. 2002. Antioxidant and antiproliferative activities od common vegetables. J. Agric. Food Chemistry. 50: 6910-6916.

CONAPO (Consejo Nacional de Población). Población de México en cifras. Indicadores de salud reproductiva: Tasa de mortalidad por cáncer de la mama según entidad federativa en 1997. Accesed on Feb. 16, 2004 at: http://www-.conapo.gob.mx/m_en_cifras/principal.html Constantinou, A. I., Krygier, A. E., Mehta, R. R. 1998. Genistein induces maturation of cultured human breast cancer cells and prevents tumor growth in nude mice. Am. J. Clin. Nutr. 68S: 1426S-30S.

Dávalos, A. Gómez, C., Begoña, B. 2004. Extending applicability of the oxygen radical absorbance capacity (ORAC-Fluorescein) assay. J. Agric. Food Chem. 52: 48-54.

Eberhardt, M. V., Lee, C. Y., and Liu, R. H. 2000. Antioxidant activity of fresh apples. Nature 405: 903-904.

Ehlenfeldt, M. K., Prior, R. L. 2001. Oxygen radical absorbance capacity (ORAC) and phenolic and anthocyanin concentrations in fruit and leaf tissues of highbush blueberry. J. Agric. Food Chem. 49:2222-2227.

Franke, A. A., Custer, L. J., Cerna, C. M., Narala, K. K. 1994 Quantitation of phytoestrogens in legumes by HPLC. J. Agric. Food Chem. 42 (9): 1905-1913.

Gutiérrez Uribe, Janet A., Effect Of Germination On The Content And Profile Of Isoflavones Of Black Beans (*Phaseolus Vulgaris*) And Their Capacity To Inhibit The Growth Of Hormone Dependent Mammary Cancer Cells, Unpublished Thesis, ITESM, Campus Monterrey. División de Ingeniería y Arquitectura, Monterrey, N.L. May 2003. (incorporated herein by reference, portions believed to be pertinent are attached as Appendix I.)

Izumi, T., Piskula, M. K., Osawa, S., Obata, A., Tobe, K., Saito, M., Kataoka, S., Kubota, Y., Kikuchi, M. 2000. Soy isoflavone aglycones are absorbed faster and in higher amounts than their glucosides in humans. J. Nutr. 130: 1695-1699.

Kähkönen, M. P., Heinonen, M. 2003 Antioxidant activity of anthocyanins and their aglycons. J. Agric. Food Chem. 51: 628-633.

Kalt, W., Forney, C. F., Martin, A., Prior, R. L. 1999. Antioxidant capacity, vitamin C, phenolics, and anthocyanins after fresh storage of small fruits. J. Agric. Food Chem. 47: 4638-4644

Kim, S. K., Akihisha, T., Tamura, T., Matsumoto, T., Yokota, T., Takashi, N. 1988. 24-methylene-25-methylcholesterol in *Phaseolus vulgaris* seed: Structural relation to brassinosteroids. Phytochemistry. 27(2): 629-631.

Lopez-Salinas, E., Cano-Reyes, O. Acosta-Gallegos, J. A., Becerra-Leor, E. N., Cruz-Chavez, F., Ortega-Zaleta, D. A., Vinay-Badillo, J. C. 1994. Negro Tacana, nueva variedad de frijol para el trópico húmedo de México. Folleto Técnico No. 10. División Agrícola. INIFAP.

Mabry, T. J., Markham, K. R., Thomas, M. B. 1970. The systematic identification of flavonoids. Springer-Verlag, NY.

Matsuura, M., Obata, A. 1993. Beta glucosidases from soybeans hydrolyze daidzin and genistin. J. Food Sci. 58:144-147.

Mazza, G., Fukumoto, L., Delaquis, P., Girard, B., Ewert, B. 1999. Anthocyanins phenolics and color of cabernet franc, merlot, and pinot noir wines from British Columbia. J. Agric. Food Chem. 47:4009-4017.

Nakamura, Y., Tsuiji, S., Tonogai, Y. 2000. Determination of the level of isoflavonoids in soybeans and soy-derived foods and estimation of isoflavonoids in the Japanese daily intake. J. AOAC Int. 83(3):635-650. Perrin, D. R., Whittle, C. P. 1972. The structure of phaseollidin. Tetrahedron Letters. 17: 1673-1676.

Rito-Palomares, M. 2004. Practical application of aqueous two-phase partition to process development for the recovery of biological products. J. Chromatog. B. 807:3-11.

Rodger, E. H., Grant, M. H. 1998. The effect of the flavonoids, quercetin, myricetin, and epicatechin on the growth and enzyme activities of MCF7 human breast cancer cells. Chemico-Biological Interactions. 116: 213-228.

Setchell, K. D. R., Brown, N. M., Desai, P., Zimmer-Nechemias, L., Wolfe, B. E., Brashear, W. T., Kirschner, A. S., Cassidy, A., Heubi, J. E. 2001. Bioavailability of pure isoflavones in healthy humans and analysis of commercial soy isoflavone supplements. J. Nutr. 131: 1362S-1375S.

Setchell, K. D. R., Aedin, C. 1999. Dietary Isoflavones: Biological Effects and Relevance to Human Health. J. Nutr. 129:758S-767S.

Sosulski, F. W., Dabrowski, K. J. 1984 Composition of free and hydrolyzable.phenolic acids in the flours and hulls often legume species. J. Agric. Food Chem. 32:131-133

Takeoka, G. R, Dao, L. T., Full, G. H., Wong, R. Y., Harden, L. A., Edwards, R. H., Berrios, J. de J. 1997. Characterization of black bean (*Phaseolus vulgaris* L.) anthocyanins. J. Agric. Food Chem. 45: 3395-3400.

Talcott, S. T.; Brenes, C. H.; Pires, D. M.; Del Pozo-Insfran, D. 2003. Phytochemical stability and color retention of copigmented and processed Muscadine grape juice. J. Agric. Food Chem. 51(4): 957-963

Vinson, J. A., Proch, J., Bose, P. 2001. Determination of quantity and quality of polyphenol antioxidants in foods and beverages. In: Methods in Enzymology "Flavonoids and other polyphenols". L. Packer (ed). Academic Press, San Diego, Calif.

Wang, S. Y.; Lin, H.-S. 2000. Antioxidant activity in fruits and leaves of blackberry, raspberry, and strawberry varies with cultivar and developmental stage. J. Agric. Food Chem. 48(2): 140-146.

Wang, S. Y.; Stretch, A. W. 2001. Antioxidant capacity in cranberry is influenced by cultivar and storage temperature. J. Agric. Food Chem. 49(2): 969-974.

Woodward, M. D. 1979. New isoflavonoids related to kievitone from *Phaseolus vulgaris*. Phytochemistry 18: 2007-2010.

We claim:

1. A process of making a black bean extract which comprises:
    (a) extracting a mixture of compounds from the black bean or hulls of the black bean with a polar solvent system consisting essentially of (i) one or more $C_1$-$C_6$ alcohol or (ii) water and a $C_1$-$C_6$-alcohol,
    (b) subjecting the mixture of compounds from extracting step (a) to a chromatographic separation step which comprises of a first elution step, wherein a first fraction is obtained, and a second elution step, wherein a second fraction, which is the isolated black bean extract, is obtained, wherein:
(i) the first fraction has less flavonols, flavones and isoflavones than the second fraction;
(ii) the first fraction also contains phenolic acids and other water soluble compounds; and
(iii) the second fraction contains flavonols, isoflavones, anthocyanins and a compound with a mass spectral ion peak of 981 Daltons.

2. The process of claim 1, wherein the black bean is selected from the genotypes Mex 332, Negro Coaxtla 91, Negro 8025, Negro San Luis, Negro Altiplano, Negro 150, NG-Sahuatoba, Negro Tacana, Negro Viscaya, Negro Otomi, Negro Perla or Negro INIFAP.

3. The process of any one of claims 1 or 2 wherein (a) is malted, sprouted or germinated black bean.

4. The process of claim 1, wherein the $C_1$-$C_6$ alcohol is selected from the group consisting of methanol and ethanol.

5. The process of claim 1, wherein the $C_1$-$C_6$ alcohol is methanol.

6. An isolated black bean extract for treating cancer selected from the group consisting of breast, prostate, colon, hepatic and leukemia prepared by
a process of making a black bean extract, wherein the black bean is from the genotype Mex 332, Negro Coaxtla 91, Negro 8025, Negro San Luis, Negro Altiplano, Negro 150, NG-Sahuatoba, Negro Tacana, Negro Viscaya, Negro Otomi, Negro Perla or Negro INIFAP which comprises:
(a) extracting a mixture of compounds from the black bean or hulls of the black bean with a polar solvent system consisting essentially of (i) one or more $C_1$-$C_6$ alcohol or (ii) water and a $C_1$-$C_6$ alcohol;
(b) subjecting the mixture of compounds from extracting step (a) to a chromatographic separation step which comprises of a first elution step, wherein a first fraction is obtained, and a second elution step, wherein a second fraction, which is the isolated black bean extract, is obtained, wherein:
(i) the first fraction has less flavonols, flavones and isoflavones than the second fraction;
(ii) the first fraction also contains phenolic acids and other water soluble compounds; and
(iii) the second fraction contains flavonols, isoflavones, anthocyanins and a compound with a mass spectral ion peak of 981 Daltons.

7. The isolated black bean extract of claim 6, wherein the black bean is selected from the genotypes Negro 8025, Negro Altiplano, Negro Tacana, Negro Otomi or Negro Perla.

8. The isolated black bean extract of claim 6, wherein said mass spectral ion peak of 981 Daltons when subjected to double ionization, gives mass spectral ion peaks of 797, 635, 599 and 441 Daltons.

9. A composition which comprises of a pharmaceutically effective amount of the black bean extract of claim 6 to treat a cancer selected from the group consisting of breast, prostate, colon, hepatic and leukemia and a pharmaceutically acceptable carrier and/or excipient.

10. A composition which comprises of a pharmaceutically effective amount of the black bean extract of claim 7 to treat a cancer selected from the group consisting of breast, prostate, colon, hepatic and leukemia and a pharmaceutically acceptable carrier and/or excipient.

11. A composition which comprises of a pharmaceutically effective amount of the black bean extract of claim 8 to treat a cancer selected from the group consisting of breast, prostate, colon, hepatic and leukemia and a pharmaceutically acceptable carrier and/or excipient.

12. A method for treating a cancer selected from the group consisting of breast, prostate, colon, hepatic and leukemia which comprises administering to a subject in need thereof or desirous thereof, a therapeutically effective amount of the composition of claim 9.

13. A method for treating a cancer selected from the group consisting of breast, prostate, colon, hepatic and leukemia which comprises administering to a subject susceptible to or in need thereof, a therapeutically effective amount of the composition of claim 10.

14. A method for treating a cancer selected from the group consisting of breast, prostate, colon, hepatic and leukemia which comprises administering to a subject in need thereof or desirous thereof, a therapeutically effective amount of the composition of claim 11.

15. The method of claim 12, wherein the cancer is breast, hepatic or colon cancer.

16. The method of claim 13, wherein the cancer is breast, hepatic or colon cancer.

17. The method of claim 16, wherein the cancer is breast cancer and the percent inhibition of breast cancer cells is greater than paclitaxel at identical concentrations or show the same percent inhibition of breast cancer with lower concentrations relative to paclitaxel.

18. A composition which comprises the black bean extract of claim 6.

19. A composition which comprises the black bean extract of claim 7.

20. A composition which comprises the black bean extract of claim 8.

21. The isolated black bean extract of claim 6, wherein the solvent for the first elution is a mixture of water and a $C_1$-$C_6$-alcohol and the solvent for the second elution is a $C_1$-$C_6$ alcohol.

22. The isolated black bean extract of claim 21, wherein the $C_1$-$C_6$-alcohol is methanol or ethanol.

23. The isolated black bean extract of claim 22, wherein the $C_1$-$C_6$-alcohol is methanol.

24. The isolated black bean extract of claim 6, wherein the first fraction contains less than 1% by weight of flavonols, flavones or isoflavones based on the dry weight of the compounds in the first fraction.

25. The isolated black bean extract of claim 24, wherein the amount of anthocyanins ranges from about 15 ppm to about 105 ppm.

26. The isolated black bean extract of claim 25, wherein the amount of anthocyanins ranges from about 15 ppm to about 60 ppm.

27. The isolated black bean extract of claim 26, wherein the anthocyanins are delphinidin, petunidin and malvidin.

28. The isolated black bean extract of claim 27, wherein the amount of delphinidin ranges from about 5 ppm to about 20 ppm, the amount of petunidin ranges from about 5 ppm to about 20 ppm and malvidin ranges from about 5 ppm to about 20 ppm.

29. The isolated black bean extract of claim 25, wherein the flavonols are one or more compounds selected from the group consisting of myricetin, myricetin 3'-rhamnoside, quercetin, quercetin 3-O-galactoside, quercetin 3-glucopyranoside, quercetin 4'-galactoside, kaempferol, kaempferol 3-O-glucoside, 3',4',5',5,7-pentahydroxyflavonol, 3',4',5,7-tetrahydroxyflavonol and 4',5,7-trihydroxyflavonol.

30. The isolated black bean extract of claim 29, wherein the solvent for the first elution is a mixture of water and a $C_1$-$C_6$-alcohol and the solvent for the second elution is a $C_1$-$C_6$ alcohol.

* * * * *